(12) United States Patent
Huang et al.

(10) Patent No.: US 12,128,044 B2
(45) Date of Patent: Oct. 29, 2024

(54) FUSED TRICYCLIC COMPOUNDS AND USES THEREOF IN MEDICINE

(71) Applicant: SUNSHINE LAKE PHARMA CO., LTD., Guangdong (CN)

(72) Inventors: Jianzhou Huang, Dongguan (CN); Qingyun Ren, Dongguan (CN); Jinfeng Xiong, Dongguan (CN); Yang Liu, Dongguan (CN); Xinchang Liu, Dongguan (CN); Siegfried Goldmann, Wuppertal (DE); Yingjun Zhang, Dongguan (CN); Yifeng Wang, Dongguan (CN); Weishun Liu, Dongguan (CN); Fangcai Yu, Dongguan (CN)

(73) Assignee: SUNSHINE LAKE PHARMA CO., LTD., Guangdong (CN)

( * ) Notice: Subject to any disclaimer, the term of this patent is extended or adjusted under 35 U.S.C. 154(b) by 936 days.

(21) Appl. No.: 17/266,961

(22) PCT Filed: Aug. 27, 2019

(86) PCT No.: PCT/CN2019/102754
§ 371 (c)(1),
(2) Date: Feb. 8, 2021

(87) PCT Pub. No.: WO2020/043080
PCT Pub. Date: Mar. 5, 2020

(65) Prior Publication Data
US 2021/0236493 A1 Aug. 5, 2021

(30) Foreign Application Priority Data

Aug. 28, 2018 (CN) .......................... 201810985779.5
Mar. 18, 2019 (CN) .......................... 201910201731.5

(51) Int. Cl.
| | |
|---|---|
| *C07D 471/04* | (2006.01) |
| *A61K 31/427* | (2006.01) |
| *A61K 31/429* | (2006.01) |
| *A61K 31/5025* | (2006.01) |
| *A61K 31/52* | (2006.01) |
| *A61K 31/675* | (2006.01) |
| *A61K 31/7056* | (2006.01) |
| *A61K 31/7068* | (2006.01) |
| *A61K 31/7072* | (2006.01) |
| *A61K 38/20* | (2006.01) |
| *A61K 38/21* | (2006.01) |
| *A61P 31/20* | (2006.01) |

(52) U.S. Cl.
CPC ........ *A61K 31/5025* (2013.01); *A61K 31/427* (2013.01); *A61K 31/429* (2013.01); *A61K 31/52* (2013.01); *A61K 31/675* (2013.01); *A61K 31/7056* (2013.01); *A61K 31/7068* (2013.01); *A61K 31/7072* (2013.01); *A61K 38/2013* (2013.01); *A61K 38/212* (2013.01); *A61K 38/215* (2013.01); *A61P 31/20* (2018.01); *C07D 471/04* (2013.01)

(58) Field of Classification Search
CPC .... C07D 471/04; A61K 31/5025; A61P 31/20
See application file for complete search history.

(56) References Cited

U.S. PATENT DOCUMENTS

| | | | |
|---|---|---|---|
| 9,458,153 B2 | 10/2016 | Han et al. | |
| 9,637,485 B2 | 5/2017 | Han et al. | |
| (Continued) | | | |

FOREIGN PATENT DOCUMENTS

| | | |
|---|---|---|
| CN | 106810548 A | 6/2017 |
| CN | 106928245 A | 7/2017 |
| (Continued) | | |

OTHER PUBLICATIONS

Dec. 9, 2019 Search Report issued in International Patent Application No. PCT/CN2019/102754.

(Continued)

*Primary Examiner* — Bruck Kifle
(74) *Attorney, Agent, or Firm* — Oliff PLC

(57) ABSTRACT

A fused tricyclic compound and application thereof in medicine, especially as a medicament for the treatment and/or prevention of hepatitis B. Specifically, the present invention relates to a compound having Formula (I) or a stereoisomer, a tautomer, an N-oxide, a solvate, a metabolite, a pharmaceutically acceptable salt or a prodrug thereof, wherein each variable is as defined in the specification. The present invention also relates to the use of a compound having Formula (I) or a stereoisomer, a tautomer, an N-oxide, a solvate, a metabolite, a pharmaceutically acceptable salt or a prodrug thereof as a medicament, especially as a medicament for the treatment and/or prevention of hepatitis B.

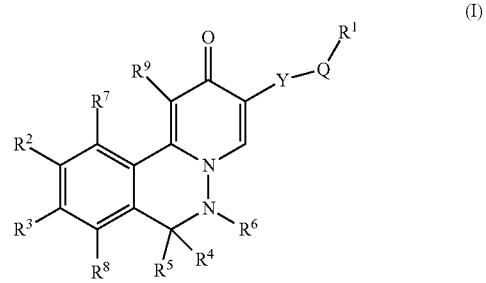

21 Claims, No Drawings

(56) References Cited

U.S. PATENT DOCUMENTS

| | | |
|---|---|---|
| 9,845,325 B2 | 12/2017 | Fu et al. |
| 9,920,049 B2 | 3/2018 | Yang et al. |
| 10,053,461 B2 | 8/2018 | Han et al. |
| 10,093,671 B2 | 10/2018 | Han et al. |
| 10,093,673 B2 | 10/2018 | Fu et al. |
| 10,150,740 B2 | 12/2018 | Cheng et al. |
| 10,239,872 B2 | 3/2019 | Chen et al. |
| 10,301,312 B2 | 5/2019 | Fu et al. |
| 10,336,751 B2 | 7/2019 | Cheng et al. |
| 10,442,804 B2 | 10/2019 | Aktoudianakis et al. |
| 10,865,211 B2 | 12/2020 | Panarese et al. |
| 2019/0314347 A1 | 10/2019 | Bailey et al. |
| 2020/0113879 A1 | 4/2020 | Liu et al. |
| 2020/0255428 A1 | 8/2020 | Catalano et al. |

FOREIGN PATENT DOCUMENTS

| | | |
|---|---|---|
| CN | 108530449 A | 9/2018 |
| CN | 108727378 A | 11/2018 |
| CN | 106928215 B | 3/2019 |
| CN | 110903284 A | 3/2020 |
| CN | 110950860 A | 4/2020 |
| CN | 111116577 A | 5/2020 |
| CN | 111116588 A | 5/2020 |
| CN | 111217811 A | 6/2020 |
| CN | 110724140 B | 10/2020 |
| WO | 2017/016960 A1 | 2/2017 |
| WO | 2017/216685 A1 | 12/2017 |
| WO | 2017/216686 A1 | 12/2017 |
| WO | 2018/019297 A1 | 2/2018 |
| WO | 2018/047109 A1 | 3/2018 |
| WO | 2018/073753 A1 | 4/2018 |
| WO | 2018/130152 A1 | 7/2018 |
| WO | 2018/154466 A1 | 8/2018 |
| WO | 2018/161960 A1 | 9/2018 |
| WO | 2018/214875 A1 | 11/2018 |
| WO | 2019/100735 A1 | 5/2019 |
| WO | 2019/110352 A1 | 6/2019 |
| WO | 2019/123285 A1 | 6/2019 |
| WO | 2019/143902 A2 | 7/2019 |
| WO | 2019/169539 A1 | 9/2019 |
| WO | 2019/177937 A1 | 9/2019 |
| WO | 2019/200109 A1 | 10/2019 |
| WO | 2020/063870 A1 | 4/2020 |
| WO | 2020/143604 A1 | 7/2020 |
| WO | 2020/150366 A1 | 7/2020 |

OTHER PUBLICATIONS

Dec. 9, 2019 Written Opinion issued in International Patent Application No. PCT/CN2019/102754.

FUSED TRICYCLIC COMPOUNDS AND USES THEREOF IN MEDICINE

CROSS-REFERENCE TO RELATED APPLICATION

The present application claims the priority and the benefit of the patent application No. 201810985779.5, filed with the State Intellectual Property Office of China on Aug. 28, 2018, and the patent application No. 201910201731.5, filed with the State Intellectual Property Office of China on Mar. 18, 2019, the disclosure of which are hereby incorporated by reference.

FIELD OF THE INVENTION

The present invention relates to a fused tricyclic compound and application thereof in medicine, especially as a medicament for the treatment and/or prevention of hepatitis B. The invention also relates to a composition of these fused tricyclic compounds together with other antiviral agents, and their use for the treatment and/or prevention of hepatitis B virus (HBV) infection.

BACKGROUND OF THE INVENTION

The hepatitis B virus belongs to the family of hepadnaviridae. It can cause acute and/or persistent or progressive chronic diseases. Many other clinical manifestations in the pathological morphology can be also caused by HBV—in particular chronic hepatitis, cirrhosis and hepatocellular carcinoma. According to estimates by the World Health Organization, 2 billion people worldwide have been infected with HBV, and there are about 350 million chronically infected people. About 1 million people die each year from liver failure, liver cirrhosis and primary hepatocellular carcinoma caused by HBV infection. (hepatocellular carcinoma, HCC)

Currently, the treatment of chronic hepatitis B (CHB) is mainly antiviral therapy. Interferon α (IFN-α) and pegylated IFN-α and five nucleoside (acid) analogues (lamivudine, adefovir dipivoxil, entecavir, telbivudine and tenofovir) were approved by the US Food and Drug Administration (FDA) for clinical treatment. Interferon is the first anti-HBV drug approved by the FDA. It mainly achieves the effect of clearing the virus by direct antiviral action and inducing the body's immune response. However, due to its low response rate, various side effects, expensive price and the limited treatment target, etc., its application is subject to many restrictions. The anti-HBV of nucleoside (acid) drugs has a specific effect on viral DNA polymerase and has a strong inhibitory effect on viral replication. Patients are better tolerant to drugs than interferon. However, the widespread long-term use of nucleoside (acid) drugs can induce DNA polymerase mutations to form drug resistance, leading to the emergence of drug-resistant strains, making treatment far less than the desired effect.

Therefore, there is still a need in the clinic for new compounds which can be effectively used as antiviral drugs, especially as drugs for treating and/or preventing hepatitis B.

SUMMARY OF THE INVENTION

The present invention relates to a novel class of fused tricyclic compound and their use in the preparation of a medicament for the treatment and prevention of HBV infection. The inventors have found that the novel fused tricyclic compounds of the present invention have good pharmacokinetic properties, good solubility, low toxicity, good liver microsome stability, and good inhibitory activity on the production or secretion of HBsAg and the replication of HBV DNA. It has a good application prospect in anti-HBV In particular, the compounds of the present invention, and pharmaceutically acceptable compositions thereof, are also effective in inhibiting HBV infection.

In one aspect, the present invention provides a compound having Formula (I) or a stereoisomer, a tautomer, an N-oxide, a solvate, a metabolite, a pharmaceutically acceptable salt or a prodrug thereof, wherein:

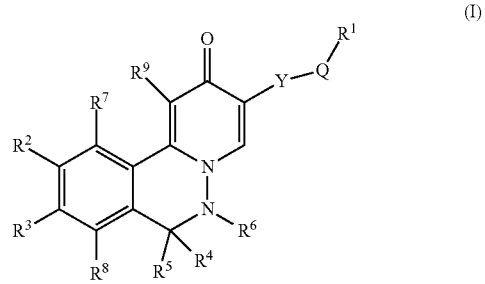

(I)

Y is a single bond, —$CH_2$— or —$C(=O)$—;
Q is a single bond, —O— or —$N(R^{10})$—;
$R^1$ is hydrogen, deuterium, fluorine, chlorine, bromine, iodine, OH, —COOH, heterocyclyl consisting of 5-6 ring atoms, heteroaryl consisting of 5-6 ring atoms, $C_{1-6}$ alkyl, $C_{2-6}$ alkenyl, $C_{2-6}$ alkynyl, $C_{3-7}$ cycloalkyl or $R^aR^bN$—, wherein each of the heterocyclyl consisting of 5-6 ring atoms, heteroaryl consisting of 5-6 ring atoms, $C_{1-6}$ alkyl, $C_{2-6}$ alkenyl, $C_{2-6}$ alkynyl and $C_{3-7}$ cycloalkyl is independently unsubstituted or substituted by 1, 2, 3 or 4 $R^v$;
$R^{10}$ is hydrogen, deuterium, $C_{1-6}$ alkyl or $C_{1-6}$ haloalkyl, or $R^{10}$, $R^1$ together with the nitrogen atom to which they are attached form a heterocyclyl consisting of 3 to 6 ring atoms, wherein each of the $C_{1-6}$ alkyl, $C_{1-6}$ haloalkyl and heterocyclyl consisting of 3-6 ring atoms is independently unsubstituted or substituted by 1, 2, 3 or 4 substituents selected from —COOH, =O, tetrazolyl or $C_{1-6}$ alkyl-$OC(=O)$—;
$R^2$ is hydrogen, deuterium, halogen, cyano, $C_{1-6}$ alkyl or $C_{1-6}$ alkoxy, wherein each of the $C_{1-6}$ alkyl and $C_{1-6}$ alkoxy is independently unsubstitued or substituted by 1, 2, 3, or 4 $R^w$;
$R^3$ is halogen (i.e. F, Cl, Br or I), $C_{1-6}$ alkyl, $C_{2-6}$ alkenyl, $C_{2-6}$ alkynyl, $C_{3-7}$ cycloalkyl, heterocyclyl consisting of 3 to 12 ring atoms, $C_{6-10}$ aryl and heteroaryl consisting of 5 to 10 ring atoms, wherein each of the $C_{1-6}$ alkyl, $C_{2-6}$ alkenyl, $C_{2-6}$ alkynyl, $C_{3-7}$ cycloalkyl, heterocyclyl consisting of 3 to 12 ring atoms, $C_{6-10}$ aryl and heteroaryl consisting of 5 to 10 atoms is independently unsubstitued or substituted by 1, 2, 3, or 4 $R^x$;
each $R^4$ and $R^5$ is independently hydrogen, deuterium, $C_{1-6}$ alkyl, $C_{1-6}$ alkylamino, $C_{1-6}$ alkoxy, $C_{2-6}$ alknyl, $C_{2-6}$ alkenyl, $C_{3-7}$ cycloalkyl or heterocyclyl consisting of 3 to 12 atoms, wherein each of the $C_{1-6}$ alkyl, $C_{1-6}$ alkylamino, $C_{1-6}$ alkoxy, $C_{2-6}$ alknyl, $C_{2-6}$ alkenyl, $C_{3-7}$ cycloalkyl or heterocyclyl consisting of 3 to 12 atoms is independently unsubstitued or substituted by 1, 2, 3, or 4 $R^y$;

or $R^4$, $R^5$ together with carbon atoms they are attached to form $C_{3-7}$ cycloalkyl or heterocyclyl consisting of 3 to 10 ring atoms;

$R^6$ is hydrogen, deuterium, $C_{1-6}$ alkyl, $C_{2-6}$ alkenyl, $C_{3-7}$ cycloalkyl, heterocyclyl consisting of 3 to 12 ring atoms, $C_{6-10}$ aryl or heteroaryl consisting of 5 to 10 ring atoms, wherein each of the $C_{1-6}$ alkyl, —$C_{2-6}$ alkenyl, $C_{3-7}$ cycloalkyl, heterocyclyl consisting of 3 to 12 ring atoms, $C_{6-10}$ aryl or heteroaryl consisting of 5 to 10 ring atoms is independently unsubstitued or substituted by 1, 2, 3, or 4 $R^z$;

each $R^7$, $R^8$ and $R^9$ is independently hydrogen, deuterium, F, Cl, Br, OH, cyano, $C_{1-6}$ alkyl, $C_{1-6}$ alkoxy, $C_{3-7}$ cycloalkyl, heterocyclyl consisting of 3 to 6 ring atoms, $C_{6-10}$ aryl or heteroaryl consisting of 5 to 10 ring atoms, wherein each of the $C_{1-6}$ alkyl, $C_{1-6}$ alkoxy, $C_{3-7}$ cycloalkyl, heterocyclyl consisting of 3 to 6 ring atoms, $C_{6-10}$ aryl or heteroaryl consisting of 5 to 10 ring atoms is independently unsubstitued or substituted by 1, 2, 3, or 4 $R^3$;

each $R^a$ and $R^b$ is independently hydrogen, deuterium, $C_{1-6}$ alkyl, $C_{1-6}$ alkoxy, $C_{2-6}$ alkenyl, $C_{2-6}$ alknyl, $C_{3-6}$ cycloalkyl, $C_{6-10}$ aryl, heterocyclyl consisting of 3 to 6 ring atoms or heteroaryl consisting of 5 to 10 ring atoms, wherein each of the $C_{1-6}$ alkyl, $C_{1-6}$ alkoxy, $C_{2-6}$ alkenyl, $C_{2-6}$ alknyl, $C_{3-6}$ cycloalkyl, $C_{6-10}$ aryl, heterocyclyl consisting of 3 to 6 ring atoms and heteroaryl consisting of 5 to 10 ring atoms is independently unsubstitued or substituted by 1, 2, 3, or 4 substituents selected from F, Cl, Br, CN, OH, amino, $C_{1-6}$ alkyl, $C_{1-6}$ haloalkyl, $C_{1-6}$ alkoxy or $C_{1-6}$ alkylamino;

each $R^v$, $R^w$, $R^y$, $R^z$ and $R^j$ is independently deuterium, F, Cl, Br, CN, =O, OH, —COOH, amino, $C_{1-6}$ alkyl, $C_{1-6}$ alkoxy, $C_{1-6}$ alkylthio, $C_{1-6}$ alkylamino, $C_{2-6}$ alkenyl, $C_{2-6}$ alknyl, $C_{3-7}$ cycloalkyl, heterocyclyl consisting of 3 to 6 ring atoms, $C_{6-10}$ aryl or heteroaryl consisting of 5 to 10 ring atoms, wherein each of the amino, $C_{1-6}$ alkyl, $C_{1-6}$ alkoxy, $C_{1-6}$ alkylthio, $C_{1-6}$ alkylamino, $C_{2-6}$ alkenyl, $C_{2-6}$ alknyl, $C_{3-7}$ cycloalkyl, heterocyclyl consisting of 3 to 6 ring atoms, $C_{6-10}$ aryl or heteroaryl consisting of 5 to 10 ring atoms is independently unsubstitued or substituted by 1, 2, 3, or 4 $R^e$;

each R is independently deuterium, F, Cl, Br, CN, =O, OH, —COOH, amino, $C_{1-12}$ alkyl, $C_{1-12}$ alkoxy, $C_{1-12}$ alkylthio, $C_{1-12}$ alkylamino, $C_{2-6}$ alkenyl, $C_{2-6}$ alknyl, $C_{3-7}$ cycloalkyl, heterocyclyl consisting of 3 to 12 ring atoms, $C_{6-10}$ aryl, heteroaryl consisting of 5 to 10 ring atoms or -L-$R^{11}$, wherein each of the amino, $C_{1-12}$ alkyl, $C_{1-12}$ alkoxy, $C_{1-12}$ alkylthio, $C_{1-12}$ alkylamino, $C_{2-6}$ alkenyl, $C_{2-6}$ alknyl, $C_{3-7}$ cycloalkyl, heterocyclyl consisting of 3 to 12 ring atoms, $C_{6-10}$ aryl, heteroaryl consisting of 5 to 10 ring atoms is independently unsubstitued or substituted by 1, 2, 3, or 4 $R^f$;

L is $C_{1-4}$ alkylene, $C_{1-3}$ heteroalkylene, —O—, —(C=O)—, —S(=O)$_q$ or —N($R^{12}$)—, wherein each of the $C_{1-4}$ alkylene and $C_{1-3}$ heteroalkylene is independently unsubstitued or substituted by 1, 2, 3, or 4 $R^g$;

$R^{11}$ is $C_{1-6}$ alkyl, $C_{1-6}$ alkoxy, $C_{3-7}$ cycloalkyl, heterocyclyl consisting of 3 to 12 ring atoms, $C_{6-10}$ aryl or heteroaryl consisting of 5 to 10 ring atoms, wherein each of the $C_{1-6}$ alkyl, $C_{1-6}$ alkoxy, $C_{3-7}$ cycloalkyl, heterocyclyl consisting of 3 to 12 ring atoms, $C_{6-10}$ aryl or heteroaryl consisting of 5 to 10 ring atoms is independently unsubstitued or substituted by 1, 2, 3, or 4 $R^h$;

each $R^e$, $R^f$, $R^g$ and $R^h$ is independently F, Cl, Br, CN, OH, =O, —COOH, —C(=O)O$C_{1-6}$ alkyl, —S(=O)$_2$—$C_{1-6}$ alkyl, —S(=O)$_2$—$C_{3-7}$ cycloalkyl, amino, $C_{1-6}$ alkyl, $C_{1-6}$ haloalkyl, $C_{1-6}$ alkoxy, $C_{1-6}$ alkylthio, $C_{1-6}$ haloalkoxy, $C_{1-12}$ alkylamino, $C_{2-6}$ alkenyl, $C_{2-6}$ alknyl, $C_{6-10}$ aryl, $C_{3-7}$ cycloalkyl, heteroaryl consisting of 5 to 6 ring atoms, heterocyclyl consisting of 3 to 6 ring atoms, $C_{1-6}$ alkoxy $C_{1-4}$ alkylene $C_{1-4}$ alkylamino $C_{1-4}$ alkylene;

$R^{12}$ is hydrogen, deuterium, $C_{1-6}$ alkyl or $C_{1-6}$ haloalkyl;

q is 0, 1 or 2.

In some embodiments, $R^1$ described herein is hydrogen, deuterium, fluorine, chlorine, bromine, iodine, OH, —COOH, heterocyclyl consisting of 5 ring atoms, heterocyclyl consisting of 6 ring atoms, heteroaryl consisting of 5 ring atoms, heteroaryl consisting of 6 ring atoms, $C_{1-4}$ alkyl, $C_{2-4}$ alkenyl, $C_{2-4}$ alkynyl, $C_{3-6}$ cycloalkyl or $R^aR^bN$—, wherein each of the heterocyclyl consisting of 5 ring atoms, heterocyclyl consisting of 6 ring atoms, heteroaryl consisting of 5 ring atoms, heteroaryl consisting of 6 ring atoms, $C_{1-4}$ alkyl, $C_{2-4}$ alkenyl, $C_{2-4}$ alkynyl and $C_{3-6}$ cycloalkyl is independently unsubstituted or substituted by 1, 2, 3 or 4 R;

$R^{10}$ is hydrogen, deuterium, $C_{1-4}$ alkyl or $C_{1-4}$ haloalkyl, or $R^{10}$, $R^1$ together with the nitrogen atom to which they are attached form a heterocyclyl consisting of 5 or 6 ring atoms, wherein each of the $C_{1-4}$ alkyl or $C_{1-4}$ haloalkyl, heterocyclyl consisting of 5 and 6 ring atoms is independently unsubstituted or substituted by 1, 2, 3 or 4 substituents selected from —COOH, =O, tetrazolyl or $C_{1-4}$ alkyl-O—C(=O)—;

$R^2$ is hydrogen, deuterium, halogen, cyano, methyl, ethyl, n-propyl, isopropyl, n-butyl, isobutyl, n-pentyl, n-hexyl, methoxy, ethoxy, 1-propoxy, 2-propyloxy, 1-butoxy, 2-methyl-1-propoxy, 2-butoxy, 2-methyl-2-propoxy or 1-pentyloxy, wherein each of the methyl, ethyl, n-propyl, isopropyl, n-butyl, isobutyl, n-pentyl, n-hexyl, methoxy, ethoxy, 1-propoxy, 2-propyloxy, 1-butoxy, 2-methyl-1-propoxy, 2-butoxy, 2-methyl-2-propoxy or 1-pentyloxy is unsubstituted or substituted by 1, 2, 3 or 4 $R^w$;

wherein, each $R^a$, $R^b$, $R^v$ and $R^w$ has the meaning described in the present invention.

In other embodiments, $R^1$ is hydrogen, deuterium, F, Cl, Br, I, OH, —COOH, thiazolyl, tetrazolyl, methyl, ethyl, n-propyl, isopropyl, vinyl, propenyl, allyl, ethynyl, propynyl, cyclopropyl, cyclobutyl, cyclopentyl cyclohexyl or $R^aR^bN$—, wherein each of the thiazolyl, tetrazolyl, methyl, ethyl, n-propyl, isopropyl, vinyl, propenyl, allyl, ethynyl, propynyl, cyclopropyl, cyclobutyl, cyclopentyl cyclohexyl is unsubstituted or substituted by 1, 2, 3 or 4 R;

$R^{10}$ is hydrogen, deuterium, methyl, ethyl, n-propyl, isopropyl or $C_{1-3}$ haloalkyl, or $R^{10}$ and $R^1$ together with the nitrogen atom to which they are attached form pyrrolidinyl, piperazinyl, piperidinyl or morpholinyl, wherein each of the methyl, ethyl, n-propyl, isopropyl, $C_{1-3}$ haloalkyl, pyrrolidinyl, piperazinyl, piperidinyl and morpholinyl is independently unsubstituted or substituted by 1, 2, 3 or 4 substituents selected from —COOH, =O, tetrazolyl or $C_{1-3}$ alkyl-O—C(=O)—;

wherein each $R^a$, $R^b$ and $R^v$ is as defined herein.

In some embodiments, $R^3$ is halogen (i.e. F, Cl, Br or I), $C_{1-4}$ alkyl, $C_{2-4}$ alkenyl, $C_{2-4}$ alkynyl, $C_{3-6}$ cycloalkyl, heterocyclyl consisting of 3-6 ring atoms, phenyl, naphthyl, heteroaryl consisting of 5 or 6 ring atoms, wherein each of the $C_{1-4}$ alkyl, $C_{2-4}$ alkenyl, $C_{2-4}$ alkynyl, $C_{3-6}$ cycloalkyl, heterocyclyl consisting of 3-6 ring atoms, phenyl, naphthyl, heteroaryl consisting of 5 or 6 ring atoms is independently unsubstituted or substituted by 1, 2, 3 or 4 R;
  wherein each R is as defined herein.

In other embodiments, $R^3$ described herein is halogen, methyl, ethyl, n-propyl, isopropyl, n-butyl, isobutyl, vinyl, propenyl, allyl, ethynyl, propynyl, propargyl, cyclopropyl, cyclobutyl, cyclopentyl, cyclohexyl, azetidinyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholyl, piperazinyl, phenyl, naphthyl, furyl, pyrrolyl, pyridyl, pyrazolyl, imidazolyl, triazolyl, tetrazolyl, oxazolyl, isoxazolyl, oxadiazole, 1,3,5-triazinyl, thiazolyl, thienyl, pyrazinyl, pyridazinyl or pyrimidinyl, wherein each of the methyl, ethyl, n-propyl, isopropyl, n-butyl, isobutyl, vinyl, propenyl, allyl, ethynyl, propynyl, propargyl, cyclopropyl, cyclobutyl, cyclopentyl, cyclohexyl, azetidinyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholyl, piperazinyl, phenyl, naphthyl, furyl, pyrrolyl, pyridyl, pyrazolyl, imidazolyl, triazolyl, tetrazolyl, oxazolyl, isoxazolyl, oxadiazole, 1,3,5-triazinyl, thiazolyl, thienyl, pyrazinyl, pyridazinyl or pyrimidinyl is unsubstituted or substituted by 1, 2, 3 or 4 $R^x$;
  wherein each R is as defined herein.

In some embodimets, each $R^4$ and $R^5$ is independently hydrogen, deuterium, $C_{1-4}$ alkyl, $C_{1-4}$ alkylamino, $C_{1-4}$ alkoxy, $C_{2-4}$ alknyl, $C_{2-4}$ alkenyl, $C_{3-6}$ cycloalkyl or heterocyclyl consisting of 3 to 6 ring atoms, wherein each of $C_{1-4}$ alkyl, $C_{1-4}$ alkylamino, $C_{1-4}$ alkoxy, $C_{2-4}$ alknyl, $C_{2-4}$ alkenyl, $C_{3-6}$ cycloalkyl and heterocyclyl consisting of 3 to 6 ring atoms is independently unsubstituted or substituted by 1, 2, 3 or 4 $R^y$;
  or $R^4$, $R^5$ together with the carbon atom to which they are attached form cyclopropyl, cyclobutyl, cyclopentyl, cyclohexyl or heterocyclyl consisting of 3-6 ring atoms;
  $R^6$ is hydrogen, deuterium, $C_{1-4}$ alkyl, $C_{2-4}$ alkenyl, $C_{3-6}$ cycloalkyl, heterocyclyl consisting of 3-6 ring atoms, phenyl, naphthyl, heteroaryl consisting of 5 or 6 ring atoms, wherein each of the $C_{1-4}$ alkyl, $C_{2-4}$ alkenyl, $C_{3-6}$ cycloalkyl and heterocyclyl consisting of 3-6 ring atoms, phenyl, naphthyl and heteroaryl consisting of 5 or 6 ring atoms is independently unsubstituted or substituted by 1, 2, 3 or 4 $R^z$;
  each $R^7$, $R^8$ and $R^9$ is independently hydrogen, deuterium, F, Cl, Br, OH, cyano, $C_{1-4}$ alkyl, $C_{1-4}$ alkoxy, $C_{3-6}$ cycloalkyl, heterocyclyl consisting of 3 to 6 ring atoms, phenyl, naphthyl or heteroaryl consisting of 5 or 6 ring atoms, wherein each of the $C_{1-4}$ alkyl, $C_{1-4}$ alkoxy, $C_{3-6}$ cycloalkyl, heterocyclyl consisting of 3 to 6 ring atoms, phenyl, naphthyl and heteroaryl consisting of 5 or 6 ring atoms is independently unsubstituted or substituted by 1, 2, 3 or 4 $R^3$;
  each $R^a$ and $R^b$ is independently hydrogen, deuterium, $C_{1-4}$ alkyl, alkoxy, $C_{2-4}$ alkenyl, $C_{2-4}$ alknyl, $C_{3-6}$ cycloalkyl, phenyl, naphthyl, heterocyclyl consisting of 3 to 6 ring atoms or heteroaryl consisting of 5 or 6 ring atoms, wherein each of the $C_{1-4}$ alkyl, alkoxy, $C_{2-4}$ alkenyl, $C_{2-4}$ alknyl, $C_{3-6}$ cycloalkyl, phenyl, naphthyl, heterocyclyl consisting of 3 to 6 ring atoms and heteroaryl consisting of 5 or 6 ring atoms is independently unsubstituted or substituted by 1, 2, 3 or 4 selected from F, Cl, Br, CN, OH, amino, $C_{1-4}$ alkyl, $C_{1-4}$ haloalkyl, $C_{1-4}$ alkoxy or $C_{1-4}$ alkylamino;
  wherein each $R^y$, $R^z$ and Rd is as defined herein.

In other embodiments, each $R^4$ and $R^5$ is independently hydrogen, deuterium, methyl, ethyl, n-propyl, isopropyl, n-butyl, isobutyl, N-methylamino, N-ethylamino, N,N-dimethylamino, N,N-diethylamino, N-propylamino, methoxy, ethoxy, 1-propoxy, 2-propoxy, 1-butoxy, 2-methyl-1-propoxy, 2-butoxy, 2-methyl-2-propoxy, ethenyl, propenyl, allyl, ethynyl, propynyl, propargyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl or piperazinyl, wherein each of the methyl, ethyl, n-propyl, isopropyl, n-butyl, isobutyl, N-methylamino, N-ethylamino, N,N-dimethylamino, N,N-diethylamino, N-propylamino, methoxy, ethoxy, 1-propoxy, 2-propoxy, 1-butoxy, 2-methyl-1-propoxy, 2-butoxy, 2-methyl-2-propoxy, ethenyl, propenyl, allyl, ethynyl, propynyl, propargyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl and piperazinyl is independently unsubstituted or substituted by 1, 2, 3 or 4 $R^y$;
  or $R^4$, $R^5$ together with the carbon atom to which they are attached form cyclopropyl, cyclobutyl, cyclopentyl, cyclohexyl, azetidinyl, oxetanyl, oxacyclopropyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl or piperazinyl;
  $R^6$ is hydrogen, deuterium, methyl, ethyl, n-propyl, isopropyl, n-butyl, isobutyl, tert-butyl, vinyl, propenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of the methyl, ethyl, n-propyl, isopropyl, n-butyl, isobutyl, tert-butyl, vinyl, propenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3 or 4 $R^z$;
  each $R^7$, $R^8$ and $R^9$ is independently hydrogen, deuterium, F, Cl, Br, OH, cyano, methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furanyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of the methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, cyclopropyl, cyclobutyl, cyclopentyl, cyclo hexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furanyl, pyrrolyl, pyridyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3 or 4 $R^j$;

each $R^a$ and $R^b$ is independently hydrogen, deuterium, methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, vinyl, propenyl, ethynyl, propynyl, propargyl, cyclopropyl, cyclobutyl, cyclopentyl, cyclohexyl, phenyl, naphthyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furanyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of the methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, vinyl, propenyl, ethynyl, propynyl, propargyl, cyclopropyl, cyclobutyl, cyclopentyl, cyclohexyl, phenyl, naphthyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furanyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3 or 4 substituents selected from F, Cl, Br, CN, OH, amino, $C_{1-3}$ alkyl, $C_{1-3}$ haloalkyl, $C_{1-3}$ alkoxy or $C_{1-3}$ alkylamino;

wherein each $R^y$, $R^z$ and $R^j$ is as defined herein.

In some embodiments, each of $R^v$, $R^w$, $R^y$, $R^z$ and $R^j$ is independently deuterium, F, Cl, Br, CN, =O, OH, —COOH, amino, $C_{1-4}$ alkyl, $C_{1-4}$ alkoxy, $C_{1-4}$ alkylthio, $C_{1-4}$ alkylamino, $C_{2-4}$ alkenyl, $C_{2-4}$ alkynyl, $C_{3-6}$ cycloalkyl, heterocyclyl consisting of 3 to 6 ring atoms, phenyl, naphthyl, heteroaryl consisting of 5 or 6 ring atoms, wherein each of the amino, $C_{1-4}$ alkyl, $C_{1-4}$ alkoxy, $C_{1-4}$ alkylthio, $C_{1-4}$ alkylamino, $C_{2-4}$ alkenyl, $C_{2-4}$ alkynyl, $C_{3-6}$ cycloalkyl, heterocyclyl consisting of 3 to 6 ring atoms, phenyl, naphthyl, heteroaryl consisting of 5 or 6 ring atoms is unsubstituted or substituted by 1, 2, 3 or 4 $R^e$;

wherein each $R^e$ is as defined herein.

In other embodiments, each of $R^v$, $R^w$, $R^y$, $R^z$ and $R^j$ is independently deuterium, F, Cl, Br, CN, =O, OH, —COOH, amino, methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, $C_{1-3}$ alkylthio, N-methylamino, N-ethylamino, N,N-dimethylamino, N,N-diethylamino, N-propylamino, vinyl, propylene, ethynyl, propynyl, propargyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of the amino, methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, $C_{1-3}$ alkylthio, N-methylamino, N-ethylamino, N,N-dimethylamino, N,N-diethylamino, N-propylamino, vinyl, propylene, ethynyl, propynyl, propargyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3 or 4 $R^e$;

wherein each $R^e$ is as defined herein.

In some embodiments, each $R^x$ is independently deuterium, F, Cl, Br, CN, =O, OH, —COOH, amino, $C_{1-6}$ alkyl, $C_{1-6}$ alkoxy, $C_{1-6}$ alkylthio, $C_{1-6}$ alkylamino, $C_{2-4}$ alkenyl, $C_{2-4}$ alkynyl, $C_{3-6}$ cycloalkyl, heterocyclyl consisting of 3 to 6 ring atoms, phenyl, naphthyl, heteroaryl consisting of 5 to 6 atoms or -L-$R^{11}$, wherein each of the amino, $C_{1-6}$ alkyl, $C_{1-6}$ alkoxy, $C_{1-6}$ alkylthio, $C_{1-6}$ alkylamino, $C_{2-4}$ alkenyl, $C_{2-4}$ alkynyl, $C_{3-6}$ cycloalkyl, heterocyclyl consisting of 3 to 6 ring atoms, phenyl, naphthyl and heteroaryl consisting of 5 to 6 atoms is independently unsubstituted or substituted by 1, 2, 3 or 4 R;

wherein each $R^f$ is as defined herein.

In other embodiments, each $R^x$ is independently deuterium, F, Cl, Br, CN, =O, —COOH, amino, methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, $C_{1-3}$ alkylthio, N-methylamino, N-ethylamino, N,N-dimethylamino, N,N-diethylamino, N-propylamino, vinyl, propenyl, ethynyl, propynyl, 1-propynyl, cyclopropyl, cyclobutyl, cyclopentyl, cyclohexyl, azetidinyl, oxetanyl, oxacyclopropyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl or -L-$R^{11}$, wherein each of the amino, methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, $C_{1-3}$ alkylthio, N-methylamino, N-ethylamino, N,N-dimethylamino, N,N-diethylamino, N-propylamino, vinyl, propenyl, ethynyl, propynyl, 1-propynyl, cyclopropyl, cyclobutyl, cyclopentyl, cyclohexyl, azetidinyl, oxetanyl, oxacyclopropyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3, 5-triazinyl, thiazolyl, thienyl, pyrazinyl, pyridazinyl and pyrimidinyl is independently unsubstituted or substituted by 1, 2, 3 or 4 $R^f$;

wherein each $R^f$ is as defined herein.

In other embodiments, each $R^x$ is independently deuterium, F, Cl, Br, CN, =O, —COOH, amino, methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, $CH_3$—$S(=O)_2$—, $CH_3CH_2$—$S(=O)_2$—, $CH_3CH_2CH_2$—$S(=O)_2$—, $(CH_3)_2CH$—$S(=O)_2$—, N-methylamino, N-ethylamino, N,N-dimethylamino, N,N-diethylamino, N-propylamino, vinyl, propenyl, ethynyl, propynyl, 1-propynyl, cyclopropyl, cyclobutyl, cyclopentyl, cyclohexyl, azetidinyl, oxobutyl, oxopropyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl or -L-R$^1$, wherein each of the amino, methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, $CH_3$—S(=O)$_2$—, $CH_3CH_2$—S(=O)$_2$—, $CH_3CH_2CH_2$—S(=O)$_2$—, $(CH_3)_2CH$—S(=O)$_2$—, N-methylamino, N-ethylamino, N,N-dimethylamino, N,N-diethylamino, N-propylamino, vinyl, propenyl, ethynyl, propynyl, 1-propynyl, cyclopropyl, cyclobutyl, cyclopentyl, cyclohexyl, azetidinyl, oxobutyl, oxopropyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl is independently unsubstituted or substituted by 1, 2, 3 or 4 R$^f$;

wherein each R$^f$ is as defined herein.

In some embodiments, R$^{11}$ is $C_{1-4}$ alkyl, $C_{1-4}$ alkoxy, $C_{3-6}$ cycloalkyl, heterocyclyl consisting of 3 to 6 ring atoms, phenyl, naphthyl or heteroaryl consisting of 5 to 6 ring atoms, wherein each of the $C_{1-4}$ alkyl, $C_{1-4}$ alkoxy, $C_{3-6}$ cycloalkyl, heterocyclyl consisting of 3 to 6 ring atoms, phenyl, naphthyl and heteroaryl consisting of 5 to 6 ring atoms is independently unsubstituted or substituted by 1, 2, 3 or 4 R$^h$;

wherein each R$^h$ is as defined herein.

In other embodiments, R$^{11}$ is methyl, ethyl, n-propyl, isopropyl, methoxy, ethoxy, 1-propoxy, 2-propoxy, 1-butoxy, 2-methyl-1-propoxy, 2-butoxy, cyclopropyl, cyclobutyl, cyclopentyl, cyclohexyl, azetidinyl, oxetanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of the methyl, ethyl, n-propyl, isopropyl, methoxy, ethoxy, 1-propoxy, 2-propoxy, 1-butoxy, 2-methyl-1-propoxy, 2-butoxy, cyclopropyl, cyclobutyl, cyclopentyl, cyclohexyl, azetidinyl, oxetanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3 or 4 R$^h$;

wherein each R$^h$ is as defined herein.

In some embodiments, each R$^e$, R$^g$ and R$^h$ is independently F, Cl, Br, CN, OH, =O, —COOH, —C(=O)OC$_{1-4}$ alkyl, —S(=O)$_2$—C$_{1-4}$ alkyl, —S(=O)$_2$-cyclopropyl, —S(=O)$_2$-cyclobutyl, —S(=O)$_2$-cyclopentyl, —S(=O)$_2$-cyclohexyl, amino, $C_{1-4}$ alkyl, $C_{1-4}$ haloalkyl, $C_{1-4}$ alkoxy, $C_{1-4}$ alkylthio, $C_{1-4}$ haloalkoxy, $C_{1-6}$ alkylamino, $C_{2-4}$ alkenyl, $C_{2-4}$ alkynyl, phenyl, naphthyl, $C_{3-6}$ cycloalkyl, heteroaryl consisting of 5 or 6 ring atoms, heterocyclyl consisting of 5 or 6 ring atoms, $C_{1-4}$ alkoxy $C_{1-3}$ alkylene or $C_{1-4}$ alkylamino $C_{1-3}$ alkylene; R$^{12}$ is hydrogen, deuterium, $C_{1-4}$ alkyl or $C_{1-4}$ haloalkyl.

In other embodiments, each R$^e$, R$^f$, R$^g$ and R$^h$ is independently F, Cl, Br, CN, OH, =O, —COOH, —C(=O)O-methyl, —C(=O)O-ethyl, —C(=O)O-n-propyl, —C(=O)O-isopropyl, —C(=O)O-n-butyl, —C(=O)O-isobutyl, —C(=O)O-sec-butyl, —C(=O)O-tert-butyl, —S(=O)$_2$-methyl, —S(=O)$_2$-ethyl, —S(=O)$_2$-n-propyl, —S(=O)$_2$-isopropyl, —S(=O)$_2$-n-butyl, —S(=O)$_2$-isobutyl, —S(=O)$_2$-sec-butyl, —S(=O)$_2$-tert-butyl, —S(=O)$_2$-cyclopropyl, —S(=O)$_2$-cyclobutyl, —S(=O)$_2$-cyclopentyl, —S(=O)$_2$-cyclohexyl, amino, methyl, ethyl, n-propyl, isopropyl, n-butyl, isobutyl, $C_{1-3}$ haloalkyl, methoxy, ethoxy, 1-propoxy, 2-propoxy, 1-butoxy, 2-methyl-1-propoxy, 2-butoxy, $C_{1-3}$ alkylthio, $C_{1-3}$ haloalkoxy, N-methylamino, N-ethylamino, N,N-dimethylamino, N,N-diethylamino, N-propylamino, vinyl, propenyl, ethynyl, propynyl, propargyl, phenyl, naphthyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, $C_{1-3}$ alkoxy $C_{1-2}$ alkylene or $C_{1-3}$ alkylamino $C_{1-2}$ alkylene;

R$^{12}$ is hydrogen, deuterium, $C_{1-3}$ alkyl or $C_{1-3}$ haloalkyl.

In other aspect, the invention also provides a pharmaceutical composition comprising a compound of the invention, optionally further comprising a pharmaceutically acceptable excipient or a combination of said excipients.

In some embodiments, the pharmaceutical compositions of the present invention further comprise other anti-HBV drugs.

In some embodiments, the pharmaceutical compositions of the present invention, wherein other anti-HBV drugs are HBV polymerase inhibitors, immunomodulators or interferons.

In some embodiments, the pharmaceutical compositions of the present invention, wherein other anti-HBV drugs are lamivudine, telbivudine, Tenofovir Disoprox, entecavir, adefovir dipivoxil, Alfaferone, Alloferon, Celmoleukin, Clevudine, emtricitabine, famciclovir, interferon, HepaTect CP, Interferon, Interferon α-1b, Interferon α, Interferon α-2a, Interferon β-1a, Interferon α-2, Interleukin-2, mivotilate, nitazoxanide, peginterferon α-2a, ribavirin, interferon-A, Sizofiran, Euforavac, Ampligen, Phosphazid, Heplisav, interferon α-2b, levamisole or Propagermanium.

In other aspect, provided herein is use of the compound or the pharmaceutical composition disclosed herein in the manufacture of a medicament for preventing treating or reducing a viral disease.

In some embodiments, the use of the invention, wherein the viral disease is Hepatitis B virus infection or a disease caused by Hepatitis B virus infection.

In other embodiments, the use of the invention, wherein the disease caused by Hepatitis B virus infection is cirrhosis or hepatocellular carcinoma.

In other aspect, provided herein is use of the compound or the pharmaceutical composition disclosed herein in the manufacture of a medicament for inhibiting the formation or secretion of HBsAg, and/or inhibiting the formation of HBV DNA.

In other aspect, provided herein is use of the compound or the pharmaceutical composition disclosed herein in the manufacture of a medicament for preventing, treating or reducing Hepatitis B disease.

Another aspect of the invention relates to a method of preventing, treating or ameliorating a patient's HBV disorder, the method comprising administering to a patient a pharmaceutically acceptable effective amount of a compound of the invention.

Another aspect of the invention relates to a method of preventing, treating or ameliorating a patient's HBV disorder, the method comprising administering to a patient a pharmaceutically acceptable effective amount of pharmaceutical composition containing the compound of the present invention.

In other aspect, provided herein is use of the compound disclosed herein in the manufacture of a medicament for preventing, managing or treating HBV illness in a patient, or lessening the severity thereof.

In other aspect, provided herein is use of the pharmaceutical composition containing the compound disclosed herein in the manufacture of a medicament for preventing, managing or treating HBV illness in a patient, or lessening the severity thereof.

Another aspect of the invention relates to a method of inhibiting HBV infection, the method comprising contacting a cell with a compound or composition of the invention at a dose effective to inhibit HBV In other embodiments, the method further comprises contacting the cells with an anti-HBV agent.

Another aspect of the invention relates to a method of treating a patient with HBV disease, the method comprising administering to the patient a therapeutically effective amount of a compound of the invention or a composition thereof. In other embodiments, the method further comprises administering another HBV treatment.

Another aspect of the invention relates to a method of inhibiting HBV infection in a patient, the method comprising administering to the patient a therapeutically effective amount of a compound of the invention or a composition thereof. In other embodiments, the method further comprises administering another HBV treatment.

In other aspect, provided herein is a method of preparing, separating or purifying the compound of Formula (I).

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

The present invention will list the documents corresponding to the specific content of the determination, and the examples are accompanied by the diagrams of the structural formula and the chemical formula. The present invention is intended to cover all alternatives, modifications, and equivalents, which may be included in the field of the invention as defined by the appended claims. Those skilled in the art will recognize many methods and materials that are similar or equivalent to those described herein, which can be used in the practice of the present invention. The invention is in no way limited to the description of methods and substances. There are many documents and similar substances that differ or contradict the application of the present invention, including but not limited to the definition of terms, the usage of terms, the techniques described, or the scope as controlled by the present application.

The invention will apply the following definitions unless otherwise indicated. For the purposes of the present invention, chemical elements are defined in accordance with the Periodic Table of the Elements, CAS version and Handbook of Chemicals, 75, $^{th}$Ed, 1994. Additionally, general principles of organic chemistry are described in "Organic Chemistry", Thomas Sorrell, University Science Books, Sausalito: 1999, 1999, and "March's Advanced Organic Chemistry," by Michael B. Smith and Jerry March, John Wiley&Sons, New York: 2007, So all the content is a fusion of references.

As described herein, the compounds disclosed herein may optionally be substituted with one or more substituents, such as are illustrated generally below, or as exemplified by particular classes, subclasses, and species of the invention. In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. At various places in the present specification, substituents of compounds disclosed herein are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

Furthermore, what need to be explained is that the phrase "each . . . is independently" and "each of . . . and . . . is independently", unless otherwise stated, should be broadly understood. The specific options expressed by the same symbol are independent of each other in different groups; or the specific options expressed by the same symbol are independent of each other in same groups.

The term "alkyl" or "alkyl group" refers to a saturated linear or branched-chain monovalent hydrocarbon radical of 1 to 20 carbon atoms, wherein the alkyl radical may be optionally and independently substituted with one or more substituents described herein. In some embodiments, the alkyl group contains 1-12 carbon atoms. In other embodiments, the alkyl group contains 1-8 carbon atoms. In other embodiments, the alkyl group contains 1-6 carbon atoms. In still other embodiments, the alkyl group contains 1-4 carbon atoms. In yet other embodiments, the alkyl group contains 1-3 carbon atoms. Further examples of alkyl groups include, but are not limited to, methyl(Me, —$CH_3$), ethyl (Et, —$CH_2CH_3$), n-propyl(n-Pr, —$CH_2CH_2CH_3$), isopropyl(i-Pr, —$CH(CH_3)_2$), b-butyl(n-Bu, —$CH_2CH_2CH_2CH_3$), 2-methylpropyl or isobutyl (i-Bu, —$CH_2CH(CH_3)_2$), 1-methylpropyl or sec-butyl(s-Bu, —$CH(CH_3)CH_2CH_3$), tert-butyl(t-Bu, —$C(CH_3)_3$), n-pentyl(—$CH_2CH_2CH_2CH_2CH_3$), 2-pentyl(—$CH(CH_3)CH_2CH_2CH_3$), 3-pentyl(—$CH(CH_2CH_3)_2$), 2-methyl-2-butyl(-$C(CH_3)_2CH_2CH_3$), 3-methyl-2-butyl(-$CH(CH_3)CH(CH_3)_2$), 3-methyl-1-butyl(-$CH_2CH_2CH(CH_3)_2$), 2-methyl-1-butyl(-$CH_2CH(CH_3)CH_2CH_3$), orthohexyl(-$CH_2CH_2CH_2CH_2CH_2CH_3$), 2-hexyl(-$CH(CH_3)CH_2CH_2CH_2CH_3$), 3-hexyl(-$CH(CH_2CH_3)(CH_2CH_2CH_3)$), 2-methyl-2-pentyl(-$C(CH_3)_2CH_2CH_2CH_3$), 3-methyl-2-pentyl(-$CH(CH_3)CH(CH_3)CH_2CH_3$), 4-methyl-2-pentyl(-$CH(CH_3)CH_2CH(CH_3)_2$), 3-methyl-3-pentyl(-$C(CH_3)(CH_2CH_3)_2$), 2-methyl-3-pentyl(-$CH(CH_2CH_3)CH(CH_3)_2$), 2, 3-dimethyl-2-butyl(-$C(CH_3)_2CH(CH_3)_2$), 3,3-dimethyl-2-butyl(-$CH(CH_3)C(CH_3)_3$), n-heptyl, n-octyl, etc. The term "alkyl" or the prefix "alk-" is inclusive of both straight chain and branched saturated carbon chain. The term "haloaliphatic" as used herein means that the aliphatic group is replaced by one or more of the same or different halogen atoms, wherein aliphatic group or alkyl group has the meaning as described in the present invention, and the halogen atom is fluorine, chlorine, bromine or iodine. Such examples include, but are not limited to, trifluoromethyl, trifluoroethyl, etc.

The term "alkoxyalkyl" refers to an alkyl group substituted with one or more alkoxy groups, wherein the alkyl groups are as defined herein. In some embodiments, the haloalkyl group contains 1-12 carbon atoms. In other embodiments, the haloalkyl group contains 1-10 carbon atoms. In other embodiments, the haloalkyl group contains 1-8 carbon atoms. In still other embodiments, the haloalkyl group contains 1-6 carbon atoms. In yet other embodiments, the haloalkyl group contains 1-4 carbon atoms and in still yet other embodiments, the haloalkyl group contains 1-3 carbon atoms. Such examples include, but are not limited to, trifluoromethyl, trifluoroethyl, etc.

The terms "carboxy" or "carboxyl", whether used alone or with other terms (such as "carboxyalkyl"), refers to —$CO_2H$ or —COOH.

The terms "carboxy" or "carboxyl", whether used alone or with other terms (such as "carboxyalkyl"), refers to —(C=O)—.

The term "alkylamino" and "alkylamino" are used interchangeably, including "N-alkylamino" and "N,N-dialkylamino", wherein amino groups are independently substituted with one or two $C_{1-12}$ alkyl, respectively. In some embidiments, the alkylamino radical is "lower alkylamino" radical having one or two $C_{1-12}$ alkyl groups attached to a nitrogen atom. In other embodiments, the alkylamino radical refers to $C_{1-6}$ lower alkylamino group. In still other embodiments, the alkylamino radical refers to $C_{1-4}$ lower alkylamino group. Suitable alkylamino groups may be monoalkylamino or dialkylamino, examples of which include, but are not limited to, N-methylamino, N-ethylamino, N,N-dimethylamino, N,N-diethylamino, N-propylamino, N,N-dipropylamino, and the like, wherein the alkylamino group may be independently unsubstituted or substituted by one or more substituents described herein.

The term "alkylene" refers to a saturated divalent hydrocarbon group derived from a straight or branched chain saturated hydrocarbon by the removal of two hydrogen atoms. Unless otherwise specified, the alkylene group contains 1-12 carbon atoms. In other embodiments, the alkylene group contains 1-6 carbon atoms. In other embodiments, the alkyl group contains 1-4 carbon atoms. In still other embodiments, the alkyl group contains 1-3 carbon atoms. In other embodiments, the alkylene group contains 1-2 carbon atoms. Such examples include methylene (—$CH_2$—), ethylene (—$CH_2CH_2$—), propylene (—$CH_2CH_2CH_2$—), isopropyl (—CH($CH_3$)$CH_2$—), butylene(-$CH_2CH_2CH_2CH_2$—), pentylene(-$CH_2CH_2CH_2CH_2CH_2$—), subhexyl (—$CH_2CH_2CH_2CH_2CH_2CH_2$—), heptylene (—$CH_2CH_2CH_2CH_2CH_2CH_2CH_2$—), octylene (—$CH_2CH_2CH_2CH_2CH_2CH_2CH_2CH_2$—), etc., wherein the alkylene group may be independently unsubstituted or substituted by one or more substituents described herein.

The term "alkenyl" denotes a straight or branched chain monovalent hydrocarbon radical containing from 2 to 12 carbon atoms, or from 2 to 8 carbon atoms, or from 2 to 6 carbon atoms, or from 2 to 4 carbon atoms, wherein at least one position of C—C is sp2 double bond, wherein the alkenyl group may be independently unsubstituted or substituted by one or more substituents described herein, including Including "Cis", "Trans" or "Z", "E" isomers; wherein specific examples include, but are not limited to, vinyl(-CH=$CH_2$), propylene (—CH=$CHCH_3$), allyl (—$CH_2$CH=$CH_2$), etc. Wherein the alkenyl group may be independently unsubstituted or substituted by one or more substituents described herein.

The term "alkynyl" denotes a linear or branched monovalent hydrocarbon group containing from 2 to 12 carbon atoms, or from 2 to 8 carbon atoms, or from 2 to 6 carbon atoms, or from 2 to 4 carbon atoms, wherein at least one position of C—C is sp3 triple, wherein the alkynyl group may be independently unsubstituted or substituted by one or more substituents described herein, specific examples include, but are not limited to, ethynyl groups (—C≡CH), propargyl (—$CH_2$C≡CH), propynyl (—C≡C—$CH_3$), 1-alkynyl (—$CH_2CH_2$C≡CH), 2-acetylene (—$CH_2$C≡$CCH_3$), 3-acetylene (—C≡$CCH_2CH_3$), etc., wherein the alkynyl group may be independently unsubstituted or substituted by one or more substituents described herein.

The term "alkoxy" refers to an alkyl group, as previously defined, attached to the parent molecular moiety via an oxygen atom. Unless otherwise specified, the alkoxy group contains 1-20 carbon atoms. In some embodiments, the alkoxy group contains 1-12 carbon atoms. In other embodiments, the alkoxy group contains 1-8 carbon atoms. In still other embodiments, the alkoxy group contains 1-6 carbon atoms. In yet other embodiments, the alkoxy group contains 1-4 carbon atoms and in still yet other embodiments, the alkoxy group contains 1-3 carbon atoms.

Examples of alkoxy groups include, but are not limited to, methoxy group (MeO, —$OCH_3$), ethoxy group (EtO, —$OCH_2CH_3$), 1-propoxy (n-PrO, n-propoxy, —$OCH_2CH_2CH_3$), 2-propoxy (i-PrO, i-propoxy, —OCH($CH_3$)$_2$), 1-butoxy (n-BuO, n-butoxy, —$OCH_2CH_2CH_2CH_3$), 2-methyl-1-propoxy (i-BuO, i-butoxy, —$OCH_2$CH($CH_3$)$_2$), 2-butoxy (s-BuO, s-butoxy, —OCH($CH_3$)$CH_2CH_3$), 2-methyl-2-propoxy (t-BuO, t-butoxy, —OC($CH_3$)$_3$), 1-pentyloxy (n-pentyloxy, —$OCH_2CH_2CH_2CH_2CH_3$), 2-pentyloxy (—OCH($CH_3$)$CH_2CH_2CH_3$), 3-pentyloxy (—OCH($CH_2CH_3$)$_2$), 2-methyl-2-butoxy (—OC($CH_3$)$_2CH_2CH_3$), 3-methyl-2-butoxy (—OCH($CH_3$)CH($CH_3$)$_2$), 3-methyl-1-butoxy (—$OCH_2CH_2$CH($CH_3$)$_2$), 2-methyl-1-butoxy (—$OCH_2$CH($CH_3$)$CH_2CH_3$), etc., wherein the alkoxy group may be independently unsubstituted or substituted by one or more substituents described herein.

The term "haloalkoxy" refers to alkoxy, as the case may be, substituted with one or more halogen atoms, wherein the alkoxy is as defined herein. In some embodiments, the haloalkoxy group contains 1-12 carbon atoms. In other embodiments, the haloalkoxy group contains 1-10 carbon atoms. In other embodiments, the haloalkoxy group contains 1-8 carbon atoms. In still other embodiments, the haloalkoxy group contains 1-6 carbon atoms. In yet other embodiments, the haloalkoxy group contains 1-4 carbon atoms and in still yet other embodiments, the haloalkoxy group contains 1-3 carbon atoms. Such examples include but are not limited to trifluoromethoxy.

The terms "carbocyclic", "carbocyclyl" and "carbocyclic" are used interchangeably herein to refer to a non-aromatic carbon ring system which is saturated or contains one or more units of unsaturation and contains from 3 to 14 carbon ring atoms. In some embodiments, the number of carbon atoms is 3-12; in other embodiments, the number of carbon atoms is 3-10; in other embodiments, the number of carbon atoms is 3-8; in other embodiments, the number of carbon atoms is 3-6; in other embodiments, the number of carbon atoms is 5-6; in other embodiments, the number of carbon atoms is 5-8. In other embodiments, the number of carbon atoms is 6-8. "Carbocyclyl" includes monocyclic, bicyclic or polycyclic fused, spiro or bridged carbocyclic ring systems, and also includes a polycyclic ring system in which a carbocyclic ring may be fused to one or more non-aromatic carbocyclic or heterocyclic rings or one or more aromatic rings or combinations thereof, wherein the attached atomic group or point is on the carbocyclic ring. Bicyclic carbocyclyl includes bridged bicyclic carbocyclyl, fused bicyclic carbocyclyl and spirobicyclic carbocyclyl, and "fused" bicyclic ring system comprises two rings sharing two adjacent ring atoms. Abridged bicyclic group includes two rings sharing 3 or 4 adjacent ring atoms. The spiro ring system shares 1 ring atom. Some non-limiting examples of the carbocyclyl include cycloalkyl, cycloalkenyl and cycloalkynyl. Further non-limiting examples of carbocyclyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Bridged carbocyclyls include, but are not limited to, bicyclo[2.2.2]octyl, bicyclo[2.2.1]heptyl, bicyclo[3.3.1]nonyl, bicyclo[3.2.3]nonyl, etc.

The term "cycloalkyl" means a saturated mono-, bi-, or tricyclic ring consisting of 3-12 ring carbon atoms, in which there has one or more attachment points attached to the remainder of the molecule. In some embodiments, cycloalkyl is a ring system containing from 3 to 10 ring carbon atoms; in other embodiments, cycloalkyl is a ring system containing from 3 to 8 ring carbon atoms; in other embodiments, cycloalkyl is a ring system containing from 3 to 7 ring carbon atoms; in other embodiments, cycloalkyl is a ring system containing from 5 to 8 ring carbon atoms; in other embodiments, cycloalkyl is a ring system containing from 3 to 6 ring carbon atoms; in other embodiments, cycloalkyl is a ring system containing from 5 to 6 ring carbon atoms; examples of cycloalkyl groups include, but are not limited to, cyclopropyl, cyclobutyl, cyclopentyl, cyclohexyl, etc; the cycloalkyl group may be independently unsubstituted or substituted by one or more substituents described herein.

The terms "heterocyclyl" and "heterocycle" are used interchangeably herein, refer to a saturated or partially saturated non-aromatic monocyclic, bicyclic or tricyclic ring system containing from 3 to 12 ring atoms, wherein at least one ring member is selected from nitrogen, sulfur and oxygen, and this ring system has one or more connection points connected to the rest of the molecule. The term "heterocyclyl" includes monocyclic, bicyclic or polycyclic fused, spiro or bridged heterocyclic ring systems, also includes polycyclic ring system in which a heterocyclic ring can be fused to one or more non-aromatic carbocyclic or heterocyclic rings or one or more aromatic rings or a combination thereof, wherein the attached atomic group or point is on the heterocyclic ring. Bicyclic heterocyclsyl include bridged bicyclic heterocyclyl, fused bicyclic heterocyclyl and spirobicyclic heterocyclyl. Unless otherwise specified, a —CH$_2$— group in the heterocyclyl can be optionally replaced by a —C(=O)— group. In which, the sulfur can be optionally oxygenized to S-oxide and the nitrogen can be optionally oxygenized to N-oxide. In some embodiments, heterocyclyl is a ring system composed of 3 to 12 ring atoms; in other embodiments, heterocyclyl is a ring system composed of 3 to 8 ring atoms; in other embodiments, heterocyclyl is a ring system composed of 3 to 6 ring atoms; in other embodiments, heterocyclyl is a ring system composed of 5 to 7 ring atoms; in other embodiments, heterocyclyl is a ring system composed of 5 to 8 ring atoms; in other embodiments, heterocyclyl is a ring system composed of 6 to 8 ring atoms; in other embodiments, heterocyclyl is a ring system composed of 5 to 6 ring atoms; in other embodiments, heterocyclyl is a ring system composed of 3 ring atoms; in other embodiments, heterocyclyl is a ring system composed of 4 ring atoms; in other embodiments, heterocyclyl is a ring system composed of 7 ring atoms; in other embodiments, heterocyclyl is a ring system composed of 8 ring atoms.

Examples of heterocycles include, but are not limited to, pyrrolidinyl, tetrahydrofuranyl, dihydrofuranyl, tetrahydrothiophenyl, tetrahydropyranyl, dihydropyranyl, tetrahydrothiopyranyl, piperidinyl, morpholinyl, thiomorpholinyl, thiamethane, piperazinyl, homopiperazinyl, azetidinyl, oxetanyl, thioheterobutyl, homopiperidinyl, oxacyclopropyl, azepanyl, oxetan, thiaheptyl, oxazepine, diazepine, thiazepine, 2-pyrroline, 3-pyrrolyl, indanyl, 2H-pyranyl, 4H-pyranyl, dioxanyl, 1,3-dioxopentyl, pyrazolinyl, dithiaalkyl, dithialimyl, dihydrothienyl, pyrazolidine, imidazolinyl, imidazolidinyl, 1,2,3,4-tetrahydroisoquinolinyl, 3-azabicyclo[3.1.0]hexyl, 3-azabicyclo[4.1.0]heptyl, azabicyclo[2.2.2]hexyl, 3H-mercaptoquinazinyl and N-pyridyl urea. Examples of the heterocyclyl also include 1,1-dioxythiomorpholinyl; wherein non-limiting examples of carbon atoms on the ring being replaced by oxo (=O) groups include pyrimidinedione, 1,2,4-thiadiazol-5(4H)-keto, 1,2,4-oxadiazol-5(4H)-keto, 1H-1,2,4-triazole-5(4H)-keto, etc.; wherein examples of the ring carbon atom substituted by the =S group include, but are not limited to, 1,2,4-oxadiazol-5(4H)-thioketo, 1,3,4-oxadiazole-2 (3H))-thioketone, etc. The heterocyclyl may be optionally substituted with one or more substituents disclosed herein.

The terms "heterocyclylalkylene" and "heterocyclylalkyl" are used interchangeably herein to mean that the alkyl group is substituted by 1, 2, 3 or 4 heterocyclyls, wherein the heterocyclyl, alkyl and alkylene group have the meanings described herein. Some non-limiting examples of such group include pyrrole-2-methyl, morpholine-4-methyl, etc.

The terms "heterocyclyl alkoxy" refers to that the alkoxy group is substituted by 1, 2, 3 or 4 heterocyclyls, wherein the heterocyclyl and alkoxy have the meanings described herein. Some non-limiting examples of such group include pyrrole-2-methoxy, piperidine-2-ethoxyl, etc.

The term "heterocyclylamino" refers to heterocyclyl substituted alkylamino, wherein the nitrogen atom is connected to the rest of the molecule. Wherein the heterocyclyl and alkylamino are defined as the invention described herein. Examples of such groups include, but are not limited to, piperazine-2-ethylamino, morpholine-4-ethylamino, and the like.

The term "heteroatom" refers to one or more of oxygen, sulfur, nitrogen, phosphorus and silicon, including any oxidized form of nitrogen, sulfur, or phosphorus; the quaternized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl, R represents a substituent described in the present invention).

The term "halogen" or "halogen atom" means F, Cl, Br or I.

The term "unsaturated" refers to a moiety having one or more units of unsaturation.

The term "aryl" used alone or as a substantial part of "aralkyl", "aralkyloxy" or "aryloxyalkyl", refers to monocyclic, bicyclic and tricyclic carbocyclic ring systems having a total of six to fourteen carbon members, or six to twelve carbon members, or six to ten carbon members, wherein at least one ring in the system is aromatic, wherein each ring in the system contains 3 to 7 carbon members and that has a single point or multipoint of attachment to the rest of the molecule. The term "aryl" may be used interchangeably with the term "aryl ring" or "aromatic ring". Some non-limiting examples of the aryl group include phenyl, naphthyl and anthracene. The cycloalkenyl group may be optionally substituted with one or more substituents disclosed herein.

The term "heteroaryl" used alone or as a major part of "heteroarylalkyl" or "heteroarylalkoxy" refers to monocyclic, bicyclic and tricyclic carbocyclic ring systems having a total of five to sixteen ring members, wherein at least one ring in the system is aromatic, and in which at least one ring member is selected from heteroatom, and wherein each ring in the system contains 5 to 7 ring members and that has a single point or multipoint of attachment to the rest of the molecule. The term "hetreroaryl" and "heteroaromatic ring" or "heteroaromatic compound" can be used interchangeably herein. In one embodiment, a 5-14 membered heteroaryl comprises 1, 2, 3 or 4 heteroatoms independently selected from O, S and N. In one embodiment, a 5-12 membered heteroaryl comprises 1, 2, 3 or 4 heteroatoms independently selected from O, S and N. In one embodiment, a 5-10 membered heteroaryl comprises 1, 2, 3 or 4 heteroatoms independently selected from O, S and N. In one embodiment, a 5-8 membered heteroaryl comprises 1, 2, 3 or 4 heteroatoms independently selected from O, S and N. In one embodiment, a 5-7 membered heteroaryl comprises 1, 2, 3 or 4 heteroatoms independently selected from O, S and N. In one embodiment, a 5-6 membered heteroaryl comprises 1, 2, 3 or 4 heteroatoms independently selected from O, S and N. In one embodiment, a 5 membered heteroaryl comprises 1, 2, 3 or 4 heteroatoms independently selected from O, S and N. In one embodiment, a 6 membered heteroaryl comprises 1, 2, 3 or 4 heteroatoms independently selected from O, S and N.

In other embodiments, heteroaryl groups include, but are not limited to the following monocyclic group: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5H-tetrazolyl, 2H-tetrazolyl), triazolyl (e.g., 2-triazolyl, 5-triazolyl, 4H-1,2,4-triazolyl, 1H-1,2,4-triazolyl and 1,2,3-triazolyl), 2-thienyl, 3-thienyl, pyrazolyl (e.g., 2-pyrazolyl and 3-pyrazolyl), isothiazolyl, 1,2,3-oxadiazolyl, 1,2,5-oxadiazolyl, 1,2,4-oxadiazolyl, 1,3,4-oxadiazolyl, 1,2,3-thiodiazolyl, 1,3,4-thiadiazolyl, 1,2,5-thiadiazolyl, pyrazinyl, 1,3,5-triazinyl; heteroaryl groups also include, but are not limited to the following bis or tricyclic groups: benzimidazolyl, benzofuranyl, benzothienyl, indolyl (e.g., 2-indolyl), purinyl, quinolyl (e.g., 2-quinolinyl, 3-quinolinyl, 4-quinolinyl), isoquinolinyl (e.g., 1-isoquinolinyl, 3-isoquinolinyl or 4-isoquinolinyl), phenoxathiin group, dibenzimidazolyl group, dibenzofuranyl group or dibenzothiophene group, etc. The heteroaryl group is optionally substituted with one or more substituents disclosed herein.

The term "heteroarylalkyl" and "heteroarylalkylene" used interchangeably herein refers to an alkyl group substituted with one or more heteroaryl groups, wherein the alkylene group, alkyl group and heteroaryl group are as defined herein. Some non-limiting examples include pyridine-2-ethyl, thiazol-2-methyl, imidazole-2-ethyl, pyrimidine-2-propyl, and the like.

The term "sulfonyl", whether used alone or in conjunction with other terms like "alkylsulfonyl", denotes a divalent group —$SO_2$—. The term "alkylsulfonyl" refers to an alkyl-substituted sulfonyl group which forms an alkylsulfonyl group (e.g. —$SO_2CH_3$).

The term "alkylthio" refers to a linear or branched $C_{1-12}$ alkyl chain binding to a bivalent sulphur atom, wherein the alkyl group is as defined herein. In some embodiments, alkylthio is a lower $C_{1-6}$ alkylthio group, in other embodiments, alkylthio is a lower $C_{1-4}$ alkylthio group, in other embodiments, alkylthio is a lower $C_{1-3}$ alkylthio group, such examples include, but are not limited to methylthio ($CH_3S$—), ethylthio, etc.

The terms "aralkyl", "arylalkyl" and "arylalkylene" are used interchangeably herein to denote an aryl-substituted alkyl group, wherein alkylene, aryl and alkyl groups have the meanings as described herein. In some embodiments, the arylalkyl group refers to a "lower aralkyl" radical having aryl radical(s) attached to $C_{1-6}$ alkyl. In other embodiments, the arylalkyl radical refers to an alkyl group attached to $C_{1-3}$ alkyl. Some non-limiting examples of such radical include benzyl, diphenylmethyl, phenylethyl, and the like. The aralkyl group may be optionally substituted with one or more substituents disclosed herein.

The term "haloalkyl substituted aryl" denotes an aryl group which may be substituted by one or more of the same or different haloalkyl groups; wherein haloalkyl and aryl groups have the meanings as described herein Such examples include, but are not limited to, 2-trifluoromethylphenyl, 3,5-bis(trifluoromethyl)phenyl, 3-trifluoromethylphenyl, 4-trifluoromethylphenyl, 2,6-bis(trifluoromethyl)phenyl, etc.

The term "halogen-substituted aryl" denotes an aryl group which may be substituted by one or more of the same or different halogen atoms; wherein halogen atoms (halogen) and aryl groups have the meanings as described herein. Such examples include, but are not limited to, fluorophenyl, difluorophenyl, trifluorophenyl, chlorophenyl, dichlorophenyl, trichlorophenyl, bromophenyl, tribromophenyl, dibromophenyl, fluorochlorophenyl, fluorobromophenyl, chlorobromophenyl, etc.

The terms "alkoxyalkylene" and "alkoxyalkyl" are used interchangeably herein to mean that the alkyl group is substituted by 1, 2, 3 or 4 alkoxy groups, wherein the alkoxy group, alkyl and alkylene group have the meanings described herein. Such examples include, but are not limited to, methoxymethylene ($CH_3OCH_2$—), ethoxymethylene ($CH_3CH_2OCH_2$—), etc.

The terms "alkylaminoalkylene" and "alkylaminoalkyl" are used interchangeably herein to mean that the alkyl group is substituted by 1, or 2 alkylamino groups, wherein the alkylamino group, alkyl and alkylene group have the meanings described herein. Such examples include, but are not limited to, N-methylaminomethylene ($CH_3NHCH_2$—), N-ethylaminomethylene ($CH_3CH_2NHCH_2$—), N,N-dimethylaminomethylene (($CH_3)_2NCH_2$—), etc.

Unless otherwise stated, structures depicted herein also include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric mixtures of the present compounds are within the scope disclosed herein.

An "N-oxide" refers to one or more than one nitrogen atoms oxidised to form an N-oxide, where a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g. a peroxycarboxylic acid) (See, Advanced Organic Chemistiy, by Jerry March, 4th Edition, Wiley Interscience, pages). More particularly, N-oxides can be made by the procedure of L. W. Deady (Syn. Comm. 1977, 7, 509-514) in which the amine compound is reacted with m-chloroperoxybenzoic acid (MCPBA), for example, in an inert solvent such as dichloromethane.

The term "prodrug" refers to a compound that is transformed in vivo into a compound of Formula (I). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic ($C_1$-$C_{24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in T. Higuchi and V Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al., Prodrugs: Design and Clinical Applications, *Nature Review Drug Discovery*, 2008, 7, 255-270, and S. J. Hecker et al, Prodrugs of Phosphates and Phosphonates, *Journal of Medicinal Chemistry*, 2008, 51, 2328-2345.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

A "metabolite" is a product produced through metabolism in the body of a specified compound or salt thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

Stereochemical definitions and conventions used herein generally follow S. P. Parker Ed. McGraw-Hill Dictionary of Chemical Terms (1984) McGraw-Hill Book Company, New York and Eliel et al., "Stereochemistry of Organic Compounds", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

The term "tautomer" or "tautomeric form" refers to structural isomers of different energies which are interconvertible via a low energy barrier. Some non-limiting examples of proton tautomers (also known as prototropic tautomers) include interconversions via migration of a proton, such as keto-enol and imine-enamine isomerizations. Valence tautomers include interconversions by reorganization of some of the bonding electrons.

A "pharmaceutically acceptable salts" refers to organic or inorganic salts of a compound disclosed herein. Pharmaceutically acceptable salts are well known in the art. For example, Berge et al., describe pharmaceutically acceptable salts in detail in J. Pharmacol Sci, 1977, 66:1-19, which is incorporated herein by reference. Some non-limiting examples of pharmaceutically acceptable and nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, 2-hydroxy propionate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. If the compound disclosed herein is an acid, the desired salt may be prepared by any suitable method, for example, treatment of the free acid with an inorganic or organic base, such as an amine (primary, secondary or tertiary), an alkali metal hydroxide, ammonium, $N^+(R^{14})_4$ salt or alkaline earth metal hydroxide, and the like. Some non-limiting examples of suitable salts include organic salts derived from amino acids, such as glycine and arginine; ammonia, such as primary, secondary and tertiary amine, $N^+(R^{14})_4$ salt, wherein $R^{14}$ is H, $C_{1-4}$ alkyl, $C_{6-10}$ aryl, $C_{6-10}$ aryl-$C_{1-4}$ alkyl, and the like; and cyclic amines, such as piperidine, morpholine and piperazine, and inorganic salts derived from sodium, calcium, potassium, magnesium, manganese, iron, copper, zinc, aluminum, lithium, and the like, and further include, when appropriate, nontoxic ammonium, quaternary ammonium and amine cations formed using counterions such as halide, hydroxide, carboxylate, sulfate, phosphate, nitrate, $C_{1-8}$ sulfonate and aryl sulfonate.

The term "solvate" refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid and ethanolamine. The term "hydrate" refers to the complex where the solvent molecule is water.

The term "protecting group" or "Pg" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC), benzyloxycarbonyl (CBZ) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl)ethyl, 2-(trimethylsilyl) ethoxy-methyl, 2-(p-toluenesulfonyl) ethyl, 2-(p-nitrophenylsulfonyl)-ethyl, 2-(diphenylphosphino)-ethyl, nitroethyl and the like. For a general description of protecting groups and their use, see T. W. Greene, Protective Groups in Organic Synthesis, John Wiley & Sons, New York, 1991; and P. J. Kocienski, Protecting Groups, Thieme, Stuttgart, 2005.

DESCRIPTION OF COMPOUNDS OF THE INVENTION

The compounds of the present invention, and pharmaceutically acceptable compositions thereof, are also effective in inhibiting HBV infection.

In one aspect, the present invention provides a compound having Formula (I) or a stereoisomer, a tautomer, an N-oxide, a solvate, a metabolite, a pharmaceutically acceptable salt or a prodrug thereof, wherein:

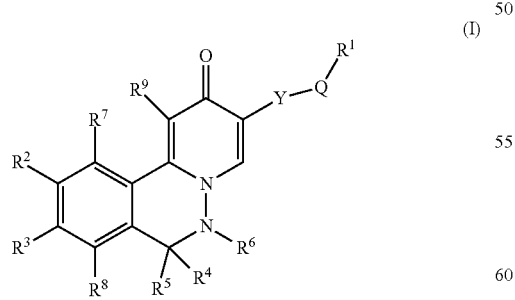

(I)

Y is a single bond, —CH$_2$— or —C(=O)—;
Q is a single bond, —O— or —N(R$^{10}$)—;
R$^1$ is hydrogen, deuterium, fluorine, chlorine, bromine, iodine, OH, —COOH, a heterocyclyl consisting of 5-6 ring atoms, a heteroaryl consisting of 5-6 ring atoms, $C_{1-6}$ alkyl, $C_{2-6}$ alkenyl, $C_{2-6}$ alkynyl, $C_{3-7}$ cycloalkyl or R$^a$R$^b$N—, wherein each of the heterocyclyl consisting of 5-6 ring atoms, heteroaryl consisting of 5-6 ring atoms, $C_{1-6}$ alkyl $C_{2-6}$ alkenyl, $C_{2-6}$ alkynyl and $C_{3-7}$ cycloalkyl is independently unsubstituted or substituted by 1, 2, 3 or 4 R$^v$;

R$^{10}$ is hydrogen, deuterium, $C_{1-6}$ alkyl or $C_{1-6}$ haloalkyl, or R$^{10}$, R$^1$ together with the nitrogen atom to which they are attached form a heterocyclyl consisting of 3 to 6 ring atoms, wherein each of the $C_{1-6}$ alkyl, $C_{1-6}$ haloalkyl and heterocyclyl consisting of 3-6 ring atoms is unsubstituted or substituted by 1, 2, 3 or 4 substituents selected from —COOH, =O, tetrazolyl or $C_{1-6}$ alkyl-OC(=O)—;

R$^2$ is hydrogen, deuterium, halogen, cyano, $C_{1-6}$ alkyl or $C_{1-6}$ alkoxy, wherein each of the $C_{1-6}$ alkyl and $C_{1-6}$ alkoxy is independently unsubstitued or substituted by 1, 2, 3, or 4 R$^w$;

R$^3$ is halogen, $C_{1-6}$ alkyl, $C_{2-6}$ alkenyl, $C_{2-6}$ alkynyl, $C_{3-7}$ cycloalkyl, heterocyclyl consisting of 3 to 12 ring atoms, $C_{6-10}$ aryl and heteroaryl consisting of 5 to 10 ring atoms, wherein each of the $C_{1-6}$ alkyl, $C_{2-6}$ alkenyl, $C_{2-6}$ alkynyl, $C_{3-7}$ cycloalkyl, heterocyclyl consisting of 3 to 12 ring atoms, $C_{6-10}$ aryl and heteroaryl consisting of 5 to 10 atoms is independently unsubstituted or substituted by 1,2,3, or 4 R$^x$;

each R$^4$ and R$^5$ is independently hydrogen, deuterium, $C_{1-6}$ alkyl, $C_{1-6}$ alkylamino, $C_{1-5}$ alkoxy, $C_{2-6}$ alknyl, $C_{2-6}$ alkenyl, $C_{3-7}$ cycloalkyl or heterocyclyl consisting of 3 to 12 atoms, wherein each of the $C_{1-6}$ alkyl, $C_{1-6}$ alkylamino, $C_{1-6}$ alkoxy, $C_{2-6}$ alknyl, $C_{2-6}$ alkenyl, $C_{3-7}$ cycloalkyl or heterocyclyl consisting of 3 to 12 atoms is independently unsubstitued or substituted by 1, 2, 3, or 4 R$^y$;

or R$^4$, R$^5$ together with the atoms to which they are attached form $C_{3-7}$ cycloalkyl or heterocyclyl consisting of 3 to 10 atoms;

R$^6$ is hydrogen, deuterium, $C_{1-6}$ alkyl, $C_{2-6}$ alkenyl, $C_{3-7}$ cycloalkyl, heterocyclyl consisting of 3 to 12 ring atoms, $C_{6-10}$ aryl or heteroaryl consisting of 5 to 10 ring atoms, wherein each of the $C_{1-6}$ alkyl, $C_{2-6}$ alkenyl, $C_{3-7}$ cycloalkyl, heterocyclyl consisting of 3 to 12 ring atoms, $C_{6-10}$ aryl or heteroaryl consisting of 5 to 10 ring atoms is independently unsubstitued or substituted by 1, 2, 3, or 4 R$^z$;

each R$^7$, R$^8$ and R$^9$ is independently hydrogen, deuterium, F, Cl, Br, OH, cyano, $C_{1-6}$ alkyl, $C_{1-6}$ alkoxy, $C_{3-7}$ cycloalkyl, heterocyclyl consisting of 3 to 6 ring atoms, $C_{6-10}$ aryl or heteroaryl consisting of 5 to 10 ring atoms, wherein each of the $C_{1-6}$ alkyl, $C_{1-6}$ alkoxy, $C_{3-7}$ cycloalkyl, heterocyclyl consisting of 3 to 6 ring atoms, $C_{6-10}$ aryl or heteroaryl consisting of 5 to 10 ring atoms is independently unsubstitued or substituted by 1, 2, 3, or 4 R$^j$;

each R$^a$ and R$^b$ is independently hydrogen, deuterium, $C_{1-6}$ alkyl, $C_{1-6}$ alkoxy, $C_{2-6}$ alkenyl, $C_{2-6}$ alknyl, $C_{3-6}$ cycloalkyl, $C_{6-10}$ aryl, heterocyclyl consisting of 3 to 6 ring atoms or heteroaryl consisting of 5 to 10 ring atoms, wherein $C_{1-6}$ alkyl, $C_{1-6}$ alkoxy, $C_{2-6}$ alkenyl, $C_{2-6}$ alknyl, $C_{3-6}$ cycloalkyl, $C_{6-10}$ aryl, heterocyclyl consisting of 3 to 6 ring atoms or heteroaryl consisting of 5 to 10 ring atoms is independently unsubstitued or substituted by 1, 2, 3, or 4 substituents selected from F, Cl, Br, CN, OH, amino, $C_{1-6}$ alkyl, $C_{1-6}$ haloalkyl, $C_{1-6}$ alkoxy or $C_{1-6}$ alkylamino;

each R$^v$, R$^w$, R$^y$, R$^z$ and R$^j$ is independently deuterium, F, Cl, Br, CN, =O, OH, —COOH, amino, $C_{1-6}$ alkyl, $C_{1-6}$ alkoxy, $C_{1-6}$ alkylthio, $C_{1-6}$ alkylamino, $C_{2-6}$ alkenyl, $C_{2-6}$ alknyl, $C_{3-7}$ cycloalkyl, heterocyclyl consisting of 3 to 6 ring atoms, $C_{6-10}$ aryl or heteroaryl consisting of 5 to 10 ring atoms, wherein each of the amino, $C_{1-6}$ alkyl, $C_{1-6}$ alkoxy, $C_{1-6}$ alkylthio, $C_{1-6}$ alkylamino, $C_{2-6}$ alkenyl, $C_{2-6}$ alknyl, $C_{3-7}$ cycloalkyl, heterocyclyl consisting of 3 to 6 ring atoms, $C_{6-10}$ aryl or heteroaryl consisting of 5 to 10 ring atoms is independently unsubstitued or substituted by 1, 2, 3, or 4 $R^e$;

each $R^x$ is independently deuterium, F, Cl, Br, CN, =O, OH, —COOH, amino, $C_{1-12}$ alkyl, $C_{1-12}$ alkoxy, $C_{1-12}$ alkylthio, $C_{1-12}$ alkylamino, $C_{2-6}$ alkenyl, $C_{2-6}$ alknyl, $C_{3-7}$ cycloalkyl, heterocyclyl consisting of 3 to 12 ring atoms, $C_{6-10}$ aryl, heteroaryl consisting of 5 to 10 ring atoms or -L-$R^1$, wherein each of the amino, $C_{1-12}$ alkyl, $C_{1-12}$ alkoxy, $C_{1-12}$ alkylthio, $C_{1-12}$ alkylamino, $C_{2-6}$ alkenyl, $C_{2-6}$ alknyl, $C_{3-7}$ cycloalkyl, heterocyclyl consisting of 3 to 12 ring atoms, $C_{6-10}$ aryl, heteroaryl consisting of 5 to 10 ring atoms is independently unsubstitued or substituted by 1, 2, 3, or 4 $R^f$;

L is $C_{1-4}$ alkylene, $C_{1-3}$ heteroalkylene, —O—, —(C=O)—, —S(=O)$_q$ or —N($R^{12}$)—, wherein each of the $C_{1-4}$ alkylene and $C_{1-3}$ heteroalkylene is independently unsubstitued or substituted by 1, 2, 3, or 4 $R^g$;

$R^{11}$ is $C_{1-6}$ alkyl, $C_{1-6}$ alkoxy, $C_{3-7}$ cycloalkyl, heterocyclyl consisting of 3 to 12 ring atoms, $C_{6-10}$ aryl or heteroaryl consisting of 5 to 10 ring atoms, wherein each of the $C_{1-6}$ alkyl, $C_{1-6}$ alkoxy, $C_{3-7}$ cycloalkyl, heterocyclyl consisting of 3 to 12 ring atoms, $C_{6-10}$ aryl or heteroaryl consisting of 5 to 10 ring atoms is independently unsubstitued or substituted by 1, 2, 3, or 4 $R^h$;

each $R^e$, $R^f$, R and $R^h$ is independently selected from F, Cl, Br, CN, OH, =O, —COOH, —C(=O)O$C_{1-6}$ alkyl, —S(=O)$_2$—$C_{1-6}$ alkyl, —S(=O)$_2$—$C_{3-7}$ cycloalkyl, amino, $C_{1-6}$ alkyl, $C_{1-6}$ haloalkyl, $C_{1-6}$ alkoxy, $C_{1-6}$ alkylthio, $C_{1-6}$ haloalkoxy, $C_{1-12}$ alkylamino, $C_{2-6}$ alkenyl, $C_{2-6}$ alknyl, $C_{6-10}$ aryl, $C_{3-7}$ cycloalkyl, heteroaryl consisting of 5 to 6 ring atoms, heterocyclyl consisting of 3 to 6 ring atoms, $C_{1-6}$ alkoxy $C_{1-4}$ alkylene or $C_{1-4}$ alkylamino $C_{1-4}$ alkylene;

$R^{12}$ is hydrogen, deuterium, $C_{1-6}$ alkyl or $C_{1-6}$ haloalkyl; q is 0, 1 or 2.

In some embodiments, $R^1$ is hydrogen, deuterium, fluorine, chlorine, bromine, iodine, OH, —COOH, heterocyclyl consisting of 5 ring atoms, heterocyclyl consisting of 6 ring atoms, heteroaryl consisting of 5 ring atoms, heteroaryl consisting of 6 ring atoms, $C_{1-4}$ alkyl, $C_{2-4}$ alkenyl, $C_{2-4}$ alkynyl, $C_{3-6}$ cycloalkyl or $R^aR^bN$—, wherein heterocyclyl consisting of 5 ring atoms, heterocyclyl consisting of 6 ring atoms, heteroaryl consisting of 5 ring atoms, heteroaryl consisting of 6 ring atoms, $C_{1-4}$ alkyl, $C_{2-4}$ alkenyl, $C_{2-4}$ alkynyl, $C_{3-6}$ cycloalkyl are independently unsubstituted or substituted by 1, 2, 3 or 4 $R^v$;

$R^{10}$ is hydrogen, deuterium, $C_{1-4}$ alkyl or $C_{1-4}$ haloalkyl, or $R^{10}$, $R^1$ together with the nitrogen atom to which they are attached form a heterocyclic group consisting of 5 to 6 ring atoms, wherein $C_{1-4}$ alkyl or $C_{1-4}$ haloalkyl, heterocyclyl consisting of 5 to 6 ring atoms are unsubstituted or substituted by 1, 2, 3 or 4 substituents selected from —COOH, =O, tetrazolyl or $C_{1-4}$ alkyl-O—C(=O)—;

$R^2$ is hydrogen, deuterium, halogen, cyano, methyl, ethyl, n-propyl, isopropyl, n-butyl, isobutyl, n-pentyl, n-hexyl, methoxy, ethoxy, 1-propoxy, 2-propyloxy, 1-butoxy, 2-methyl-1-propoxy, 2-butoxy, 2-methyl-2-propoxy or 1-pentyloxy, wherein each of the methyl, ethyl, n-propyl, isopropyl, n-butyl, isobutyl, n-pentyl, n-hexyl, methoxy, ethoxy, 1-propoxy, 2-propyloxy, 1-butoxy, 2-methyl-1-propoxy, 2-butoxy, 2-methyl-2-propoxy or 1-pentyloxy is unsubstituted or substituted by 1, 2, 3 or 4 $R^w$;

wherein, each $R^a$, $R^b$, $R^v$ and $R^w$ has the meaning described in the present invention.

In other embodiments, $R^1$ is hydrogen, deuterium, F, Cl, Br, I, OH, —COOH, thiazolyl, tetrazolyl, methyl, ethyl, n-propyl, isopropyl, vinyl, propenyl, allyl, ethynyl, propynyl, cyclopropyl, cyclobutyl, cyclopentyl cyclohexyl or $R^aR^bN$—, wherein each of the thiazolyl, tetrazolyl, methyl, ethyl, n-propyl, isopropyl, vinyl, propenyl, allyl, ethynyl, propynyl, cyclopropyl, cyclobutyl, cyclopentyl and cyclohexyl is independently unsubstituted or substituted by 1, 2, 3 or 4 $R^v$;

$R^{10}$ is hydrogen, deuterium, methyl, ethyl, n-propyl, isopropyl or $C_{1-3}$ haloalkyl, or $R^{10}$ and $R^1$ together with the nitrogen atom to which they are attached form pyrrolidinyl, piperazinyl, piperidinyl or morpholinyl, wherein methyl, ethyl, n-propyl, isopropyl, $C_{1-3}$ haloalkyl, pyrrolidinyl, piperazinyl, piperidinyl or morpholinyl are unsubstituted or substituted by 1, 2, 3 or 4 substituents selected from —COOH, =O, tetrazolyl or $C_{1-3}$ alkyl-O—C(=O)—;

wherein $R^a$, $R^b$ and $R^v$ are as defined herein.

In some embodiments, $R^3$ is halogen, $C_{1-4}$ alkyl, $C_{2-4}$ alkenyl, $C_{2-4}$ alkynyl, $C_{3-6}$ cycloalkyl, heterocyclyl consisting of 3-6 ring atoms, phenyl, naphthyl, heteroaryl consisting of 5 or 6 ring atoms, wherein each of the $C_{1-4}$ alkyl, $C_{2-4}$ alkenyl, $C_{2-4}$ alkynyl, $C_{3-6}$ cycloalkyl, heterocyclyl consisting of 3-6 ring atoms, phenyl, naphthyl, heteroaryl consisting of 5 or 6 ring atoms is unsubstituted or substituted by 1, 2, 3 or 4 $R^x$;

wherein each $R^x$ is as defined herein.

In other embodiments, $R^3$ described herein is halogen, methyl, ethyl, n-propyl, isopropyl, n-butyl, isobutyl, vinyl, propenyl, allyl, ethynyl, propynyl, propargyl, cyclopropyl, cyclobutyl, cyclopentyl, cyclohexyl, azetidinyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholyl, piperazinyl, phenyl, naphthyl, furyl, pyrrolyl, pyridyl, pyrazolyl, imidazolyl, triazolyl, tetrazolyl, oxazolyl, isoxazolyl, oxadiazole, 1,3,5-triazinyl, thiazolyl, thienyl, pyrazinyl, pyridazinyl or pyrimidinyl, wherein each of the methyl, ethyl, n-propyl, isopropyl, n-butyl, isobutyl, vinyl, propenyl, allyl, ethynyl, propynyl, propargyl, cyclopropyl, cyclobutyl, cyclopentyl, cyclohexyl, azetidinyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholyl, piperazinyl, phenyl, naphthyl, furyl, pyrrolyl, pyridyl, pyrazolyl, imidazolyl, triazolyl, tetrazolyl, oxazolyl, isoxazolyl, oxadiazole, 1,3,5-triazinyl, thiazolyl, thienyl, pyrazinyl, pyridazinyl or pyrimidinyl is unsubstituted or substituted by 1, 2, 3 or 4 $R^x$;

wherein each $R^x$ is as defined herein.

In some embodimets, each $R^4$ and $R^5$ is independently hydrogen, deuterium, $C_{1-4}$ alkyl, $C_{1-4}$ alkylamino, $C_{1-4}$ alkoxy, $C_{2-4}$ alknyl, $C_{2-4}$ alkenyl, $C_{3-6}$ cycloalkyl or heterocyclyl consisting of 3 to 6 ring atoms, wherein each of the $C_{1-4}$ alkyl, $C_{1-4}$ alkylamino, $C_{1-4}$ alkoxy, $C_{2-4}$ alknyl, $C_{2-4}$ alkenyl, $C_{3-6}$ cycloalkyl or heterocyclyl consisting of 3 to 6 ring atoms is unsubstituted or substituted by 1, 2, 3 or 4 $R^y$;

or $R^4$, $R^5$ together with the carbon atom to which they are attached form cyclopropyl, cyclobutyl, cyclopentyl, cyclohexyl or heterocyclyl consisting of 3-6 ring atoms;

$R^6$ is hydrogen, deuterium, $C_{1-4}$ alkyl, $C_{2-4}$ alkenyl, $C_{3-6}$ cycloalkyl, heterocyclyl consisting of 3-6 ring atoms, phenyl, naphthyl, heteroaryl consisting of 5 or 6 ring atoms, wherein each of the $C_{1-4}$ alkyl, $C_{2-4}$ alkenyl, $C_{3-6}$ cycloalkyl, heterocyclyl consisting of 3-6 ring atoms, phenyl, naphthyl, heteroaryl consisting of 5 or 6 ring atoms is unsubstituted or substituted by 1, 2, 3 or 4 $R^z$;

each $R^7$, $R^8$ and $R^9$ is independently hydrogen, deuterium, F, Cl, Br, OH, cyano, $C_{1-4}$ alkyl, $C_{1-4}$ alkoxy, $C_{3-6}$ cycloalkyl, heterocyclyl consisting of 3 to 6 ring atoms, phenyl, naphthyl, heteroaryl consisting of 5 or 6 ring atoms, wherein each of the $C_{1-4}$ alkyl, $C_{1-4}$ alkoxy, $C_{3-6}$ cycloalkyl, heterocyclyl consisting of 3 to 6 ring atoms, phenyl, naphthyl, heteroaryl consisting of 5 or 6 ring atoms is unsubstituted or substituted by 1, 2, 3 or 4 $R^j$;

each $R^a$ and $R^b$ is independently hydrogen, deuterium, $C_{1-4}$ alkyl, alkoxy, $C_{2-4}$ alkenyl, $C_{2-4}$ alknyl, $C_{3-6}$ cycloalkyl, phenyl, naphthyl, heterocyclyl consisting of 3 to 6 ring atoms, heteroaryl consisting of 5 or 6 ring atoms, wherein each of the $C_{1-4}$ alkyl, alkoxy, $C_{2-4}$ alkenyl, $C_{2-4}$ alknyl, $C_{3-6}$ cycloalkyl, phenyl, naphthyl, heterocyclyl consisting of 3 to 6 ring atoms, heteroaryl consisting of 5 or 6 ring atoms is unsubstituted or substituted by 1, 2, 3 or 4 selected from F, Cl, Br, CN, OH, amino, $C_{1-4}$ alkyl, $C_{1-4}$ haloalkyl, $C_{1-4}$ alkoxy or $C_{1-4}$ alkylamino;

wherein $R^y$, $R^z$ and $R^j$ are as defined herein.

In other embodiments, each $R^4$ and $R^5$ is independently hydrogen, deuterium, methyl, ethyl, n-propyl, isopropyl, n-butyl, isobutyl, N-methylamino, N-ethylamino, N,N-dimethylamino, N,N-diethylamino, N-propylamino, methoxy, ethoxy, 1-propoxy, 2-propoxy, 1-butoxy, 2-methyl-1-propoxy, 2-butoxy, 2-methyl-2-propoxy, ethenyl, propenyl, allyl, ethynyl, propynyl, propargyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl or piperazinyl, wherein each of the methyl, ethyl, n-propyl, isopropyl, n-butyl, isobutyl, N-methylamino, N-ethylamino, N,N-dimethylamino, N,N-diethylamino, N-propylamino, methoxy, ethoxy, 1-propoxy, 2-propoxy, 1-butoxy, 2-methyl-1-propoxy, 2-butoxy, 2-methyl-2-propoxy, ethenyl, propenyl, allyl, ethynyl, propynyl, propargyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl or piperazinyl is unsubstituted or substituted by 1, 2, 3 or 4 $R^y$;

or $R^4$, $R^5$ together with the carbon atom to which they are attached form cyclopropyl, cyclobutyl, cyclopentyl, cyclohexyl, azetidinyl, oxetanyl, oxacyclopropyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl or piperazinyl;

$R^6$ is hydrogen, deuterium, methyl, ethyl, n-propyl, isopropyl, n-butyl, isobutyl, tert-butyl, vinyl, propenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of the methyl, ethyl, n-propyl, isopropyl, n-butyl, isobutyl, tert-butyl, vinyl, propenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl is unsubstituted or substituted by 1, 2, 3 or 4 $R^z$;

each $R^7$, $R^8$ and $R^9$ is independently hydrogen, deuterium, F, Cl, Br, OH, cyano, methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of the methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl is independently unsubstituted or substituted by 1, 2, 3 or 4 $R^j$;

each $R^a$ and $R^b$ is hydrogen, deuterium, methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, vinyl, propenyl, ethynyl, propynyl, propargyl, cyclopropyl, cyclobutyl, cyclopentyl, cyclohexyl, phenyl, naphthyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, vinyl, propenyl, ethynyl, propynyl, propargyl, cyclopropyl, cyclobutyl, cyclopentyl, cyclohexyl, phenyl, naphthyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl is independently unsubstituted or substituted by 1, 2, 3 or 4 substituents selected from F, Cl, Br, CN, OH, amino, $C_{1-3}$ alkyl, $C_{1-3}$ haloalkyl, $C_{1-3}$ alkoxy or $C_{1-3}$ alkylamino;

wherein $R^y$, $R^z$ and $R^j$ are as defined herein.

In some embodiments, each $R^v$, $R^w$, $R^y$, $R^z$ and $R^j$ is independently deuterium, F, Cl, Br, CN, =O, OH, —COOH, amino, $C_{1-4}$ alkyl, $C_{1-4}$ alkoxy, $C_{1-4}$ alkylthio, $C_{1-4}$ alkylamino, $C_{2-4}$ alkenyl, $C_{2-4}$ alknyl, $C_{3-6}$ cycloalkyl, heterocyclyl consisting of 3 to 6 ring atoms, phenyl, naphthyl, heteroaryl consisting of 5 or 6 ring atoms, wherein each of the amino, $C_{1-4}$ alkyl, $C_{1-4}$ alkoxy, $C_{1-4}$ alkylthio, $C_{1-4}$ alkylamino, $C_{2-4}$ alkenyl, $C_{2-4}$ alknyl, $C_{3-6}$ cycloalkyl, heterocyclyl consisting of 3 to 6 ring atoms, phenyl, naphthyl, heteroaryl consisting of 5 or 6 ring atoms is independently unsubstitued or substituted by 1, 2, 3, or 4 $R^e$;

wherein each $R^e$ is as defined herein.

In other embodiments, each of $R^v$, $R^w$, $R^y$, $R^z$ and $R^j$ is independently deuterium, F, Cl, Br, CN, =O, OH, —COOH, amino, methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, $C_{1-3}$ alkylthio, N-methylamino, N-ethylamino, N,N-dimethylamino, N,N-diethylamino, N-propylamino, vinyl, propylene, ethynyl, propynyl, propargyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of the amino, methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, $C_{1-3}$ alkylthio, N-methylamino, N-ethylamino, N,N-dimethylamino, N,N-diethylamino, N-propylamino, vinyl, propylene, ethynyl, propynyl, propargyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl is unsubstituted or substituted by 1, 2, 3 or 4 $R^e$;

wherein each $R^e$ is as defined herein.

In some embodiments, each R is independently deuterium, F, Cl, Br, CN, =O, OH, —COOH, amino, $C_{1-6}$ alkyl, $C_{1-6}$ alkoxy, $C_{1-6}$ alkylthio, $C_{1-6}$ alkylamino, $C_{2-4}$ alkenyl, $C_{2-4}$ alkynyl, $C_{3-6}$ cycloalkyl, heterocyclyl consisting of 3 to 6 ring atoms, phenyl, naphthyl, heteroaryl consisting of 5 to 6 atoms or -L-$R^{11}$, wherein each of the amino, $C_{1-6}$ alkyl, $C_{1-6}$ alkoxy, $C_{1-6}$ alkylthio, $C_{1-6}$ alkylamino, $C_{2-4}$ alkenyl, $C_{2-4}$ alkynyl, $C_{3-6}$ cycloalkyl, heterocyclyl consisting of 3 to 6 ring atoms, phenyl, naphthyl and heteroaryl consisting of 5 to 6 atoms is unsubstituted or substituted by 1, 2, 3 or 4 $R^f$;

wherein each $R^f$ is as defined herein.

In other embodiments, each of $R^v$, $R^w$, $R^y$, $R^z$ and $R^j$ is independently deuterium, F, Cl, Br, CN, =O, OH, —COOH, amino, methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, $C_{1-3}$ alkylthio, N-methylamino, N-ethylamino, N,N-dimethylamino, N,N-diethylamino, N-propylamino, vinyl, propylene, ethynyl, propynyl, 1-propynyl, cyclopropyl, cyclobutyl, cyclopentyl, cyclohexyl, azacyclobutyl, oxetanyl, oxacyclopropyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl or -L-$R^{11}$, wherein each of the amino, methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, $C_{1-3}$ alkylthio, N-methylamino, N-ethylamino, N,N-dimethylamino, N,N-diethylamino, N-propylamino, vinyl, propylene, ethynyl, propynyl, 1-propynyl, cyclopropyl, cyclobutyl, cyclopentyl, cyclohexyl, azacyclobutyl, oxetanyl, oxacyclopropyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is unsubstituted or substituted by 1, 2, 3 or 4 $R^f$;

wherein each $R^f$ is as defined herein.

In other embodiments, each $R^x$ is independently deuterium, F, Cl, Br, CN, =O, —COOH, amino, methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, $CH_3—S(=O)_2—$, $CH_3CH_2—S(=O)_2—$, $CH_3CH_2CH_2—S(=O)_2—$, $(CH_3)_2CH—S(=O)_2—$, N-methylamino, N-ethylamino, N,N-dimethylamino, N,N-diethylamino, N-propylamino, vinyl, propenyl, ethynyl, propynyl, 1-propynyl, cyclopropyl, cyclobutyl, cyclopentyl, cyclohexyl, azetidinyl, oxobutyl, oxopropyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl or -L-$R^{11}$, wherein amino, methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, $CH_3—S(=O)_2—$, $CH_3CH_2—S(=O)_2—$, $CH_3CH_2CH_2—S(=O)_2—$, $(CH_3)_2CH—S(=O)_2—$, N-methylamino, N-ethylamino, N,N-dimethylamino, N,N-diethylamino, N-propylamino, vinyl, propenyl, ethynyl, propynyl, 1-propynyl, cyclopropyl, cyclobutyl, cyclopentyl, cyclohexyl, azetidinyl, oxobutyl, oxopropyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl is independently unsubstituted or substituted by 1, 2, 3 or 4 $R^f$;

wherein each $R^f$ is as defined herein.

In some embodiments, $R^{11}$ is $C_{1-4}$ alkyl, $C_{1-4}$ alkoxy, $C_{3-6}$ cycloalkyl, heterocyclyl consisting of 3 to 6 ring atoms, phenyl, naphthyl or heteroaryl consisting of 5 to 6 ring atoms, wherein each of the $C_{1-4}$ alkyl, $C_{1-4}$ alkoxy, $C_{3-6}$ cycloalkyl, heterocyclyl consisting of 3 to 6 ring atoms, phenyl, naphthyl and heteroaryl consisting of 5 to 6 ring atoms is independently unsubstituted or substituted by 1, 2, 3 or 4 $R^h$;

wherein each $R^h$ is as defined herein.

In other embodiments, $R^{11}$ is methyl, ethyl, n-propyl, isopropyl, methoxy, ethoxy, 1-propoxy, 2-propoxy, 1-butoxy, 2-methyl-1-propoxy, 2-butoxy, cyclopropyl, cyclobutyl, cyclopentyl, cyclohexyl, azetidinyl, oxetanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of the methyl, ethyl, n-propyl, isopropyl, methoxy, ethoxy, 1-propoxy, 2-propoxy, 1-butoxy, 2-methyl-1-propoxy, 2-butoxy, cyclopropyl, cyclobutyl, cyclopentyl, cyclohexyl, azetidinyl, oxetanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3 or 4 $R^h$;

wherein each $R^h$ is as defined herein.

In some embodiments, each $R^e$, $R^g$ and $R^h$ is independently selected from F, Cl, Br, CN, OH, =O, —COOH, —C(=O)O$C_{1-4}$ alkyl, —S(=O)$_2$—$C_{1-4}$ alkyl, —S(=O)$_2$-cyclopropyl, —S(=O)$_2$-cyclobutyl, —S(=O)$_2$-cyclopentyl, —S(=O)$_2$-cyclohexyl, amino, $C_{1-4}$ alkyl, $C_{1-4}$ haloalkyl, $C_{1-4}$ alkoxy, $C_{1-4}$ alkylthio, $C_{1-4}$ haloalkoxy, $C_{1-6}$ alkylamino, $C_{2-4}$ alkenyl, $C_{2-4}$ alkynyl, phenyl, naphthyl, $C_{3-6}$ cycloalkyl, heteroaryl consisting of 5 or 6 ring atoms, heterocyclyl consisting of 5 or 6 ring atoms, $C_{1-4}$ alkoxy $C_{1-3}$ alkylene or $C_{1-4}$ alkylamino $C_{1-3}$ alkylene;

$R^{12}$ is hydrogen, deuterium, $C_{1-4}$ alkyl or $C_{1-4}$ haloalkyl.

In other embodiments, each R, $R^f$, R and $R^h$ is independently selected from F, Cl, Br, CN, OH, =O, —COOH, —C(=O)O-methyl, —C(=O)O-ethyl, —C(=O)O-n-propyl, —C(=O)O-isopropyl, —C(=O)O-n-butyl, —C(=O)O-isobutyl, —C(=O)O-sec-butyl, —C(=O)O-tert-butyl, —S(=O)$_2$-methyl, —S(=O)$_2$-ethyl, —S(=O)$_2$-n-propyl, —S(=O)$_2$-isopropyl, —S(=O)$_2$-n-butyl, —S(=O)$_2$-isobutyl, —S(=O)$_2$-sec-butyl, —S(=O)$_2$-tert-butyl, —S(=O)$_2$-cyclopropyl, —S(=O)$_2$-cyclobutyl, —S(=O)$_2$-cyclopentyl, —S(=O)$_2$-cyclohexyl, amino, methyl, ethyl, n-propyl, isopropyl, n-butyl, isobutyl, $C_{1-3}$ haloalkyl, methoxy, ethoxy, 1-propoxy, 2-propoxy, 1-butoxy, 2-methyl-1-propoxy, 2-butoxy, $C_{1-3}$ alkylthio, $C_{1-3}$ haloalkoxy, N-methylamino, N-ethylamino, N, N-dimethylamino, N,N-diethylamino, N-propylamino, vinyl, propenyl, ethynyl, propynyl, propargyl, phenyl, naphthyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, $C_{1-3}$ alkoxy $C_{1-2}$ alkylene or $C_{1-3}$ alkylamino $C_{1-2}$ alkylene; $R^{12}$ is hydrogen, deuterium, $C_{1-3}$ alkyl or $C_{1-3}$ haloalkyl.

In some embodiments, provided herein is a compound having one of the following structures, or a stereoisomer, a tautomer, an N-oxide, a hydrate, a metabolite, a pharmaceutically acceptable salt or a prodrug thereof, but not limited to these compounds:

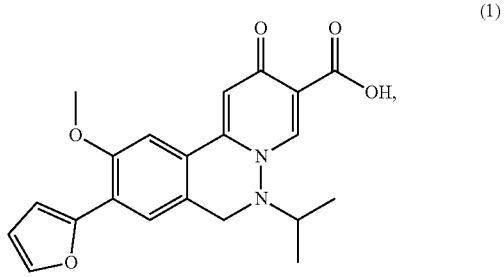

(1)

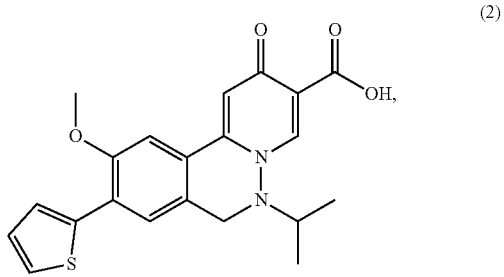

(2)

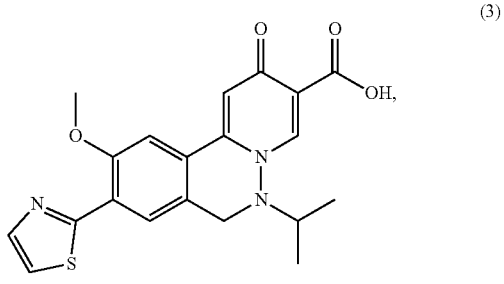

(3)

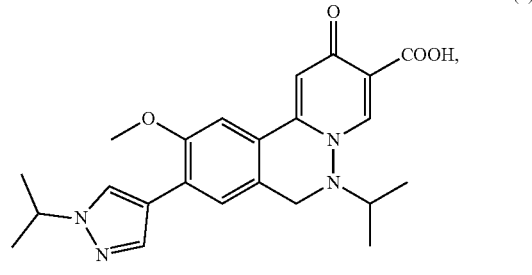

(4)

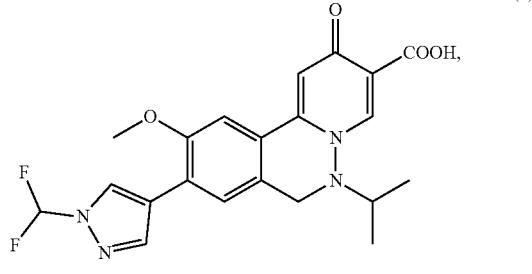

(5)

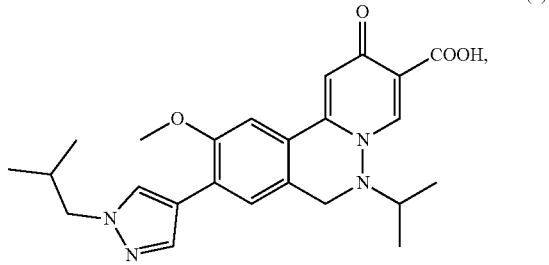

(6)

-continued
(7)
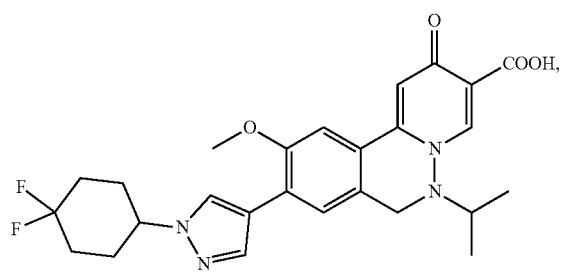
(8)
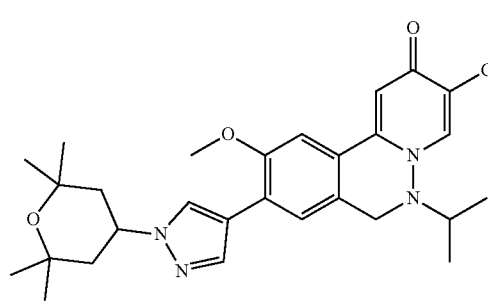
(9)
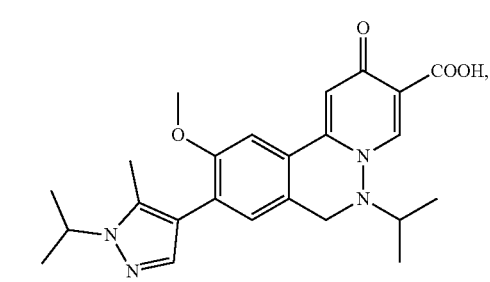
(10)
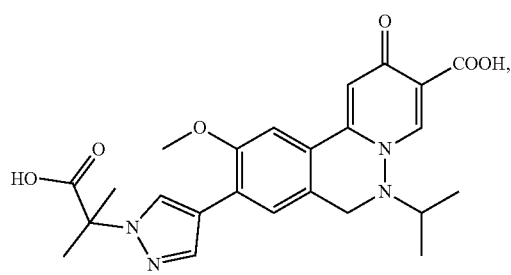
(11)
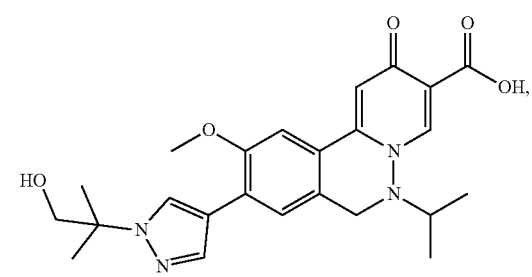
-continued
(12)
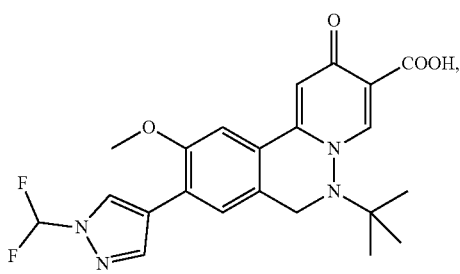
(13)
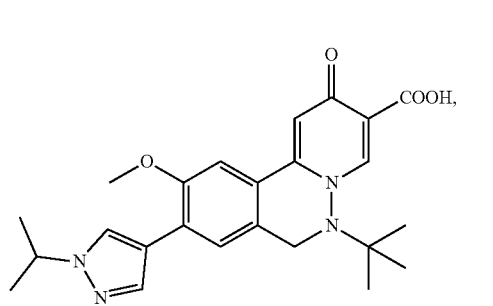
(14)
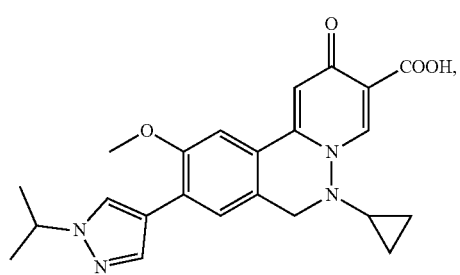
(15)
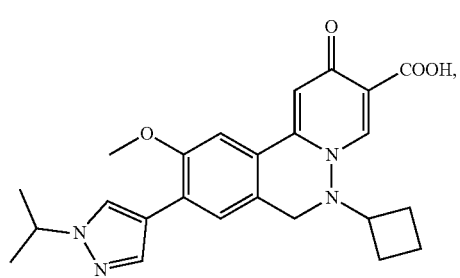
(16)
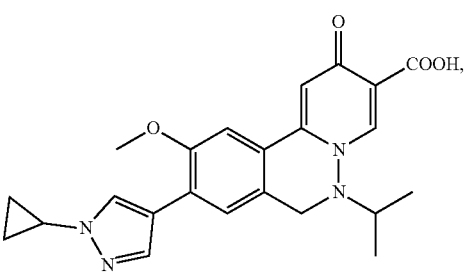

-continued
(17)
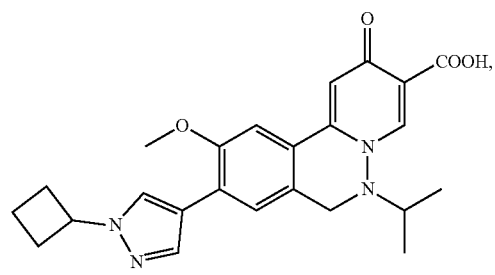
(18)
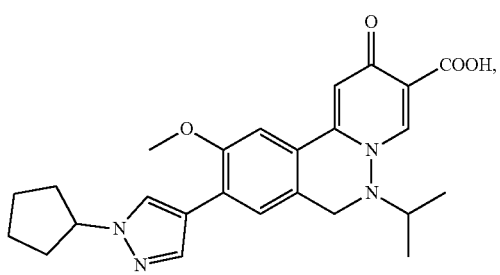
(19)
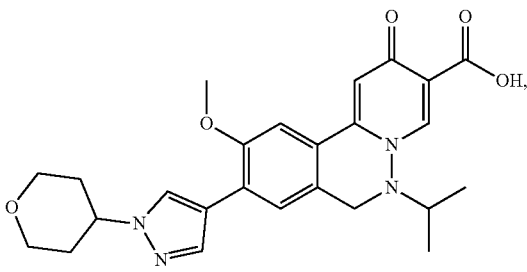
(20)
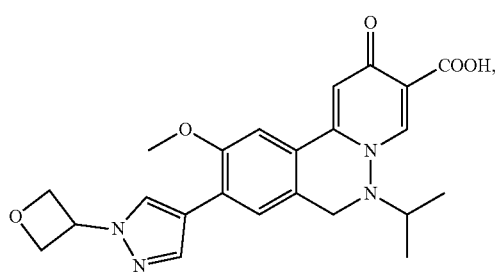
(21)
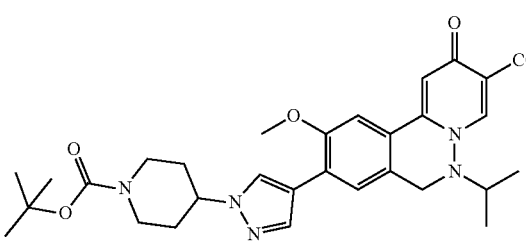
-continued
(22)
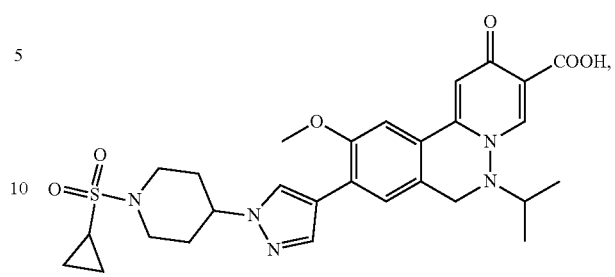
(23)
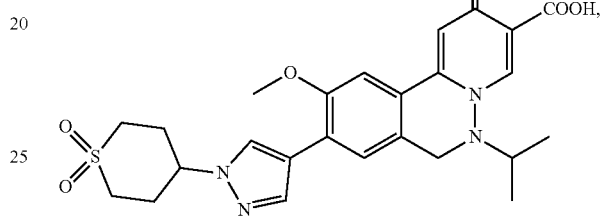
(24)
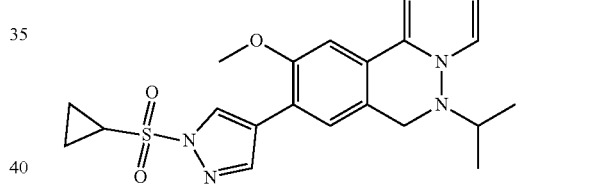
(25)
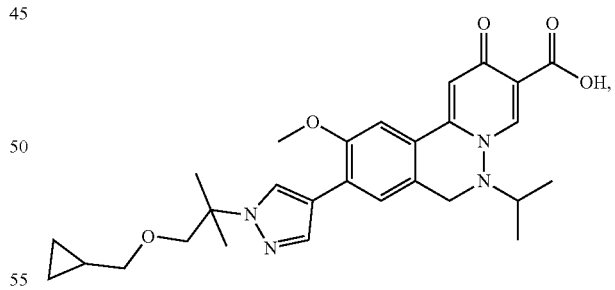
(26)
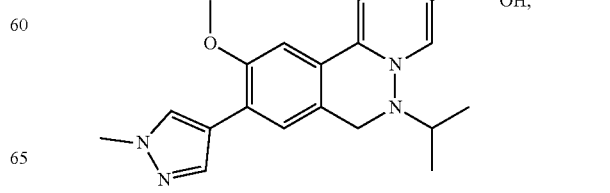

(27)
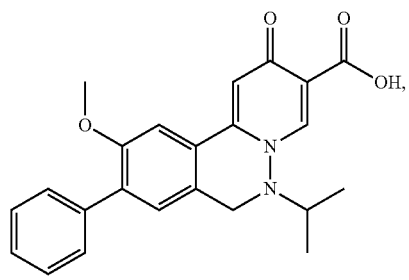
(28)
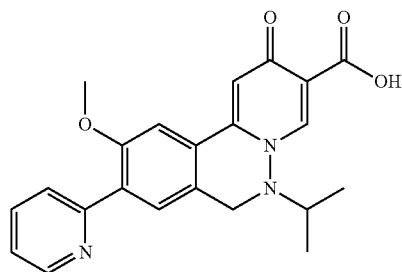
(29)
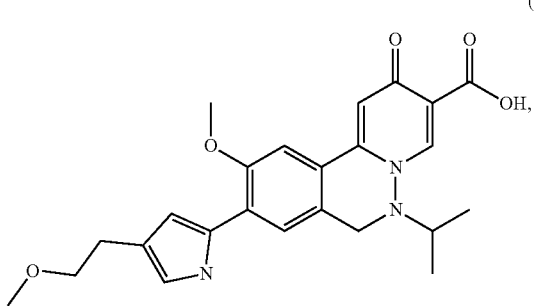
(30)
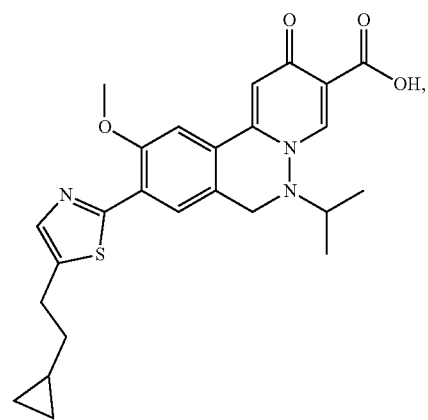
(31)
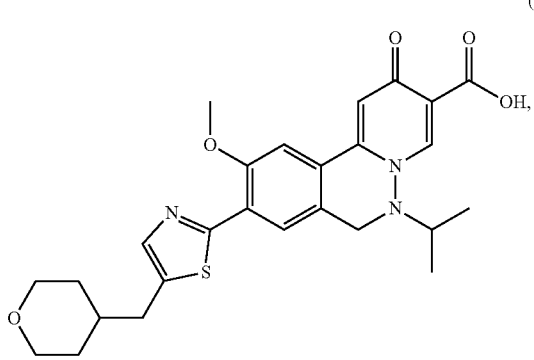
(32)
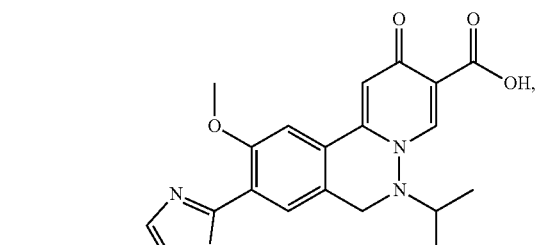
(33)
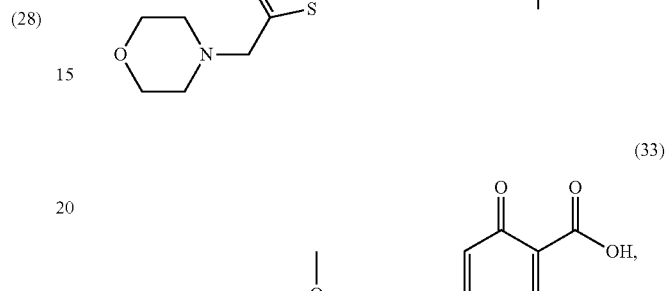
(34)
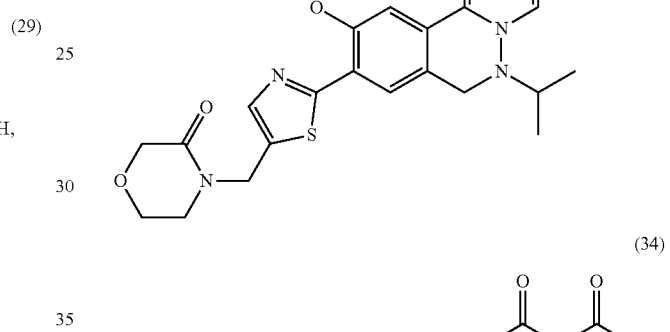
(35)
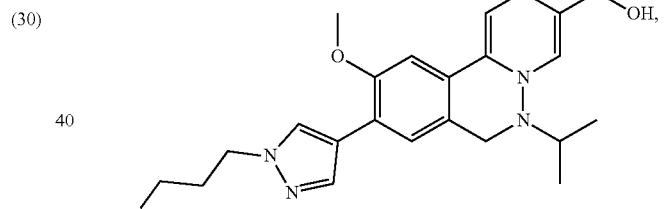
(36)
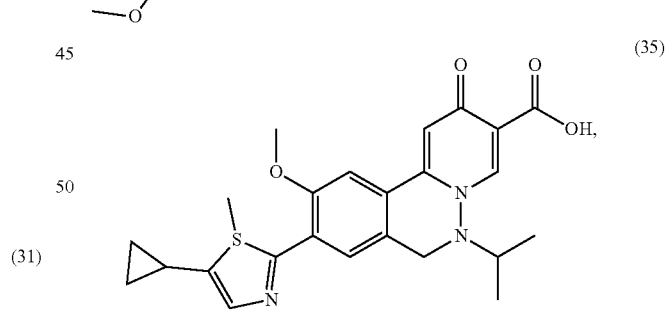

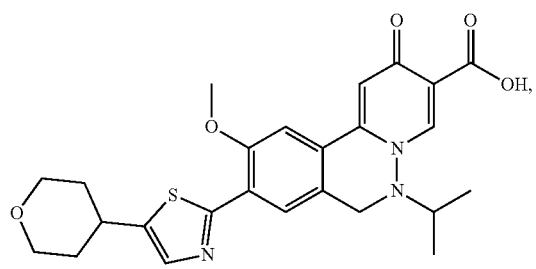
(37)
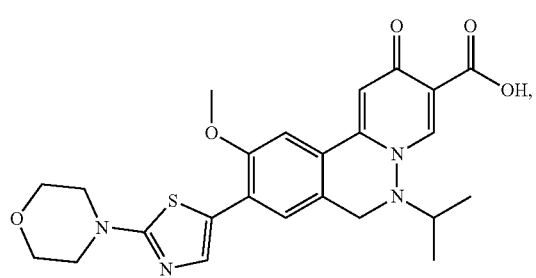
(38)
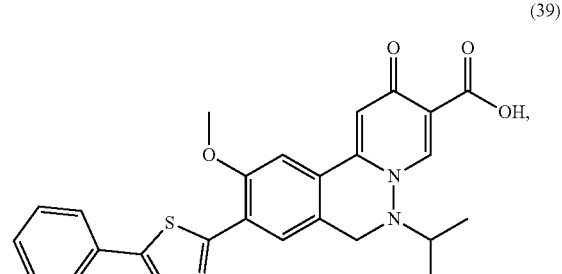
(39)
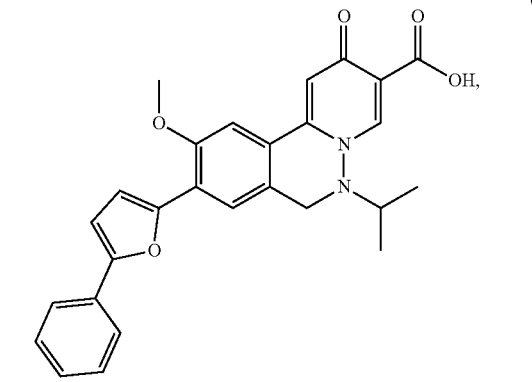
(40)
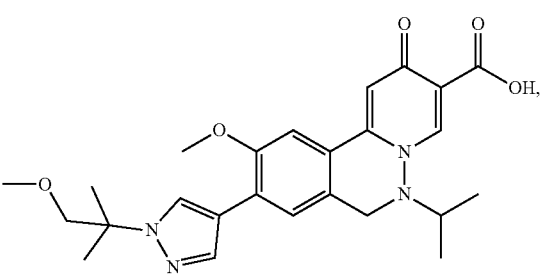
(41)
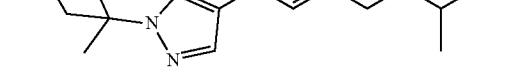
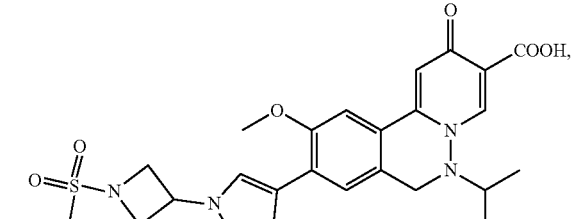
(42)
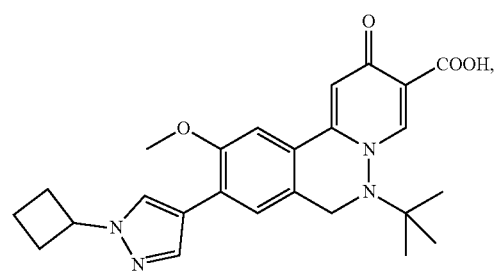
(43)
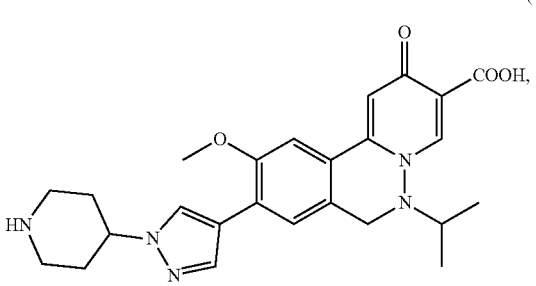
(44)
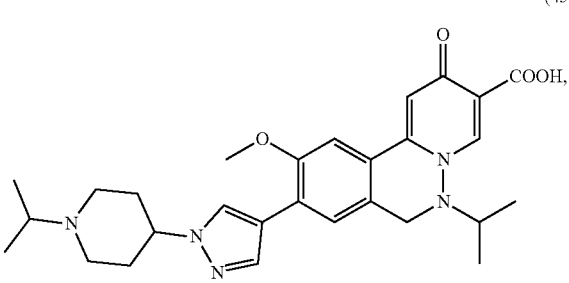
(45)
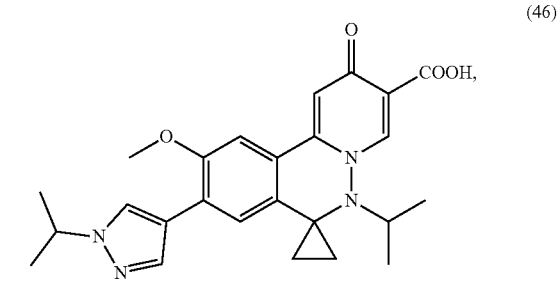
(46)

(47) 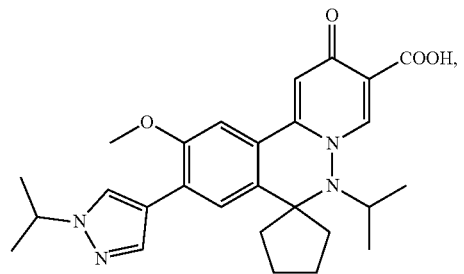
(48) 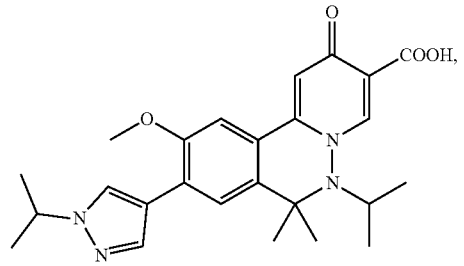
(49) 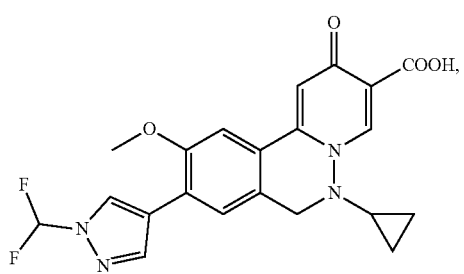
(50) 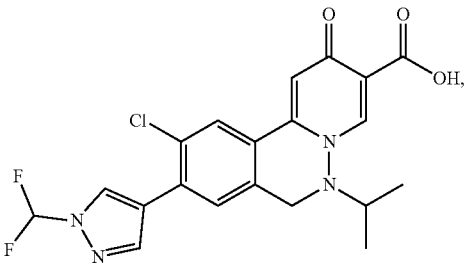
(51) 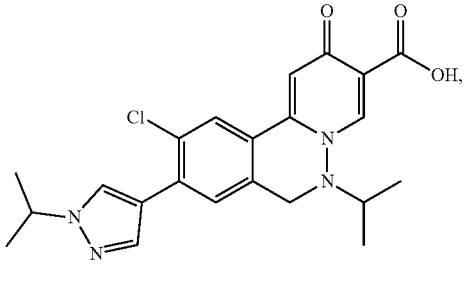
(52) 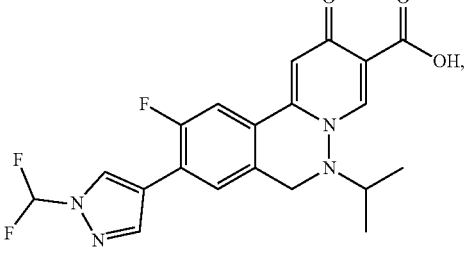
(53) 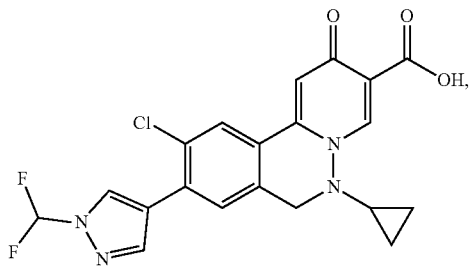
(54) 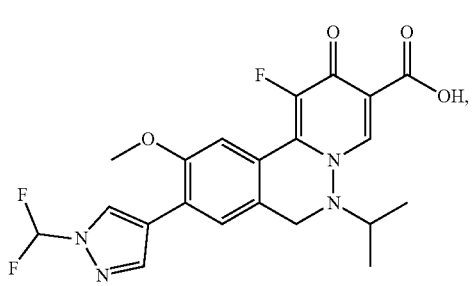
(55) 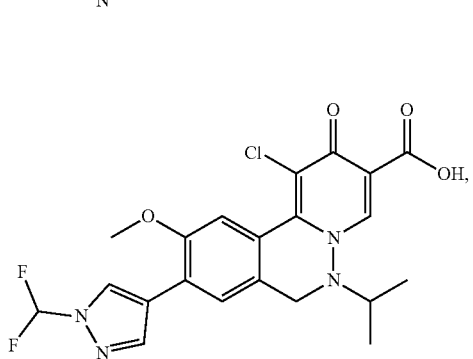
(56) 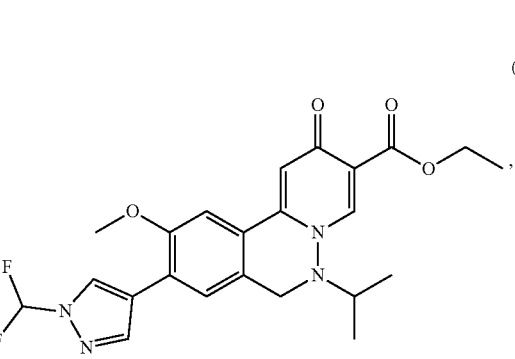
(57) 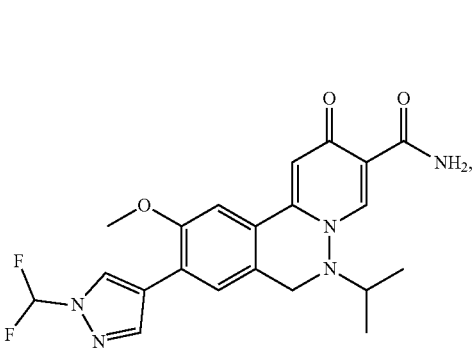

-continued

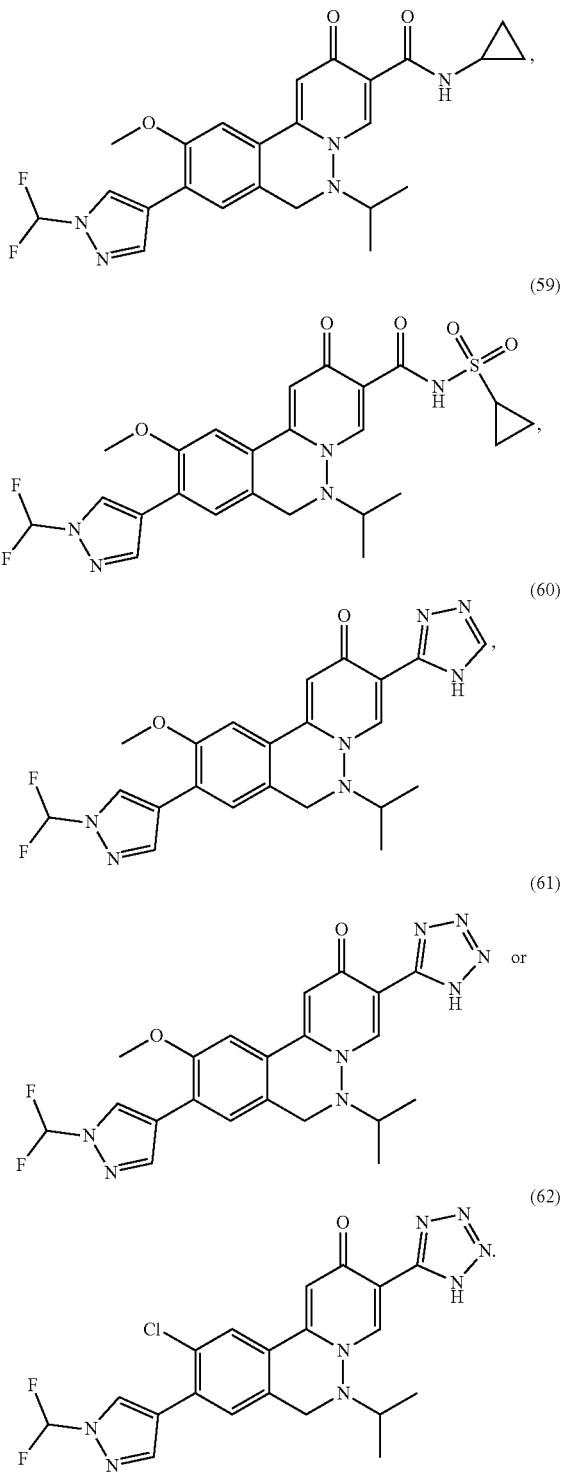

Unless otherwise specified, a compound having Formula (I) or a stereoisomer, a tautomer, an N-oxide, a solvate, a metabolite, a pharmaceutically acceptable salt or a prodrug thereof, are all embraced within the scope of the invention.

In other aspect, the invention also provides a pharmaceutical composition comprising a compound of the invention, optionally further comprising a pharmaceutically acceptable excipient or a combination of said excipients.

In some embodiments, the pharmaceutical compositions of the present invention further comprise other anti-HBV drugs.

In some embodiments, the pharmaceutical compositions of the present invention, wherein the anti-HBV drugs is a HBV polymerase inhibitor, an immunomodulator or an interferon.

In other embodiments, the pharmaceutical composition of the present invention, wherein the anti-HBV drug is lamivudine, telbivudine, Tenofovir Disoprox, entecavir, adefovir dipivoxil, Alfaferone, Alloferon, Celmoleukin, Clevudine, emtricitabine, famciclovir, interferon, HepaTect CP, intefen, interferon α-1b, interferon α, interferon α-2a, interferon β-1a, interferon α-2, interleukin-2, mivotilate, nitazoxanide, peginterferon α-2a, ribavirin, interferon-A, Sizofiran, Euforavac, Ampligen, Phosphazid, Heplisav, interferon α-2b, levamisole or Propagermanium.

In other aspect, provided herein is use of the compound or the pharmaceutical composition disclosed herein in the manufacture of a medicament for preventing treating or reducing viral diseases.

In some embodiments, the use of the invention, wherein the viral disease is Hepatitis B virus infection or a disease caused by Hepatitis B virus infection.

In other embodiments, the use of the invention, wherein the disease caused by Hepatitis B virus infection is cirrhosis or hepatocellular carcinoma.

In other aspect, provided herein is use of the compound or the pharmaceutical composition disclosed herein in the manufacture of a medicament for inhibiting the formation or secretion of HBsAg and/or inhibiting the formation or replication of HBV DNA.

In other aspect, provided herein is use of the compound or the pharmaceutical composition disclosed herein in the manufacture of a medicament for preventing, treating or reducing Hepatitis B disease.

Another aspect of the invention relates to a method of preventing treating or ameliorating a patient's HBV disorder, the method comprising administering to a patient a pharmaceutically acceptable effective amount of a compound of the invention.

Another aspect of the invention relates to a method of preventing treating or ameliorating a patient's HBV disorder, the method comprising administering to a patient a pharmaceutically acceptable effective amount of pharmaceutical compositions containing compounds of the present invention.

In other aspect, provided herein is use of the compound disclosed herein in the manufacture of a medicament for preventing managing or treating HBV disease and lessening the severity thereof.

In other aspect, provided herein is use of the pharmaceutical composition containing compounds of the present invention in the manufacture of a medicament for preventing, managing or treating HBV disease and lessening the severity thereof.

In other aspect, the invention relates to a method for inhibiting HBV infection. The method comprises contacting cells with the compounds or compositions of the invention which can effectively inhibit the dose contact of HBV In still other embodiments, the method further comprises contacting the cells with an anti-HBV agent.

Another aspect of the invention relates to a method of treating a patient with HBV disease, the method comprising administering to the patient a therapeutically effective amount of a compound of the invention or a composition thereof. In other embodiments, the method further comprises administering another HBV treatment.

Another aspect of the invention relates to a method of inhibiting HBV infection in a patient, the method comprising administering to the patient a therapeutically effective amount of a compound of the invention or a composition thereof. In other embodiments, the method further comprises other administration of HBV treatments.

In other aspect, provided herein is a method of preparing, separating or purifying the compound of Formula (I).

The present invention also comprises uses of the compound and pharmaceutically acceptable salts thereof in the manufacture of a medicament for effectively inhibiting HBV infection including those described in the invention. The compound disclosed herein also can be used in the manufacture of a medicament for lessening, preventing, managing or treating patients with hepatitis B. The present invention provides a pharmaceutical composition comprising the compound of Formula (I), and at least one of pharmaceutically acceptable excipients.

The present invention also provides a method of effectively inhibiting HBV infection, or sensitive to these diseases in a patient comprising administering to the patient a therapeutically effective amount of the compound of Formula (I).

Unless otherwise stated, all stereoisomers, tautomers, N-oxides, solvates, metabolites, salts and pharmaceutically acceptable prodrugs of the compounds disclosed herein are within the scope of the invention.

In certain embodiments, the salt is a pharmaceutically acceptable salt. The phrase "pharmaceutically acceptable" refers to that the substance or composition must be compatible chemically and/or toxicologically, with the other ingredients comprising a formulation, and/or the mammal being treated therewith.

The salt of the compound of the present invention further includes an intermediate for preparing or purifying the compound of the formula (I) or a salt of the formula (I) or an isomer thereof but not necessarily a pharmaceutically acceptable salt.

The term "pharmaceutically acceptable" refers to a material that is acceptable for pharmaceutical use and does not adversely interact with the active ingredient from toxicology of view.

If the compound of the invention is basic, the desired salt can be prepared by any suitable method provided in the literature, for example, using inorganic acids such as hydrochloric acid, hydrobromic acid, sulfuric acid, nitric acid, and phosphoric acid, etc.; or using organic acids such as acetic acid, maleic acid, succinic acid, mandelic acid, fumaric acid, malonic acid, pyruvic acid, malic acid, 2-hydroxypropionic acid, citric acid, oxalic acid, glycolic acid and salicylic acid; a pyranosidyl acid, such as glucuronic acid and galacturonic acid; an alpha-hydroxy acid, such as citric acid and tartaric acid; an amino acid, such as aspartic acid and glutamic acid; an aromatic acid, such as benzoic acid and cinnamic acid; a sulfonic acid, such as p-toluenesulfonic acid, benzenesulfonic acid, methanesulfonic acid, ethanesulfonic acid, trifluoromethanesulfonic acid, and the like; or the combination thereof.

If the compound of the present invention is acidic, the desired salt can be obtained by a suitable method, with an inorganic base, such as a lithium, sodium, potassium, calcium, magnesium, aluminum, iron, ferrous, manganese, manganese, copper, zinc and ammonium salts of a compound of the formula (I), etc.; with an inorganic base, such as a salt of a compound of the formula (I) with methylamine, dimethylamine, trimethylamine, ethylamine, diethylamine, triethylamine, tromethamine, diethylaminoethanol, isopropylamine, 2-ethylaminoethanol, pyridine, picoline, ethanolamine, diethanolamine, ammonium, dimethylethanolamine, tetramethylammonium, tetraethylammonium, triethanolamine, piperidine, piperazine, morpholine, imidazolium, lysine, arginine, L-arginine, histidine, N-methylglucamine, dimethyl glucosamine, ethyl glucosamine, dicyclohexylamine, hexamethylenediamine, ethylenediamine, glucosamine, sarcosine, serinol, aminopropanediol, 1-amino-2,3,4-butanetriol, L-lysine, ornithine, etc.

Pharmaceutical Compositions, Formulations, Administration and Uses of the Compounds and Composition Thereof The invention features pharmaceutical compositions that include a compound of Formula (I) or a compound named in Examples, or a stereoisomer, a tautomer, an N-oxide, a solvate, a metabolite, a pharmaceutically acceptable salt or a prodrug thereof, and a pharmaceutically acceptable excipient. Chronic viral diseases caused by HBV may lead to serious disease. Chronic hepatitis B virus infection can lead to cirrhosis and/or hepatocellular carcinogenesis in many cases. The compound in the composition of the present invention can effectively inhibit hepatitis B virus and is suitable for the treatment of diseases caused by viruses, especially acute and chronic persistent HBV infection.

For the compounds of the invention, the indicated regions that may be mentioned are, for example, the treatment of acute and chronic viral infections that may result in infectious hepatitis, for example, hepatitis B virus infection. The compounds of the invention are especially suitable for the treatment of acute and chronic hepatitis B virus infection.

The invention includes a pharmaceutical preparation comprising, in addition to a non-toxic, inert, pharmaceutically suitable excipient, one or more compounds (I) or compositions of the invention.

The above pharmaceutical preparation may also contain other active pharmaceutical ingredients other than the compound (I).

It will also be appreciated that certain of the compounds disclosed herein can exist in free form for treatment, or where appropriate, as a pharmaceutically acceptable derivative thereof. Some non-limiting examples of the pharmaceutically acceptable derivative include pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

As described above, the pharmaceutical compositions comprising any one of the compounds of the invention further comprise a pharmaceutically acceptable excipients, such as solvents, solid excipients, diluents, binders, disintegrating agents, or other liquid excipients, dispersing agents, flavoring or suspending agents, surfactants, isotonic agents, thickening agents, emulsifiers, preservative, solid binder or lubricant, as suited to the particular dosage form desired. As described in the following: In Remington: Troy et al., Remington: The Science and Practice of Pharmacy, 21st ed., 2005, Lippincott Williams & Wilkins, Philadelphia, and Swarbrick et al., Encyclopedia of Pharmaceutical Technology, eds. 1988-1999, Marcel Dekker, New York, both of which are herein incorporated by reference in their entireties, discloses various excipients used in formulating pharmaceutically acceptable compositions and known techniques for the preparation thereof. Except insofar as any conventional excipients incompatible with the compounds disclosed herein, such as by producing any undesirable biological effect or otherwise interacting in a deleterious manner with any other components of the pharmaceutically acceptable composition, its use is contemplated to be within the scope of this invention.

Some non-limiting examples of materials which can serve as pharmaceutically acceptable excipients include ion exchanger; aluminum; alumina; aluminum stearate; lecithin; serum protein such as human serum albumin; buffer substance such as phosphate; glycine; sorbic acid; potassium sorbate; partial glyceride mixture of saturated vegetable fatty acid; water; salt or electrolyte such as protamine sulfate, disodium hydrogen phosphate, potassium hydrogen phosphate, sodium chloride and zinc salt; colloidal silica; magnesium trisilicate; polyvinyl pyrrolidone; polyacrylate; waxe; polyethylene-polyoxypropylene-block polymer; wool fat; sugar such as lactose, glucose and sucrose; starch such as corn starch and potato starch; cellulose and its derivative such as sodium carboxymethyl cellulose, ethyl cellulose and cellulose acetate; powdered tragacanth; malt; gelatin; talc; excipients such as cocoa butter and suppository waxes; oil such as peanut oil, cottonseed oil, safflower oil, sesame oil, olive oil, corn oil and soybean oil; glycol such as propylene glycol and polyethylene glycol; ester such as ethyl oleate and ethyl laurate; agar; buffering agent such as magnesium hydroxide and aluminum hydroxide; alginic acid; pyrogen-free water; isotonic saline; Ringer's solution; ethyl alcohol and phosphate buffer solution, as well as other non-toxic compatible lubricant such as sodium lauryl sulfate and magnesium stearate, coloring agent, releasing agent, coating agent, sweetening, flavoring and perfuming agent, preservative and antioxidant.

The pharmaceutical composition of the compound of the present invention can be administered in any of the following aspects: oral administration, spray inhalation, topical administration, rectal administration, nasal administration, vaginal administration, parenteral administration such as subcutaneous, intravenous, intramuscular, intraperitoneal, intrapulmonary, intrathecal, intraventricular, intrasternal, or intracranial injection or infusion, or by means of an explanted reservoir. The preferred modes of administration are administered orally, intraperitoneally or intravenously.

The compound of the invention or a pharmaceutically acceptable composition may be administered in unit dosage form. The dosage form can be a liquid dosage form or a solid dosage form. Liquid dosage forms can be true solutions, colloids, microparticulates, suspensions. Other dosage forms such as tablets, capsules, dropping pills, aerosols, pills, powders, solutions, suspensions, emulsions, granules, suppositories, lyophilized powders, inclusions, implants, patches, wipes agents, etc.

Oral tablets and capsules may contain excipients such as binders such as syrup, acacia, sorbitol, tragacanth, or polyvinylpyrrolidone; fillers such as lactose, sucrose, corn starch, calcium phosphate, sorbitol, glycine; lubricants such as magnesium stearate, talc, polyethylene glycol, silica; disintegrants such as potato starch; or acceptable humectants such as sodium lauryl sulfate. Tablets can be coated by methods known in the pharmacy.

The oral solution can be made into a suspension of water and oil, a solution, an emulsion, a syrup or a tincture, or it can be made into a dry product, supplemented with water or other suitable medium before use. This liquid preparation may contain conventional additives, such as suspending agent, sorbitol, cellulose methyl ether, glucose syrup, gel, hydroxyethyl cellulose, carboxymethyl cellulose, aluminum stearate gel, hydrogenated edible oil; emulsifier, such as lecithin, sorbitol Sugar monooleate; or non-aqueous accessories (may contain edible oils) such as almond oil; grease such as glycerin, glycol or ethanol; preservatives such as methyl or propyl paraben, sorbic acid. Flavors or colorants are added if needed.

Suppositories may contain conventional suppository bases such as cocoa butter or other glycerides.

For parenteral administration, liquid dosage forms are usually made of a compound and a sterile excipient. Water is preferred for excipients. Depending on the selected excipient and drug concentration, the compound can be dissolved in the excipient and also can be made into the suspension. In the preparation of the injectable solution, the compound is dissolved in water, filtered and sterilized, and then placed in a sealed bottle or ampoule.

When applied topically to the skin, the compounds of the invention may be formulated in the form of a suitable ointment, lotion, or cream, wherein the active ingredient is suspended or dissolved in one or more excipients, wherein excipients that can be used in ointment preparations include, but are not limited to, mineral oil, liquid petroleum jelly, white petrolatum, propylene glycol, polyethylene oxide, polypropylene oxide, emulsifying wax and water; adjuvants for lotions and creams include, but are not limited to, mineral oil, sorbitan monostearate, Tween 60, cetyl esters wax, hexadecene aryl alcohol, 2-octyldodecanol, benzyl alcohol and water.

In general, it has proven to be advantageous if the total amount of active compound administered according to the invention is from about 0.01 to 500 mg/kg body weight per 24 hours, whether in human or veterinary medicine, preferably 0.01-100 mg/kg. If appropriate, multiple doses are administered in multiple doses to achieve the desired effect. The amount of the active compound contained in a single dose is preferably from about 1 to 80 mg/kg body weight, more preferably from 1 to 50 mg/kg body weight, but may not be in accordance with the above-mentioned dosage, that is, depending on the type and weight of the subject, the nature and severity of the disease, type of formulation and mode of administration of the drug, as well as dosing cycle or time interval.

The pharmaceutical composition provided by the invention further comprises anti-HBV drugs. Wherein anti-HBV drugs are HBV polymerase inhibitors, immunomodulators, interferons or other novel anti-HBV agents such as HBV RNA replication inhibitors, HBsAg secretion inhibitors, HBV capsid inhibitors, antisense oligomers, siRNA, HBV therapeutic vaccine, HBV preventive vaccine, HBV antibody therapy (monoclonal or polyclonal), and agonists for the treatment or prevention of HBV Anti-HBV drugs have lamivudine, telbivudine, Tenofovir Disoprox, entecavir, Adefovir Dipivoxil Tablets, Alfaferone, Alloferon, Celmoleukin, Clevudine, emtricitabine, famciclovir, interferon, HepaTect CP, intefen, interferon $\alpha$-1b, interferon $\alpha$, interferon $\alpha$-2a, interferon $\beta$-1a, interferon $\alpha$-2, interleukin-2, mitoxetate, nitazoxanide, peginterferon $\alpha$-2a, ribavirin, Roferon-A, Sizofiran, Euforavac, Ampligen, Phosphazid, Heplisav, interferon $\alpha$-2b, levamisole or Propagermanium, etc.

In one aspect, provided herein is a compound or pharmaceutical composition comprising the compound disclosed herein in preventing, treating or lessening viral diseases In one aspect, a compound or pharmaceutical composition of the invention is used in the manufacture of a medicament for preventing, managing, treating or lessening hepatitis B disease in patients. Hepatitis B disease refers to liver diseases caused by hepatitis B virus infection or hepatitis B virus infection, including acute hepatitis, chronic hepatitis, cirrhosis and liver cancer. Acute hepatitis B virus infection can be asymptomatic or manifest as acute hepatitis symptoms. Patients with chronic viral infections have active diseases that can progress to cirrhosis and liver cancer.

The use of the compound or pharmaceutical composition of the invention comprises inhibiting the formation or secretion of HBsAg, and also comprises administering to a patient a pharmaceutically acceptable effective dose of the compound or the pharmaceutical composition of the invention.

The use of the compound or pharmaceutical composition of the invention comprises inhibiting the formation of HBV DNA, and also comprises administering to a patient a pharmaceutically acceptable effective dose of the compound or the pharmaceutical composition of the invention.

In one aspect, the use of the compound or pharmaceutical composition of the invention in inhibiting expression of HBV gene comprises administering to a patient a pharmaceutically acceptable effective dose of the compound or or pharmaceutical composition of the invention.

Those additional anti-HBV drugs can be administered separately from the pharmaceutical composition comprising the compound of the present invention, as a part of the multi-administration regimen. Alternatively, those therapeutic agents may be part of a single dosage form, mixed with the compound of the present invention to form a single composition. If the administration is part of a multi-dosing regimen, the two active agents can be delivered simultaneously or continuously for a period of time to obtain the target reagent activity.

The dosage change of compound and composition that can be combined with the carrier material to produce a single dosage form (the composition comprising an additional therapeutic agent as described in the present invention) depends on the attending and administration modes. The compounds of the invention show a strong antiviral effect. These compounds have unexpected antiviral activity against HBV and are therefore suitable for the treatment of various diseases caused by the virus, especially those caused by acute and chronic persistent HBV infection. Chronic viral diseases caused by HBV can lead to a variety of syndromes of varying severity. It is well known that chronic hepatitis B virus infection can lead to cirrhosis and/or liver cancer.

Examples of indications that can be treated with the compounds of the invention are the treatment of acute and chronic viral infections that can cause infectious hepatitis, such as Hepatitis B virus infection, particularly preferred treatment of chronic hepatitis B virus infection and acute hepatitis B virus infection.

The invention further relates to the use of the compounds and compositions of the invention for the preparation of a medicament for the treatment and prevention of viral diseases, in particular hepatitis B.

In one aspect, the method of preventing, treating or lessening viral diseases comprises administering a therapeutically effective dose of the compound or the pharmaceutical composition to a patient, wherein the viral disease is Hepatitis B virus infection or cirrhosis or hepatocellular carcinoma caused by Hepatitis B virus infection.

In one aspect, the method of inhibiting the formation or secretion of HBsAg, and/or inhibiting the formation of HBV DNA comprises administering a therapeutically effective dose of the compound or the pharmaceutical composition to a patient.

General Synthetic Procedures

To describe the invention, the examples are listed below. However, it should be understood that the invention is not limited to the embodiments, but merely provides a method of practicing the invention.

Generally, the compounds disclosed herein may be prepared by methods described herein, wherein the substituents are as defined for Formula (I), Formula (II) or Formula (III) above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius (° C.). Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

1H NMR spectra were recorded by a Bruker Avance 400 MHz spectrometer or Bruker Avance III HD 600 spectrometer, using $CDCl_3$, -DMSO-$d_6$, $CD_3OD$ or acetone-$d_6$ (reported in ppm) as solvent, and using TMS (0 ppm) or chloroform (7.26 ppm) as the reference standard. When peak multiplicities are reported, the following abbreviations are used: s (singlet), s, s (singlet, singlet), d (doublet), t (triplet), m (multiplet), br (broadened), dd (doublet of doublets), ddd (doublet of doublet of doublets), dt (doublet of triplets), ddt (doublet of doublet of triplets), td (triplet of doublets), br.s (broadened singlet). Coupling constants J, when given, were reported in Hertz (Hz).

Low-resolution mass spectral (MS) data were also determined on an Agilent 6320 series LC-MS spectrometer equipped with G1312A binary pumps, a G1316A TCC (Temperature Control of Column, maintained at 30° C.), a G1329A autosampler and a G1315B DAD detector were used in the analysis. An ESI source was used on the LC-MS spectrometer.

Low-resolution mass spectral (MS) data were also determined on an Agilent 6120 series LC-MS spectrometer equipped with G1311A binary pumps, a G1316A TCC (Temperature Control of Column, maintained at 30° C.), a G1329A autosampler and a G1315D DAD detector were used in the analysis. An ESI source was used on the LC-MS spectrometer.

Both LC-MS spectrometers were equipped with an Agilent Zorbax SB-C18, 2.1×30 mm, m column. Injection volume was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B). The gradient elution conditions were showed in Table 1: The gradient elution conditions were showed in Table 1:

TABLE 1

The gradient elution conditions

| Time (min) | A (CH$_3$CN,0.1% HCOOH) | B (H$_2$O,0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

Purities of compounds were assessed by Agilent 1100 Series high performance liquid chromatography (HPLC) with UV detection at 210 nm and 254 nm (Zorbax SB-C18, 2.1×30 mm, 4 micron). The run time was 10 min, and the flow rate was 0.6 mL/min. The elution was performed with a gradient of 5 to 95% phase A (0.1% formic acid in CH$_3$CN) in phase B (0.1% formic acid in H$_2$O). Column was operated at 40° C.

The following abbreviations are used throughout the specification:

AcOK potassium acetate
MeCN, CH$_3$CN acetonitrile
MeOH methanol
DCM, CH$_2$Cl$_2$ dichloromethane
DBU 1,8-diazabicyclo[5.4.0]undec-7-ene
D$_2$O heavy water
DME 1,2-Dimethoxyethane
DMSO dimethylsulfoxide
DMF N,N-dimethylformamide
DMAP 4-dimethylaminopyridine
DIBAH diisobutylaluminum hydride
DMF-DMA N,N-dimethylformamide dimethyl acetal
CHCl$_3$ chloroform, trichloromethane
CDCl$_3$ chloroform-d
Boc tert-butoxycarbonyl
(Boc)$_2$O Di-tert-butyl dicarbonate
Bn benzyl
PE petroleum ether
Pd(dba)$_2$ Bis(dibenzylideneacetone)palladium
Pd$_2$(dba)$_3$ tris(dibenzylideneacetone)dipalladium
Ph phenyl
PTSA p-toluenesulfonic acid
EA, EtOAc ethyl acetate
EtOH ethyl alcohol
HCl Hydrogen chloride
K$_2$CO$_3$ potassium carbonate
NaHCO$_3$ sodium bicarbonate
NH$_4$OAc ammonium acetate
NaOH sodium hydroxide
NaBH$_3$CN sodium cyanoborohydride
Na$_2$SO$_4$ sodium sulfate
Et$_3$N, TEA triethylamine
NBS N-bromosuccinimide
DMSO-d$_6$ Deuterated dimethyl sulfoxide
M mol/L
NaH Sodium hydride
HATU 2-(7-aza-H-benzotriazole-1-yl)-1,1,3,3-tetramethyluronium hexafluorophosphate
Xantphos 4,5-bisdiphenylphosphino-9,9-dimethylxanthene
H$_2$O water
HCl/EtOAc ethyl chloride solution of hydrogen chloride
HOAT 1-hydroxy-7-azabenzotriazole
DIPEA N,N-diisopropylethylamine
DCC dicyclohexylcarbodiimide
DMF N,N-dimethylformamide
DMA Dimethylacetamide
THF tetrahydrofuran
TFA trifluoroacetic acid
Tf Trifluoromethanesulfonyl
LiOH·H$_2$O Lithium hydroxide monohydrate
IPA Isopropanol
CuCN Cuprous cyanide
CH$_3$OH Methanol
N$_2$ Nitrogen
NH$_4$Cl ammonium chloride
NH$_4$OAc Ammonium acetate
Ac$_2$O acetic anhydride
mL milliliter
min minute, minutes
m-CPBA m-chloroperoxybenzoic acid
h hour, hours
RT rt room temperature
Rt retention time
t$_{1/2}$ half life
t-BuOH tert-butanol
AUC the calculated Area Under the Curve
Vss the apparent volume of distribution at steady—state
CL, clearance
F, absolute bioavailability
Dose
T$_{max}$ maximum time
C$_{max}$ maximum concentration
hr*ng/mL blood concentration*time
dppfPdCl$_2$ 1,1'-bisdiphenylphosphinoferrocene palladium dichloride Synthesis Method The experimental steps for preparing the compounds disclosed in the present invention were listed in the following synthetic scheme. Wherein each of R$^2$, R$^3$, R$^4$, R$^5$, R$^6$, R$^7$, R$^8$ and R$^9$ has the meaning as described in the present invention, and X is halogen. R$^1$ is hydrogen, deuterium, heterocyclyl consisting of 5-6 ring atoms, heteroaryl consisting of 5-6 ring atoms, C$_{1-6}$ alkyl group, C$_{2-6}$ alkenyl, C$_{2-6}$ alkynyl or C$_{3-7}$ cycloalkyl, wherein heterocyclyl consisting of 5-6 ring atoms, heteroaryl consisting of 5-6 ring atoms, C$_{1-6}$ alkyl, C$_{2-6}$ alkenyl, C$_{2-6}$ alkynyl or C$_{3-7}$ cycloalkyl are independently unsubstituted or substituted by 1, 2, 3 or 4 R$^v$; R$^v$ has the meaning as described in the present invention.

Scheme 1

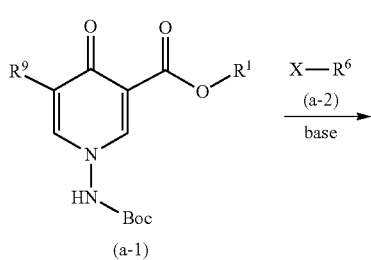

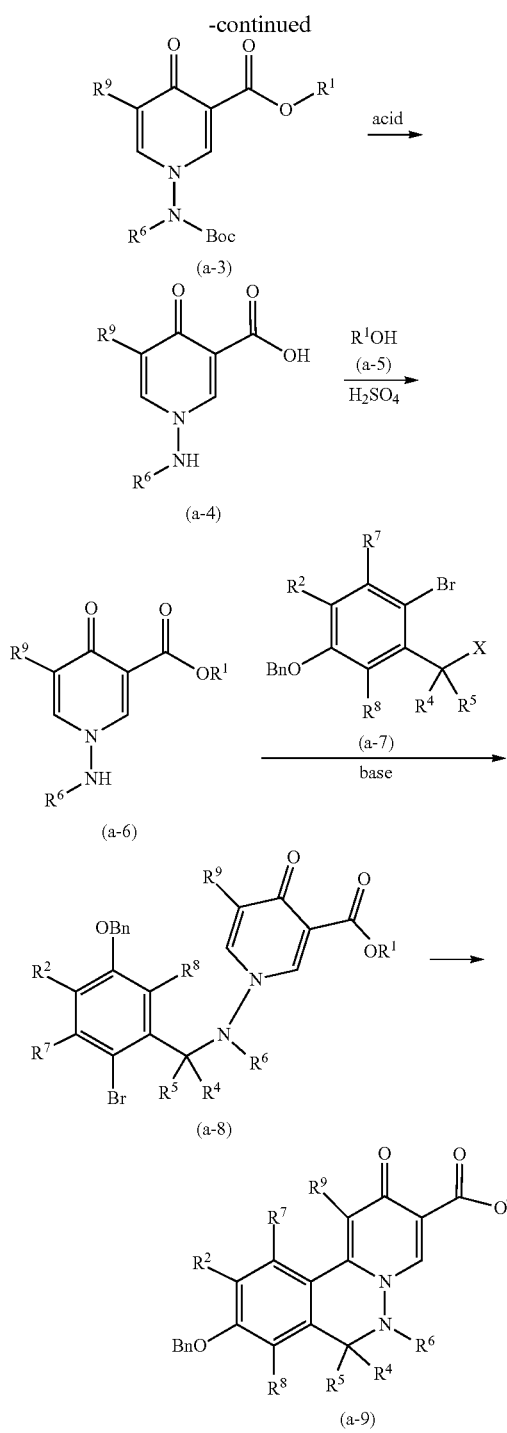

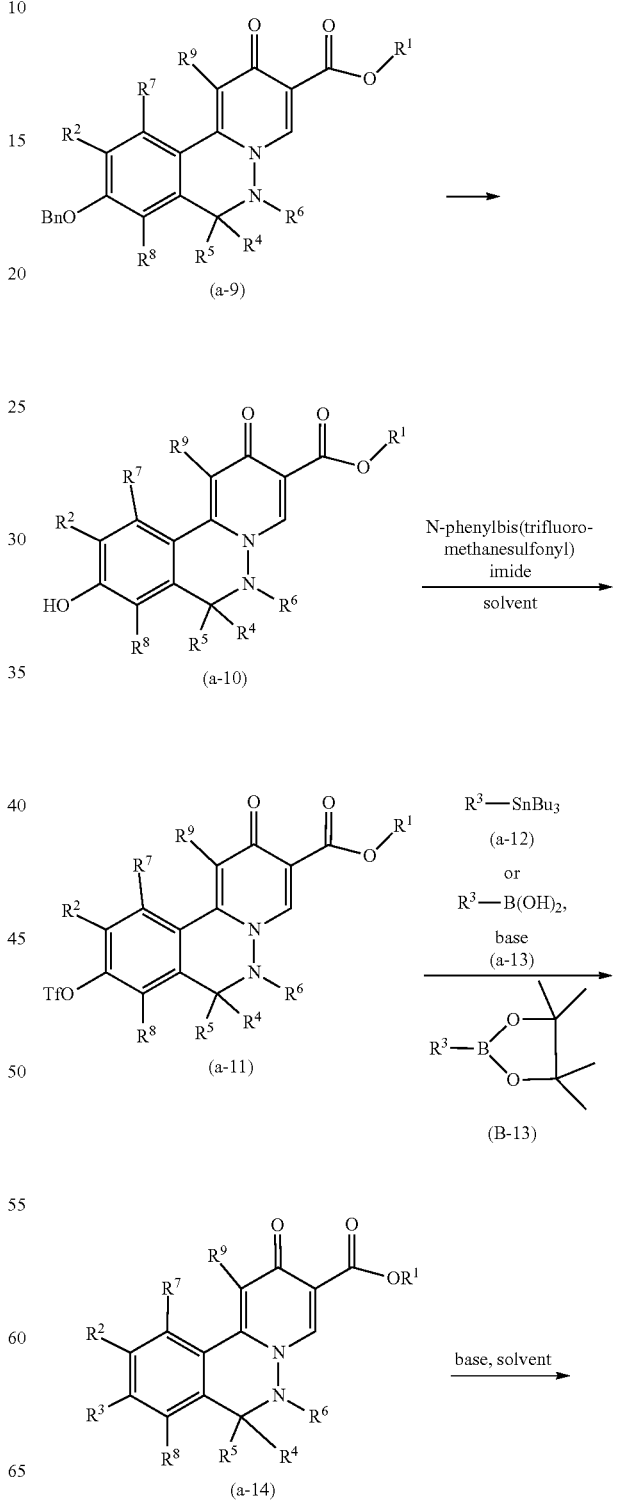

bonate, etc.) and in a suitable solvent (such as acetonitrile, etc.) to give a compound (a-8); compound (a-8) can subjected to a intermolecular coupling reaction under the action of Pd catalyst (such as palladium bromide, etc.), a base (such as potassium acetate, etc.) and a suitable solvent (such as DMA, etc.) to give a compound (a-9).

Scheme 2

Compound (a-9) disclosed herein can be prepared by the process illustrated in scheme 1. Compound (a-1) can react with chloride (a-2) under basic conditions (such as potassium carbonate, sodium carbonate, etc.) in a suitable solvent (e.g. cetonitrile, DMF, etc.) to give a compound (a-3); compound (a-3) can be subjected to a reaction under acidic conditions (such as trifluoroacetic acid) and in a suitable solvent (such as DCM, etc.) to give a compound (a-4); compound (a-4) can react with compound (a-5) to give a compound (a-6) under the action of concentrated sulfuric acid; compound (a-6) can react with compound (a-7) under basic conditions (such as potassium carbonate, sodium car-

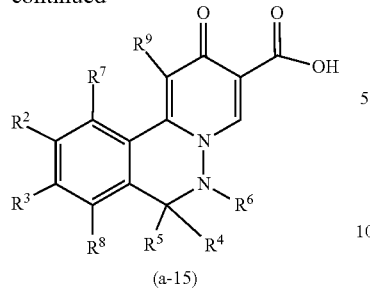

(a-15)

Compound (a-15) disclosed herein can be prepared by the process illustrated in scheme 2. First, the benzyl-protecting group of compound (a-9) can be removed to give a compound (a-10), then compound (a-10) can react with N-phenylbis(trifluoromethanesulfonyl)imide under basic conditions (such as triethylamine, etc.) and in a suitable solvent (such as dichloromethane, etc.) to give a compound (a-11); at last, compound (a-11) can be subjected to a coupling reaction with compound (a-12) under the action of palladium catalyst (such as bistriphenylphosphorus palladium dichloride, etc.) and in a suitable solvent (such as 1,4 dioxane, etc.) to give a compound (a-14), or compound (a-11) can be subjected to a coupling reaction with compound (a-13) or compound (B-13) under the action of palladium catalyst (such as tetratriphenylphosphine palladium, etc.), in a suitable solvent (such as 1,4 dioxane, etc.) and a suitable base to give a compound (a-14); compound (a-14) can react in a base (such as lithium hydroxide, etc.) and a suitable solvent (such as methanol, etc.) to give a compound (a-15).

EXAMPLES

The following examples are intended to illustrate the invention but are not intended to limit the scope of the invention.

Preparation Examples

In the following preparation examples, the preparation process of the compound of the present invention has been described in detail by taking a part of the compounds of the present invention as an example.

Example 1 9-(furan-2-yl)-6-isopropyl-10-methoxy-2-oxo-6,7-dihydro-2H-pyrido[2,1-a]phthalazine-3-carboxylic acid

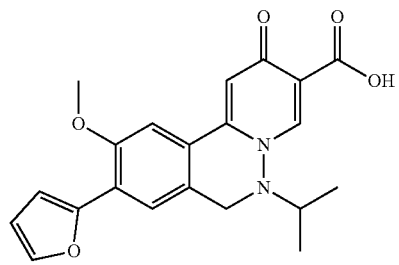

Step 1: tert-butyl 2-((dimethylamino)methylene)-3-oxobutyric acid

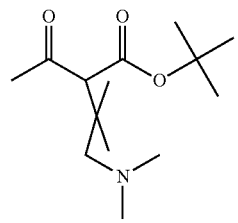 [SMILES: CC(=O)C(C(=O)OC(C)(C)C)C(C)(C)CN(C)C]

tert-Butyl acetoacetate (30 g 189.63 mmol), DMF-DMA (45 g 377.64 mmol) and 1,4-dioxane (200 mL) were added into the reaction flask. The reaction mixture was stirred for 12 h at rt, and then concentrated in vacuo to remove the solvent. The residue was diluted with ethyl acetate (200 mL), and the resulted mixture was washed with water (200 mL×3). The organic phase was dried over anhydrous sodium sulfate and filtered. The filtrate was concentrated in vacuo to give the title compound as brown oil (40 g, 187.56 mmol, 98.90%). MS (ESI, pos.ion) m/z: 214.3[M+H]$^+$

Step 2: tert-butyl 4-oxo-4H-pyran-3-formate

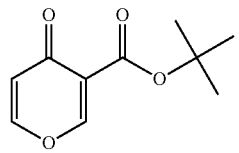

tert-Butyl 2-((dimethylamino)methylene)-3-oxobutyric acid (20 g, 93.778 mmol), tetrahydrofuran (200 mL) and ethyl formate (14 g, 189.0 mmol) were added into the reaction flask, then sodium tert-butoxide (24 g, 242.2 mmol) was added under an ice bath. The mixture was heated to rt and stirred for 12 h. The reaction solution was quenched with HCl aqueous solution (500 mL, 1 M), extracted with ethyl acetate (200 mL×3). The combined organic phases were washed with saturated aqueous sodium bicarbonate (300 mL×2) and saturated aqueous sodium chloride (300 mL×1), then concentrated in vacuo. The residue was purified by silica gel column chromatography (PE/EA(V/V)=1/1) to give the title compound as a yellow solid (10 g, 50.97 mmol, 54.35%). MS (ESI, pos.ion) m/z: 141.2[M−56+1]$^+$

Step 3: tert-butyl 1-((tert-Butoxycarbonyl)amino)-4-oxo-1,4-dihydropyridine-3-formate

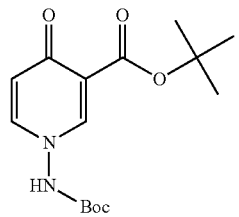 [SMILES: CC(C)(C)OC(=O)Nn1ccc(=O)c(C(=O)OC(C)(C)C)c1]

tert-Butyl 4-oxo-4H-pyran-3-formate (18 g, 91.743 mmol), tert-butyl carbazate (24.3 g 184 mmol), ethanol (180 mL) were added into the reaction flask, and the solution was heated and refluxed for 12 h. After the reaction was completed, the reaction mixture was concentrated in vacuo, and the residue was purified by silica gel column chromatography (PE/EA(V/V)=1/2) to give the title compound as an orange solid (28 g, 90.24 mmol, 98.36%). MS (ESI, pos.ion) m/z: 311.1[M+H]$^+$ Step 4: tert-butyl 1-((tert-butoxycarbonyl)(isopropyl)amino)-4-oxo-1,4-dihydropyridine-3-formate

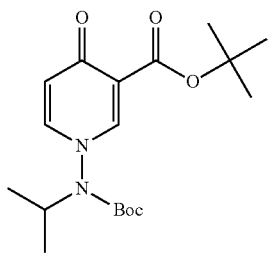 [SMILES: CC(C)N(C(=O)OC(C)(C)C)n1ccc(=O)c(C(=O)OC(C)(C)C)c1]

tert-Butyl 1-((tert-butoxycarbonyl)amino)-4-oxo-1,4-dihydropyridine-3-formate (28 g, 90.24 mmol), acetonitrile (300 mL), potassium carbonate (25 g, 180.89 mmol) and 2-bromopropane (22 g, 178.87 mmol) were added into the reaction flask. After addition, the solution was warmed to 80° C. and reacted for 12 h. The reaction solution was filtered, the filtrate was concentrated in vacuo, and the residue was directly subjected to the next step without purification. MS (ESI, pos.ion) m/z: 353.3[M+H]$^+$ Step 5: 1-(Isopropylamino)-4-oxo-1,4-dihydropyridine-3-carboxylic acid

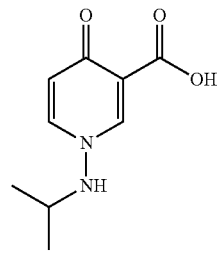

tert-Butyl 1-((tert-butoxycarbonyl)(isopropyl)amino)-4-oxo-1,4-dihydropyridine-3-formate obtained in step 4 was dissolved in dichloromethane (200 mL), and trifluoroacetate (100 mL, 1323 mmol) was slowly added under an ice bath. After addition, the mixture was warmed to rt and stirred for 12 h, then concentrated in vacuo, and the residue was directly subjected to the next step without purification. MS (ESI, pos.ion) m/z: 197.2[M+H]$^+$ Step 6: Methyl 1-(isopropylamino)-4-oxo-1,4-dihydropyridine-3-carboxylate

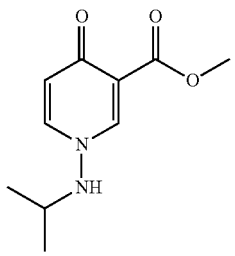

1-(Isopropylamino)-4-oxo-1,4-dihydropyridine-3-carboxylic acid obtained in step 5, MeOH (200 mL) and concentrated sulfuric acid (5 mL, 90.90 mmol, 18.18 mol/L) were added into the reaction flask. After addition, the reaction solution was refluxed for 24 h. Solid sodium bicarbonate was added slowly to the reaction solution until no bubbles were formed under an ice bath. The reaction solution was filtered, the filtrate was concentrated in vacuo, then the residue was purified by silica gel column chromatography (EA) to give the title compound as a dark red solid (10 g, 47.57 mmol, yield: 53%). MS (ESI, pos.ion) m/z: 211.1 [M+1]+.

Step 7: 5-benzyloxy-2-bromo-4-methoxybenzyl alcohol

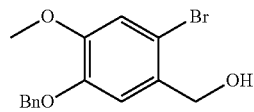 [SMILES: COc1cc(Br)c(CO)cc1OCc1ccccc1]

5-(Benzyloxy)-2-bromo-4-methoxybenzaldehyde (7.8 g, 24 mmol) and methanol (78 mL) were added to the reaction bottle. Sodium borohydride (1.1 g, 29 mmol) was added under an ice bath. After addition, the reaction solution was stirred at rt for 3 h. The reaction solution was quenched with water (200 mL) and methanol was removed by rotary evaporation, then the residue was extracted with ethyl acetate (100 mL×2). The organic phases were combined. The combined organic phases were dried over anhydrous sodium sulfate and concentrated in vacuo. The residue was directly used in the next step without purification.

Step 8: 1-(Benzyloxy)-4-bromo-5-(chloromethyl)-2-methoxybenzene

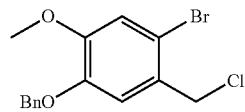

5-Benzyloxy-2-bromo-4-methoxybenzyl alcohol obtained in step 7 was dissolved in dichloromethane (80 mL), thionyl chloride (2.6 mL, 36 mmol, 100 mass %) was added under an ice bath. After addition, the reaction solution was warmed to rt and stirred at rt for 3 h and concentrated in vacuo. The residue was directly used in the next step without purification.

Step 9: Methyl 1-((5-(benzyloxy)-2-bromo-4-methoxybenzyl)(isopropyl)amino)-4-oxo-1,4-dihydropyridine-3-carb oxylate

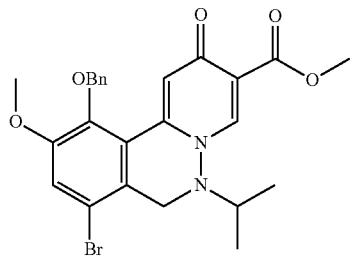 [SMILES: COC(=O)c1cn2c(cc1=O)-c1c(c(Br)cc(OC)c1OCc1ccccc1)CN2C(C)C]

1-(Benzyloxy)-4-bromo-5-(chloromethyl)-2-methoxybenzene obtained in step 8 was dissolved in acetonitrile (80 mL). Methyl 1-(isopropylamino)-4-oxo-1,4-dihydropyridine-3-carboxylate (5.6 g, 27 mmol), potassium carbonate (6.7 g, 48 mmol) and potassium iodide (0.4 g 2 mmol) were added. After addition, the solution was warmed to 80° C. and reacted overnight. The reaction mixture was filtered. The filtrate was concentrated to give the title compound as brown oil (11 g 21.34 mmol, yield; 88.9%), which was directly used in the next step without purification. MS (ESI, pos.ion) m/z: 516.0 [M+1]+;

Step 10: Methyl 9-(benzyloxy)-6-isopropyl-10-methoxy-2-oxo-6,7-dihydro-2H-pyrido[2,1-a]phthalazine-3-formate

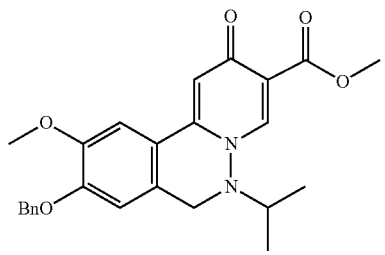

Methyl 1-((5-(benzyloxy)-2-bromo-4-methoxybenzyl)(isopropyl)amino)-4-oxo-1,4-dihydropyridine-3-carb oxylate (11 g, 21.34 mmol), N,N-dimethylacetamide (100 mL), palladium bromide (0.57 g, 2.1 mmol) and potassium acetate (4.2 g, 43 mmol) were added into the dry reaction flask. After addition, the solution was warmed to 130° C. under protection of nitrogen and reacted for 12 h. The reaction solution was concentrated and the residue was purified by silica gel column chromatography (DCM/MeOH(V/V)=15/1) to give the title compoud as brown oil (3.2 g 7.4 mmol, 35%). MS (ESI, pos.ion) m/z: 435.1[M+1]+;

Step 11: Methyl 9-hydroxy-6-isopropyl-10-methoxy-2-oxo-6,7-dihydro-2H-pyrido[2,1-a]phthalazine-3-formate

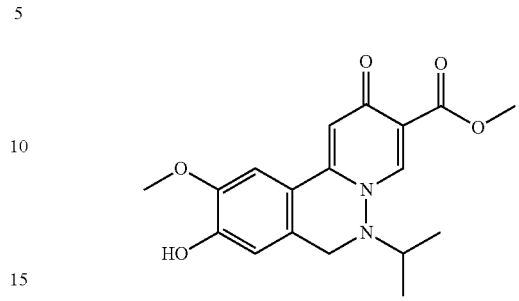

Methyl 9-(benzyloxy)-6-isopropyl-10-methoxy-2-oxo-6,7-dihydro-2H-pyrido[2,1-a]phthalazine-3-formate (3.0 g, 6.9 mmol), methanol (20 mL) and Pd/C (0.4 g 0.4 mmol, 10 mass %) were added to the reaction flask. The solution was degassed and refilled with hydrogen for three times and then stirred for 12 h at rt. The reaction solution was filtered. The filtrate was concentrated in vacuo to give the title compound as a pale solid, which was directly used in the next step without purification. MS (ESI, pos.ion) m/z: 345.2[M+H]+

Step 12: Methyl 6-isopropyl-10-methoxy-2-oxo-9-((((trifluoromethyl)sulfonyl)oxy)-6,7-dihydro-2H-pyrido[2,1-a]phthalazine-3-formate

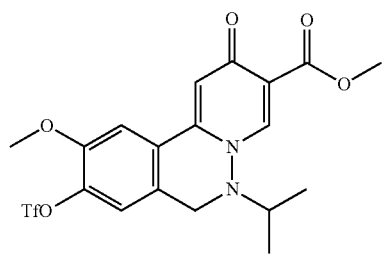

Methyl 9-hydroxy-6-isopropyl-10-methoxy-2-oxo-6,7-dihydro-2H-pyrido[2,1-a]phthalazine-3-formate obtained in step 11 and dichloromethane (25 mL) were added into the reaction flask. DBU (2.8 g 18 mmol) and N-phenylbis(trifluoromethanesulfonyl)imide (5.2 g, 14 mmol) were added under an ice bath. After addition, the solution was warmed to rt and reacted for 12 h. The reaction solution was quenched with HCl aqueous solution (50 mL, 1M) and extracted with DCM (30 mL×3). The organic phases were combined. The combined organic phases were concentrated in vacuo and the residue was purified by silica gel column chromatography (DCM/MeOH (V/V)=15/1) to give the title compound as a brown solid (2.0 g, 4.2 mmol, yield: 61%). MS (ESI, pos.ion) m/z: 477.0[M+1]+

Step 13: 9-(furan-2-yl)-6-isopropyl-10-methoxy-2-oxo-6,7-dihydro-2H-pyrido[2,1-a]phthalazine-3-carboxylic acid

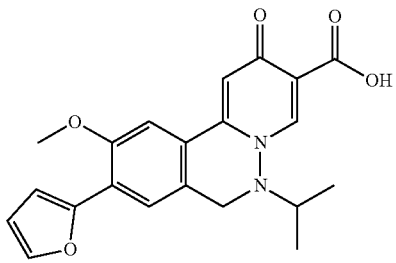 [SMILES: COc1cc2c(cc1-c1ccco1)CN(C(C)C)n1cc(C(=O)O)c(=O)cc1-2]

Methyl 6-isopropyl-10-methoxy-2-oxo-9-(((trifluoromethyl)sulfonyl)oxy)-6,7-dihydro-2H-pyrido[2,1-a]phthalazine-3-formate (500 mg, 1.050 mmol), 2-furan boric acid (0.18 g, 1.6 mmol), tetratriphenylphosphine palladium (0.12 g, 0.10 mmol), potassium carbonate (0.43 g, 3.1 mmol) and 1,4-dioxane (10 mL) were added into the reaction flask. The mixture was reacted at 110° C. for 12 h under nitrogen. To the reaction solution were added methanol (5 mL) and LiOH (0.22 g, 5.2 mmol). The resulting mixture was then reacted at rt for 4 h. The reaction solution was concentrated in vacuo. The residue was dilluted with HCl aqueous solution (20 mL 1M) and extracted with DCM (10 mL×3). The combined organic phases were concentrated in vacuo and the residue was purified by silica gel column chromatography (DCM/MeOH(V/V)=15/1) to give the title compound as a light yellow solid (210 mg, 0.5521 mmol, 54.43%). MS (ESI, pos.ion) m/z: 381.1[M+1]$^+$; $^1$H NMR (400 MHz, DMSO-d$_6$) δ 8.50 (s, 1H), 7.88 (s, 1H), 7.85 (s, 1H), 7.76 (s, 1H), 7.67 (s, 1H), 7.12 (d, J=3.3 Hz, 1H), 6.71-6.62 (m, 1H), 4.58 (s, 2H), 4.07 (s, 3H), 3.02-2.83 (m, 1H), 0.95 (d, J=4.8 Hz, 6H).

Example 2: 6-isopropyl-10-methoxy-2-oxo-9-(thiophen-2-yl)-6,7-dihydro-21H-pyrido[2,1-a]phthalazine-3-carboxylic acid

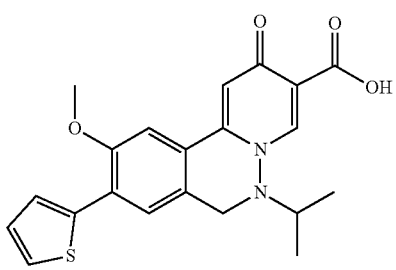 [SMILES: COc1cc2c(cc1-c1cccs1)CN(C(C)C)n1cc(C(=O)O)c(=O)cc1-2]

Methyl 6-isopropyl-10-methoxy-2-oxo-9-(((trifluoromethyl)sulfonyl)oxy)-6,7-dihydro-2H-pyrido[2,1-a]phthalazine-3-formate (500 mg, 1.050 mmol), 2-tributylstannylthiophene (780 mg, 2.090 mmol), ditriphenylphosphine palladium dichloride (73 mg, 0.104 mmol) and 1,4-dioxane (10 mL) were added to the reaction flask. The reaction solution was reacted at 110° C. for 12 h under protection of nitrogen. Methanol (5 mL) and LiOH (0.22 g, 5.2 mmol) were added to the reaction solution which was reacted at rt for 4 h. The reaction solution was concentrated. The residue was dilluted with HCl aqueous solution (20 mL 1M) and extracted with DCM (10 mL×3). The combined organic phases were concentrated and the residue was purified by silica gel column chromatography (DCM/MeOH(V/V)=15/1) to give the title compound as a light yellow solid (230 mg, 0.5801 mmol, 59.53%). MS (ESI, pos.ion) m/z: 397.1 [M+1]$^+$; $^1$H NMR (400 MHz, DMSO-d$_6$) δ 8.50 (s, 1H), 7.94 (s, 1H), 7.84-7.71 (m, 2H), 7.68 (d, J=3.3 Hz, 2H), 7.26-7.13 (m, 1H), 4.56 (s, 2H), 4.07 (s, 3H), 3.00-2.83 (m, 1H), 0.96 (d, J=4.7 Hz, 6H).

Example 3: 6-isopropyl-10-methoxy-2-oxo-9-(thiazol-2-yl)-6,7-dihydro-2H-pyrido[2,1-a]phthalazine-3-carboxylic acid

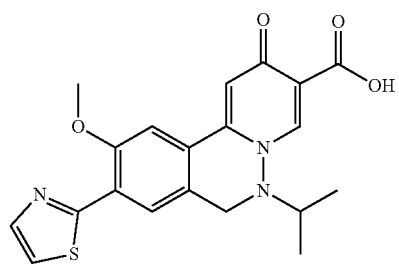 [SMILES: COc1cc2c(cc1-c1nccs1)CN(C(C)C)n1cc(C(=O)O)c(=O)cc1-2]

Methyl 6-isopropyl-10-methoxy-2-oxo-9-(((trifluoromethyl)sulfonyl)oxy)-6,7-dihydro-2H-pyrido[2,1-a]phthalazine-3-formate (500 mg, 1.050 mmol), 2-tributylstannylthiazole (0.78 g, 2.1 mmol), tetratriphenylphosphine palladium (0.12 g, 0.10 mmol), ditriphenylphosphine palladium dichloride (73 mg, 0.10 mmol) and 1,4-dioxane (10 mL) were added into the reaction flask. The mixture was reacted for 12 h at 110° C. under protection of nitrogen. The reaction solution was concentrated in vacuo and the residue was purified by silica gel column chromatography (DCM/MeOH(V/V)=15/1) to give the title compoud as a light yellow solid (290 mg, 69.53%). MS (ESI, pos.ion) m/z: 398.1 [M+1]$^+$; $^1$H NMR (400 MHz, DMSO-d$_6$) δ 8.51 (s, 1H), 8.42 (s, 1H), 8.03 (d, J=3.2 Hz, 1H), 7.95-7.87 (m, 2H), 7.74 (s, 1H), 4.63 (s, 2H), 4.17 (s, 3H), 3.00-2.81 (m, 1H), 0.95 (d, J=4.3 Hz, 6H).

Example 4: 6-isopropyl-9-(1-isopropyl-1H-pyrazol-4-yl)-10-methoxy-2-oxo-6,7-dihydro-2H-pyrido[2,1-a]phthalazine-3-carboxylic acid

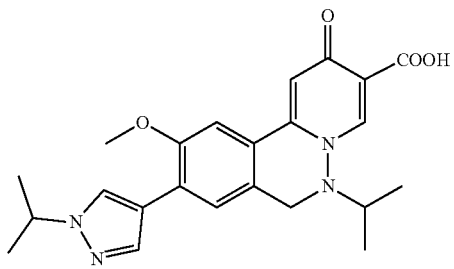 [SMILES: COc1cc2c(cc1-c1cnn(C(C)C)c1)CN(C(C)C)n1cc(C(=O)O)c(=O)cc1-2]

Step 1: 1-isopropyl-4-(4,4,5,5-tetramethyl-1,3,2-dioxaborolan-2-yl)-1H-pyrazole

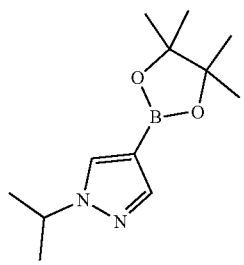 [SMILES: CC(C)n1cc(B2OC(C)(C)C(C)(C)O2)cn1]

To the reaction flask were added 4-(4,4,5,5-Tetramethyl-1,3,2-dioxaborolan-2-yl)-1H-pyrazole (1 g, 5.1 mmol), barium carbonate (2.52 g7.7 mmol), N,N-dimethylformamide (25 mL) and 2-iodopropane (0.58 mL, 5.7 mmol) were added in turn. The reaction solution was warmed to 90° C. and stirred for 24 h. Water was added to dissolve the solid after the reaction was completed. The solution was extracted with ethyl acetate (30 mL×3). The organic phases were combined. The combined organic phases were washed with saturated sodium chloride solution and concentrated in vacuo. The residue was purified by silica gel column chromatography (PE/EA(V/V)=15/1) to give the title compound as a white solid (555 mg, 45.60%). MS (ESI, pos.ion) m/z: 237.3[M+H]+

Step 2: methyl 6-isopropyl-9-(1-isopropyl-1H-pyrazol-4-yl)-10-methoxy-2-oxo-6,7-dihydro-2H-pyrido[2,1-a]phthalazine-3-formate

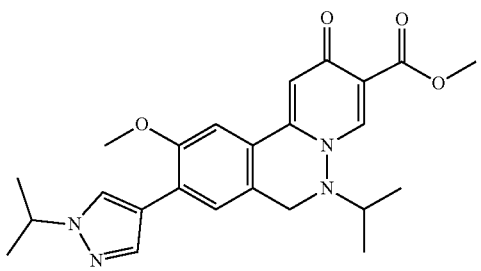 [SMILES: COC(=O)c1cn2c(cc1=O)-c1cc(OC)c(-c3cnn(C(C)C)c3)cc1CN2C(C)C]

To the dry flask were added Methyl 6-isopropyl-10-methoxy-2-oxo-9-(((trifluoromethyl)sulfonyl)oxy)-6,7-dihydro-2H-pyrido[2,1-a]phthalazine-3-formate (205 mg, 0.43 mmol), 1-isopropyl-4-(4,4,5,5-tetramethyl-1,3,2-dioxaborolan-2-yl)-1H-pyrazole (182 mg, 0.77 mmol), sodium bicarbonate (109 mg, 1.30 mmol), 1,1'-bis(diphenylphosphino)ferrocene palladium(II) chloride complex (53 mg, 0.06 mmol), water (1 mL) and ethylene glycol dimethyl ether (5 mL) in turn. The reaction mixture was degassed and refilled with nitrogen for three times, warmed to 65° C. and stirred for 3 h under protection of nitrogen. Post processing: the reaction mixture was filtered through a celite pad to remove solids. The filtrate was concentrated and the residue was purified by preparative thin-layer plate separation (DCM/MeOH(V/V)=15/1) to give the title compound as a brown red solid (258 mg, 137.4%).

MS (ESI, pos.ion) m/z: 437.3 [M+H]+

Step 3: 6-isopropyl-9-(1-isopropyl-1H-pyrazol-4-yl)-10-methoxy-2-oxo-6,7-dihydro-2H-pyrido[2,1-a]phthalazine-3-carboxylic acid

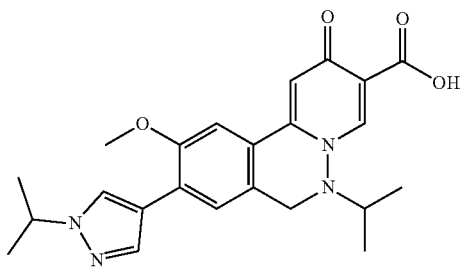 [SMILES: COc1cc2c(cc1-c1cnn(C(C)C)c1)CN(C(C)C)n1cc(C(=O)O)c(=O)cc1-2]

Methyl 6-isopropyl-9-(1-isopropyl-1H-pyrazol-4-yl)-10-methoxy-2-oxo-6,7-dihydro-2H-pyrido[2,1-a]phthalazine-3-formate (387 mg, 0.89 mmol), methanol (5 mL) and tetrahydrofuran (2 mL) were added into the reaction flask. The mixture was stirred for dissolution, then lithium hydroxide monohydrate (186 mg, 4.4 mmol) and water (2 mL) were added. The reaction mixture was stirred at rt for 5 h. Post processing: the solution was adjusted to pH 4 with 1M hydrochloric acid and filtered after stirring for 1 h. The filter cake was collected and dried to give the crude product as a brown solid. The obtained solid was added with methanol (4 mL) and stirred at rt for 2 h and then filtered to give the title compound as a pale solid (167 mg, 44.58%).

MS (ESI, pos.ion) m/z: 423.2[M+H]+; $^1$H NMR (400 MHz, CDCl$_3$) δ 8.61 (s, 1H), 8.09-7.82 (m, 2H), 7.45 (s, 1H), 7.28 (s, 1H), 7.11 (s, 11H), 4.56 (dt, J=12.8, 6.3 Hz, 1H), 4.40 (s, 2H), 4.02 (s, 3H), 3.01 (dt, J=12.2, 6.0 Hz, 1H), 1.56 (d, J=6.5 Hz, 6H), 1.01 (d, J=5.5 Hz, 6H).

Example 5: 9-(1-(difluoromethyl)-1H-pyrazole-4-yl)-6-isopropyl-10-methoxy-2-oxo-6,7-dihydro-2H-pyrido [2,1-a]phthalazine-3-carboxylic acid

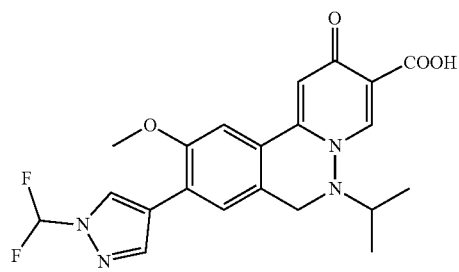

Step 1: 1-(difluoromethyl)-4-(4,4,5,5-tetramethyl-1,3,2-dioxaborolan-2-yl)-1H-pyrazole

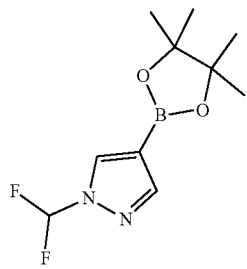 [SMILES: CC1(C)OB(c2cnn(C(F)F)c2)OC1(C)C]

To a solution of 4-(4,4,5,5-Tetramethyl-1,3,2-dioxaborolan-2-yl)-1H-pyrazole (1 g, 5.155 mmol) and 18-crown-6 (275 mg, 1.03 mmol) in acetonitrile (25 mL) was added sodium difluorochloroacetate (853 mg, 5.54 mmol). The reaction mixture was heated to reflux and stirred for 18 h, then filtered through a pad of diatomaceous earth. The filtrate was concentrated in vacuo The residue was purified by silica gel column chromatography (PE/EA(V/V)=15/1) to give the title compound as a white solid (772 mg, 3.164 mmol, 61.38%). MS (ESI, pos.ion) m/z: 245.2[M+H]$^+$.

Step 2: 9-(1-(difluoromethyl)-1H-pyrazole-4-yl)-6-isopropyl-10-methoxy-2-oxo-6,7-dihydro-2H-pyrido[2,1-a]phthalazine-3-carboxylic acid

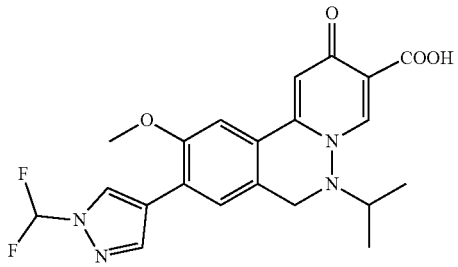 [SMILES: COc1cc2c(cc1-c1cnn(C(F)F)c1)CN(C(C)C)n1cc(C(=O)O)c(=O)cc1-2]

Methyl 6-isopropyl-10-methoxy-2-oxo-9-(((trifluoromethyl)sulfonyl)oxy)-6,7-dihydro-2H-pyrido[2,1-a]phthalazine-3-formate and 1-(difluoromethyl)-4-(4,4,5,5-tetramethyl-1,3,2-dioxaborolan-2-yl)-1H-pyrazole were taken as raw material to give the title compound as a gray solid according to synthetic method in step 2-3 of example 4. MS (ESI, pos.ion) m/z: 431.2[M+H]$^+$; $^1$H NMR (400 MHz, DMSO-d$_6$) δ 8.71 (s, 1H), 8.50 (s, 1H), 8.36 (s, 1H), 7.89 (s, 1H), 7.86 (t, J=59.0 Hz, 1H), 7.74 (s, 1H), 7.66 (s, 1H), 4.53 (s, 2H), 4.05 (s, 3H), 2.90 (dt, J=12.2, 6.1 Hz, 1H), 0.95 (d, J=4.1 Hz, 6H).

Example 6: 6-isopropyl-9-(1-isobutyl-1H-pyrazole-4-yl)-10-methoxy-2-oxo-6,7-dihydro-2H-pyrido[2,1-a]phthalazine-3-carboxylic acid

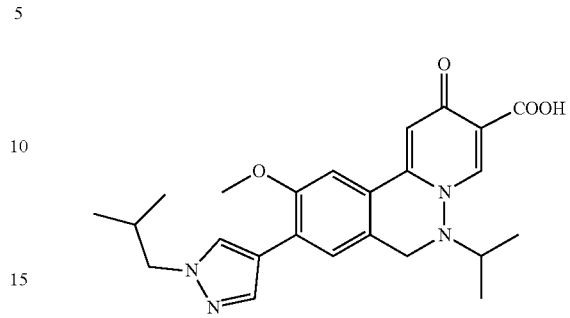

4-(4,4,5,5-tetramethyl-1,3,2-dioxaborolan-2-yl)-1H-pyrazole and isobutane iodide were taken as raw materials to give the title compound as a gray solid according to synthetic method in example 4.

MS (ESI, pos.ion) m/z: 437.2[M+H]$^+$; $^1$H NMR (400 MHz, CDCl$_3$) δ 8.62 (s, 1H), 8.07-7.73 (m, 2H), 7.45 (s, 1H), 7.28 (s, 1H), 7.11 (s, 1H), 4.41 (s, 2H), 4.02 (s, 3H), 3.97 (d, J=6.8 Hz, 2H), 3.02 (dt, J=11.7, 5.7 Hz, 1H), 2.47-2.06 (m, 1H), 1.01 (d, J=5.1 Hz, 6H), 0.95 (d, J=6.5 Hz, 6H).

Example 7: 9-(1-(4,4-Difluorocyclohexyl)-1H-pyrazol-4-yl)-6-isopropyl-10-methoxy-2-oxo-6,7-dihydro-2H-pyrido[2,1-a]phthalazine-3-carboxylic acid

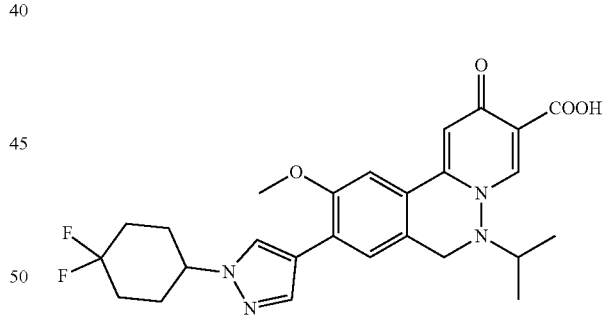

4-(4,4,5,5-Tetramethyl-1,3,2-dioxaborolan-2-yl)-1H-pyrazole and 4,4-difluorocyclohexyl methanesulfonate were taken as raw materials to give the title compound as a gray solid according to synthetic method in example 4.

MS (ESI, pos.ion) m/z: 499.3 [M+H]$^+$; $^1$H NMR (400 MHz, CDCl$_3$) δ 15.76 (s, 1H), 8.65 (s, 1H), 8.05 (s, 1H), 7.98 (s, 1H), 7.47 (s, 1H), 7.31 (s, 1H), 7.13 (s, 1H), 4.43 (s, 2H), 4.35 (s, 1H), 4.05 (s, 3H), 3.51 (s, 2H), 3.04 (dt, J=12.4, 6.2 Hz, 1H), 2.37-2.17 (m, 4H), 2.11-1.90 (m, 2H), 1.14-0.96 (m, 6H).

Example 8: 6-isopropyl-10-methoxy-2-oxo-9-(1-(2, 2,6,6-tetramethyltetrahydro-2H-pyran-4-yl)-1H-pyrazole-4-yl)-6,7-dihydro-2H-pyrido[2,1-a]phthalazine-3-carboxylic acid

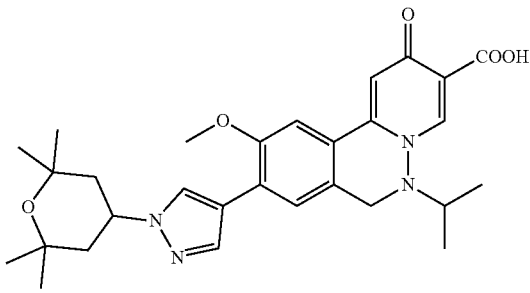 [SMILES: COc1cc2c(cc1-c1cnn(C3CC(C)(C)OC(C)(C)C3)c1)CN(C(C)C)n1cc(C(=O)O)c(=O)cc1-2]

4-(4,4,5,5-Tetramethyl-1,3,2-dioxaborolan-2-yl)-1H-pyrazole and 2,2,6,6-tetramethyltetrahydro-2H-pyran-4-methylmethanesulfonate were taken as raw materials to give the title compound as a gray solid according to synthetic method in example 4. MS (ESI, pos.ion) m/z: 521.6 [M+H]$^+$; $^1$H NMR (400 MHz, CDCl$_3$) δ 15.77 (s, 1H), 8.65 (s, 1H), 8.05 (s, 11H), 7.99 (s, 1H), 7.47 (s, 11H), 7.31 (s, 11H), 7.14 (s, 1H), 4.74 (t, J=12.6 Hz, 1H), 4.06 (s, 3H), 3.51 (s, 2H), 3.13-3.00 (m, 1H), 2.14 (d, J=9.7 Hz, 2H), 1.88 (t, J=12.4 Hz, 2H), 1.42 (s, 6H), 1.34 (s, 6H), 1.05 (d, J=5.3 Hz, 6H).

Example 9: 6-isopropyl-9-(1-isopropyl-5-methyl-1H-pyrazole-4-yl)-10-methoxy-2-oxo-6,7-dihydro-2H-pyrido[2,1-a]phthalazine-3-carboxylic acid

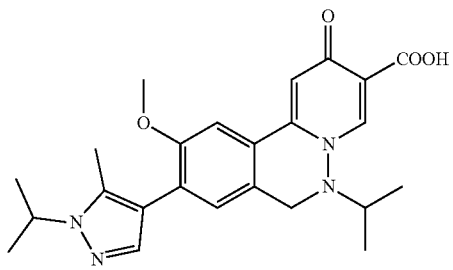 [SMILES: COc1cc2c(cc1-c1cnn(C(C)C)c1C)CN(C(C)C)n1cc(C(=O)O)c(=O)cc1-2]

3-Methyl-4-(4,4,5,5-tetramethyl-1,3,2-dioxaborolan-2-yl)-1H-pyrazole and 2-iodine propane were taken as raw materials to give the title compound as a gray solid according to synthetic method in example 4.

MS (ESI, pos.ion) m/z: 437.4 [M+1]$^+$; $^1$H NMR (400 MHz, CDCl$_3$) δ 15.77 (s, 1H), 8.65 (s, 1H), 7.70 (s, 1H), 7.29 (s, 1H), 7.25 (s, 1H), 7.15 (s, 1H), 4.56-4.46 (m, 1H), 4.42 (s, 2H), 3.96 (s, 3H), 3.11-2.97 (m, 1H), 2.37 (s, 3H), 1.56 (d, J=6.7 Hz, 6H), 1.04 (d, J=6.1 Hz, 6H).

Example 10: 9-(1-(2-carboxypropan-2-yl)-1H-pyrazole-4-yl)-6-isopropyl-10-methoxy-2-oxo-6,7-dihydro-2H-pyrido[2,1-a]phthalazine-3-carboxylic acid

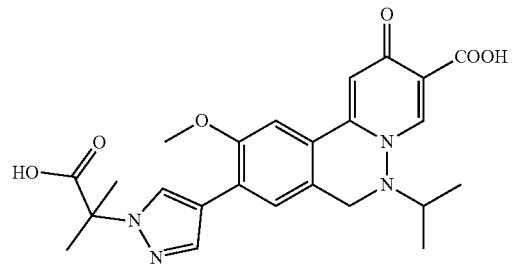 [SMILES: COc1cc2c(cc1-c1cnn(C(C)(C)C(=O)O)c1)CN(C(C)C)n1cc(C(=O)O)c(=O)cc1-2]

Step 1: ethyl 2-methyl-2-(4-(4,4,5,5-tetramethyl-1,3, 2-dioxaborolan-2-yl)-1H-pyrazole-1-yl) propionate

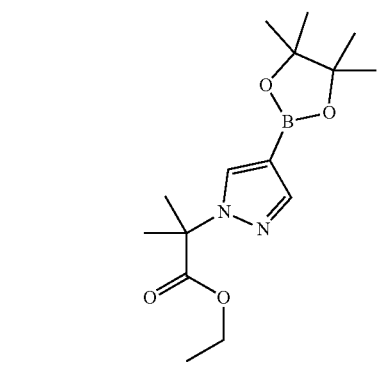 [SMILES: CCOC(=O)C(C)(C)n1cc(B2OC(C)(C)C(C)(C)O2)cn1]

To the reaction flask were added 4-(4,4,5,5-Tetramethyl-1,3,2-dioxaborolan-2-yl)-1H-pyrazole (1 g, 5.15 mmol), barium carbonate (2.52 g, 7.73 mmol), N,N-dimethylformamide (25 mL) and ethyl 2-bromoisobutyrate (0.9 mL, 6 mmol) in turn. The reaction solution was warmed to 90° C. and stirred for 17 h. After the reaction was finished, the reaction mixture was diluted with water (30 mL), then extracted with ethyl acetate (30 mL×3). The organic phases were combined and then washed with saturated sodium chloride solution and concentrated under reduced pressure. The residue was purified by silica gel column chromatography (PE/EA(V/V)=15/1) to give the title compound as a white solid (243 mg, 15%). MS (ESI, pos.ion) m/z: 309.3 [M+H]$^+$ Step 2: methyl 9-(1-(1-ethoxy-2-methyl-1-oxopropane-2-yl)-1H-pyrazole-4-yl)-6-isopropyl-10-methoxy-2-oxo-6,7-dihydro-2H-pyrido[2,1-a]phthalazine-3-carboxylate

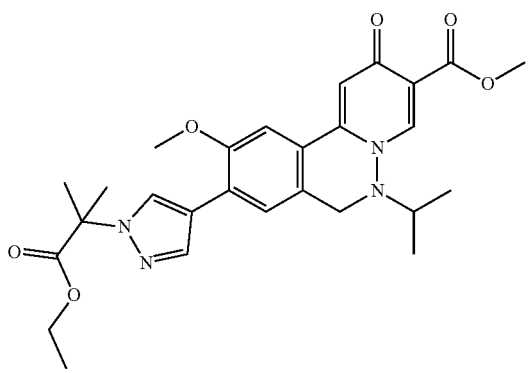 [SMILES: CCOC(=O)C(C)(C)n1cc(-c2cc3c(cc2OC)-c2cc(=O)c(C(=O)OC)cn2N(C(C)C)C3)cn1]

To the dry reaction flask were added methyl 9-trifluoromethanesulfonyl-6-isopropyl-10-methoxy-2-oxo-6,7-dihydro-2H-pyrido[2,1-a]phthalazine-3-formate (210 mg, 0.44 mmol), ethyl 2-methyl-2-(4-(4,4,5,5-tetramethyl-1,3,2-dioxaborolan-2-yl)-1H-pyrazole-1-yl) propionate (243 mg, 0.79 mmol), sodium bicarbonate (111 mg, 1.32 mmol), 1,1'-bis (diphenylphosphine) ferrocene palladium dichloride (II) dichloromethane complex (55 mg, 0.066 mmol), water (1 mL) and ethylene glycol dimethyl ether (5 mL) in turn. The reaction mixture was degassed and refilled with nitrogen for three times, warmed to 65° C. and stirred for 3 h under protection of nitrogen. Post processing: the reaction was concentrated in vacuo. The residue was purified by preparative TLC (DCM/MeOH(V/V)=16/1) to give the title compound as a brown solid (197 mg, 87.87%). MS (ESI, pos.ion) m/z: 509.1 [M+H]$^+$ Step 3: 9-(1-(2-carboxypropan-2-yl)-1H-pyrazole-4-yl)-6-isopropyl-10-methoxy-2-oxo-6,7-dihydro-2H-pyrido[2,1-a]phthalazine-3-carboxylic acid

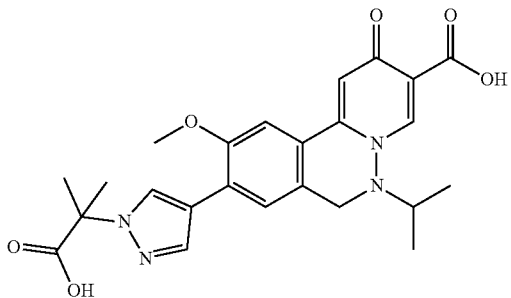 [SMILES: COc1cc2c(cc1-c1cnn(C(C)(C)C(=O)O)c1)CN(C(C)C)n1cc(C(=O)O)c(=O)cc1-2]

To the reaction flask were added Methyl 9-(1-(1-ethoxy-2-methyl-1-oxopropane-2-yl)-1H-pyrazole-4-yl)-6-isopropyl-10-methoxy-2-oxo-6,7-dihydro-2H-pyrido[2,1-a]phthalazine-3-carboxylate (176 mg, 0.35 mmol), methanol (5 mL) and tetrahydrofuran (1 mL). The mixture was stirred for dissolution, then lithium hydroxide monohydrate (73 mg, 1.740 mmol) and water (2 mL) were added. The mixture was stirred at rt for 5 h. Post processing: the solution was adjusted to pH 4 with 1M hydrochloric acid and filtered after stirring for 1 h. The filter cake was collected and dried to give the crude product as a brown yellow solid. The obtained solid crude was added with methanol (5 mL) and stirred at rt for 2 h and then filtered to give the title compound as a beige solid (125 mg 77.43%).

MS (ESI, pos.ion) m/z: 467.2[M+H]$^+$; $^1$H NMR (400 MHz, DMSO-d$_6$) δ 8.49 (s, 1H), 8.37 (s, 1H), 8.06 (s, 1H), 7.82 (s, 1H), 7.69 (s, 1H), 7.62 (s, 1H), 4.52 (s, 2H), 4.03 (s, 3H), 2.91 (dt, J=12.3, 6.2 Hz, 1H), 1.79 (s, 6H), 0.95 (d, J=3.8 Hz, 6H).

Example 11: 9-(1-(1-hydroxy-2-methylpropan-2-yl)-1H-pyrazol-4-yl)-6-isopropyl-10-methoxy-2-oxo-6,7-dihydro-2H-pyrido[2,1-a]phthalazine-3-carboxylic acid

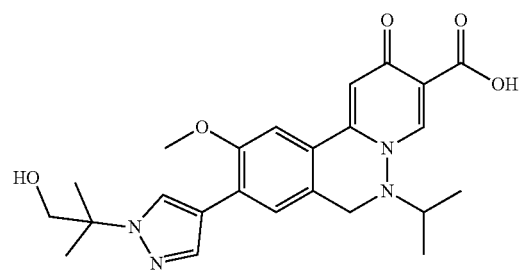 [SMILES: COc1cc2c(cc1-c1cnn(C(C)(C)CO)c1)CN(C(C)C)n1cc(C(=O)O)c(=O)cc1-2]

Step 1: 2-methyl-2-(4-(4,4,5,5-tetramethyl-1,3,2-dioxaborolan-2-yl)-1H-pyrazole-1-yl) propan-1-ol

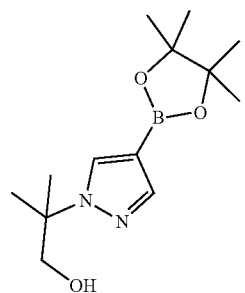 [SMILES: CC(C)(CO)n1cc(B2OC(C)(C)C(C)(C)O2)cn1]

To the reaction flask were added ethyl 2-methyl-2-(4-(4,4,5,5-tetramethyl-1,3,2-dioxaborolan-2-yl)-1H-pyrazole-1-yl) propionate (717 mg, 2.33 mmol) and tetrahydrofuran (10 mL) in turn. Sodium borohydride (550 mg, 14 mmol) was then added at 0° C. The reaction mixture was warmed to rt and stirred for 18 hours. Post processing: The reaction mixture was concentrated in vacuo to remove the solvents. The residue was added with water (15 mL) and ethyl acetate (15 mL). The mixture was separated. The aqueous phase was extracted with ethyl acetate (15 mL×2). The organic phases were combined. The combined organic phase was washed with saturated sodium chloride solution and concentrated in vacuo. The residue was purified by silica gel column chromatography (PE/EA(V/V)=4/1) to give the title compound as a white solid (365 mg, 59%). MS (ESI, pos.ion) m/z: 267.3[M+H]$^+$ Step 2: 9-(1-(1-hydroxy-2-methylpropyl-2-yl)-1H-pyrazole-4-yl)-6-isopropyl-10-methoxy-2-oxo-6,7-dihydro-2H-pyrido[2,1-a]phthalazine-3-carboxylic acid

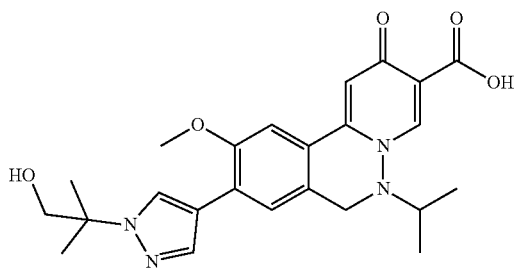 [SMILES: COc1cc2c(cc1-c1cnn(C(C)(C)CO)c1)CN(C(C)C)n1cc(C(=O)O)c(=O)cc1-2]

2-Methyl-2-(4-(4,4,5,5-tetramethyl-1,3,2-dioxaborolan-2-yl)-1H-pyrazole-1-yl)propan-1-ol were taken as raw material to give the title compound as a gray solid according to synthetic method in step 2-3 of example 4. MS (ESI, pos.ion) m/z: 453.4[M+H]$^+$; $^1$H NMR (400 MHz, DMSO-d$_6$) δ 8.47 (s, 1H), 8.27 (s, 1H), 8.02 (s, 1H), 7.79 (s, 1H), 7.69 (s, 1H), 7.62 (s, 1H), 5.00 (t, J=5.6 Hz, 1H), 4.51 (s, 2H), 4.02 (s, 3H), 3.61 (d, J=5.5 Hz, 2H), 2.91 (dt, J=12.3, 6.1 Hz, 1H), 1.50 (s, 6H), 0.95 (d, J=4.7 Hz, 6H).

Example 12: 6-tert-butyl-9-(1-(difluoromethyl)-1H-pyrazole-4-yl)-10-methoxy-2-oxo-6,7-dihydro-2H-pyrido[2,1-a]phthalazine-3-carboxylic acid

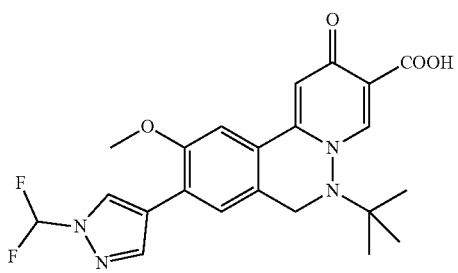

Step 1:
5-(benzyloxy)-2-bromo-4-methoxybenzaldehyde

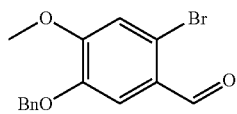 [SMILES: COc1cc(Br)c(C=O)cc1OCc1ccccc1]

To the reaction flask were added 2-bromo-5-hydroxy-4-methoxybenzaldehyde (20 g, 86.56 mmol), acetonitrile (200 mL), potassium carbonate (24 g, 173.1 mmol) and benzyl bromide (10.8 mL, 90.9 mmol) in turn. The mixture was warmed to 80° C. and stirred for 4 h. Post processing: The reaction solution was filtered and the filter residue was washed with with ethyl acetate (200 mL×3). The filtrate was concentrated in vacuo. The residue was stirred with methanol (80 mL) for 1 h, and then filtered. The filter cake was washed with methanol (10 mL×2) and dried to give the title compound as a white solid for the next step reaction. MS (ESI, pos.ion) m/z: 321.1, 323.1[M+H]$^+$ Step 2: N-(5-(benzyloxy)-2-bromo-4-methoxyphenyl)-2-methylpropane-2-amine

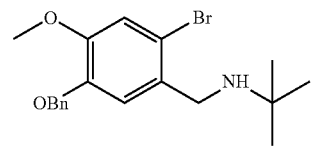 [SMILES: COc1cc(Br)c(CNC(C)(C)C)cc1OCc1ccccc1]

To the dry reaction flask were added 5-(benzyloxy)-2-bromo-4-methoxybenzaldehyde (4.73 g 14.74 mmol), methanol (90 mL), tert-butylamine (3.77 g, 51.5 mmol), and acetic acid (177 mg, 2.94 mmol). The reaction mixture was warmed to 60° C. and stirred until all solids were dissolved. Then the mixture was continuously stirred for 2 h, transfered to 0° C., and sodium borohydride (1.74 g 44.2 mmol) was added in batches, and then the mixture was warmed to rt and stirred for 3 h. Post processing: the mixture was concentrated in vacuo to remove the solvent, the residue was diluted with ethyl acetate (60 mL) and water (50 mL). The resulting mixture was separated and the upper organic phase was collected. The aqueous phase was extracted with ethyl acetate (60 mL). Organic phases were combined and the combined organic phase were washed with saturated sodium chloride solution, dried over anhydrous sodium sulfate, filtered and concentrated in vacuo to give the title compoud as a colourless oil for next step reaction. MS (ESI, pos.ion) m/z: 378.1 [M+H]$^+$ Step 3: N-(5-(benzyloxy)-2-bromo-4-methoxybenzyl)-N-(tert-butyl) nitrosamide

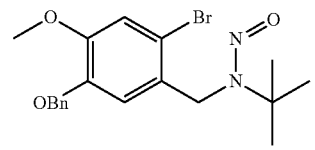 [SMILES: COc1cc(Br)c(CN(N=O)C(C)(C)C)cc1OCc1ccccc1]

N-(5-(benzyloxy)-2-bromo-4-methoxyphenyl)-2-methylpropane-2-amine (6.748 g, 17.84 mmol), tetrahydrofuran (70 mL), sodium nitrite aqueous solution (13.5 mL)(3.14 g, 44.59 mmol) and acetic acid (2.65 mL, 45.4 mmol) were added to the dry reaction bottle in order. The reaction mixture was warmed to 50° C. and stirred for 8 h. Post processing: The reaction mixture was concentrated in vacuo to remove the solvent. The residue was dissolved with ethyl acetate (60 mL), washed with saturated sodium chloride solution, dried over anhydrous sodium sulfate, filtered. The filtrate was concentrated in vacuo. The residue was purified by silica gel column chromatography (PE/EA(V/V)=10/1) to give the title compound as light yellow oil (6.69 g, 92.1%).

Step 4: 1-(5-(benzyloxy)-2-bromo-4-methoxyphenyl)-1-(tert-butyl) hydrazine

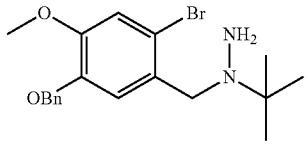 [SMILES: COc1cc(Br)c(CN(N)C(C)(C)C)cc1OCc1ccccc1]

To the dry reaction flask were added N-(5-(benzyloxy)-2-bromo-4-methoxybenzyl)-N-(tert-butyl) nitrosamide (6.66 g, 16.4 mmol), ethanol (13 mL) and trifluoroacetic acid (40 mL). The reaction mixture was warmed to 50° C., added with zinc powder (5.35 g, 81.7 mmol) in batches and stirred for 2 h. Post processing: the reaction mixture was filtered to remove the solid, and the filtrate was concentrated in vacuo, the residue was directly used in next step reaction. MS (ESI, pos.ion) m/z: 393.0 [M+H]$^+$

Step 5: ethyl 1-((5-(benzyloxy)-2-bromo-4-methoxyphenyl) (tert-butyl) amino)-4-oxo-1,4-dihydropyridine-3-formate

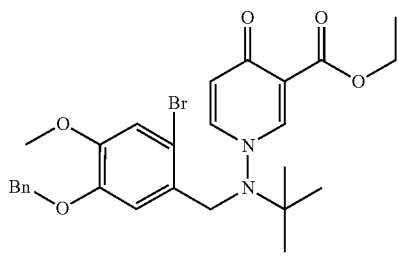 [SMILES: CCOC(=O)c1cn(N(Cc2cc(OCc3ccccc3)c(OC)cc2Br)C(C)(C)C)ccc1=O]

1-(5-(Benzyloxy)-2-bromo-4-methoxyphenyl)-1-(tert-butyl) hydrazine (6.43 g, 16.3 mmol) was dissolved in ethanol (70 mL), then ethyl 4-oxopyran-3-formate (2.75 g, 16.4 mmol) was added. The reaction mixture was warmed to reflux and stirred for 15 h. Post processing: The reaction mixture was concentrated in vacuo to remove the solvent. The residue was purified by silica gel column chromatography (DCM/MeOH(V/V)=50/1) to give the title compound as a brown red solid (4.41 g, 49.7%). MS (ESI, pos.ion) m/z: 543.3[M+H]$^+$

Step 6: 9-(benzyloxy)-6-(tert-butyl)-10-methoxy-2-oxo-6,7-dihydro-2H-pyrido[2,1-a]phthalazine-3-carboxylic acid

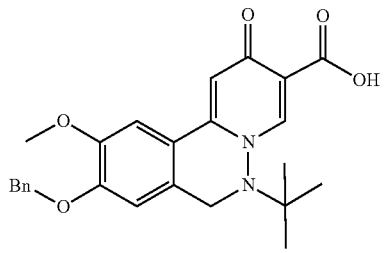 [SMILES: COc1cc2c(cc1OCc1ccccc1)CN(C(C)(C)C)n1cc(C(=O)O)c(=O)cc1-2]

To the reaction flask were added ethyl 1-((5-(Benzyloxy)-2-bromo-4-methoxyphenyl) (tert-butyl) amino)-4-oxo-1,4-dihydropyridine-3-formate (4.414 g, 8.123 mmol), palladium bromide (218 mg, 0.811 mmol), potassium acetate (1.61 g 16.2 mmol) and N, N-dimethylacetamide (50 mL). The reaction solution was warmed to 130° C. and stirred for 8 h. Post processing: the reaction mixture was filtered through celite pad, and the filtrate was diluted with water (80 mL) and ethyl acetate (80 mL). The aqueous phase was extracted with ethyl acetate (80 mL×2). The combined organic phases were washed with saturated sodium chloride solution, dried over anhydrous sodium sulfate, and filtered. The filtrate was concentrated under reduced pressure. The concentrated residue was dissolved in methanol (40 mL) and tetrahydrofuran (5 mL). Lithium hydroxide monohydrate (1.7 g, 41 mmol) and water (9 mL) were added and the resulting mixture was stirred for 4 h. Post processing: the mixture was concentrated in vacuo to remove most of the solvent. Ethyl acetate (80 mL) and water (50 mL) were added, the solution was adjusted to pH 4 with 1M hydrochloric acid and the solid was precipitated. After suction filtration, the filter cake was obtained as the most of title compound (a yellow solid, 1.17 g). The filtrate was collected and separated. The organic phase was dried over anhydrous sodium sulfate, filtered, and concentrated under reduced pressure. The residue was stirred in methanol (10 mL) for 1 h and filtered to give another part of the title compound as a yellow solid (686 mg). (totally 1.9 g, 53.01%). MS (ESI, pos.ion) m/z: 435.4[M+H]$^+$

Step 7: 6-(tert-butyl)-9-hydroxy-10-methoxy-2-oxo-6,7-dihydro-2H-pyrido[2,1-a]phthalazine-3-carboxylic acid

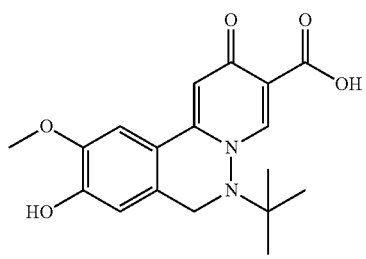

9-(Benzyloxy)-6-(tert-butyl)-10-methoxy-2-oxo-6,7-dihydro-2H-pyrido[2,1-a]phthalazine-3-carboxylic acid (636 mg 1.464 mmol), methanol (25 mL), palladium/carbon (311 mg, 0.292 mmol, wt %: 10%) and dichloromethane (25 mL) were added in order to the reaction bottle. The reaction mixture was degassed and refilled with nitrogen for three times and stirred under an atmosphere of hydrogen for 12 h. Post processing: stirring was stopped and suction filtration was performed. The filter cake was washed with the mixture of dichloromethane and methanol (DCM/MeOH(V/V)=2/1, 600 mL). The obtained filtrate was concentrated in vacuo to give the title compound as a brownish gray solid (381 mg, 76%). MS (ESI, pos.ion) m/z: 345.1[M+H]$^+$ Step 8: 6-(tert-butyl)-10-methoxy-2-oxo-9-(((trifluoromethyl)sulfonyl)oxy)-6,7-dihydro-2H-pyrido[2,1-a]phthalazine-3-carboxylic acid

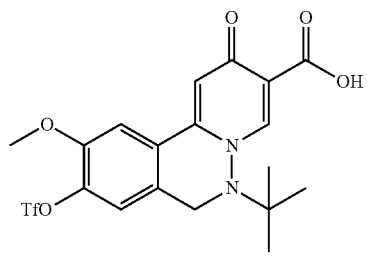 [SMILES: COc1cc2c(cc1O)CN(C(C)(C)C)n1cc(C(=O)O)c(=O)cc1-2]

6-(tert-Butyl)-9-hydroxy-10-methoxy-2-oxo-6,7-dihydro-2H-pyrido[2,1-a]phthalazine-3-carboxylic acid (578 mg, 1.678 mmol), dichloromethane (15 mL) and 1,8-diazabicyclic[5.4.0]undecano-7-ene (0.65 g, 4.2 mmol) were added to the reaction bottle which was then transfered to 0° C. 1,1,1-Trifluoromethyl-N-phenyl-N-((trifluoromethyl)sulfonyl) mesosulfonamide (1.2 g, 3.4 mmol) was added and the reaction mixture was warmed to rt and stirred for 12 h. Post processing: the solution was adjusted to pH 6 with 1 M hydrochloric acid, the filtrate was collected and separated. The combined organic phase was dried over anhydrous sodium sulfate, and filtered. The filtrate was concentrated in vacuo, and the residue was purified by silica gel column chromatography (DCM/MeOH(V/V)=30/1) to give a brown-yellow viscous crude product. The obtained crude product was added with methanol (5 mL) and stirred at rt for 1 h and then filtered by suction to give the title compound as a white solid (317 mg, 40%). MS (ESI, pos.ion) m/z: 477.1[M+H]$^+$ Step 9: 6-tert-butyl-9-(1-(difluoromethyl)-1H-pyrazole-4-yl)

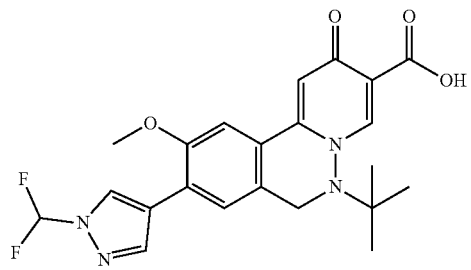 [SMILES: COc1cc2c(cc1-c1cnn(C(F)F)c1)CN(C(C)(C)C)n1cc(C(=O)O)c(=O)cc1-2]

6-(tert-Butyl)-10-methoxy-2-oxo-9-((trifluoromethyl) sulfonyl) oxy)-6,7-dihydro-2H-pyrido[2,1-a]phthalazine-3-carboxylic acid (155 mg, 0.325 mmol), 1-difluoromethyl-4-(4,4,5,5-tetramethyl-1,3,2-dioxaborolan-2-yl)-1H-pyrazole (143 mg, 0.586 mmol), sodium bicarbonate (82 mg 0.975 mmol), 1,1'-bis (diphenylphosphine) ferrocene palladium dichloride (II) dichloromethane complex (40 mg, 0.048 mmol), water (1 mL) and ethylene glycol dimethyl ether (5 mL) were added to the dry reaction bottle in order. The reaction mixture was degassed and refilled with nitrogen for three times, then warmed to 65° C. and stirred for 4 h under protection of nitrogen. Post processing: the mixture was concentrated in vacuo. The residue was purified by silica gel column chromatography (DCM/MeOH(V/V)=30/ 1) to give a brown-black crude product. The obtained crude product was added with methanol (4 mL) and stirred at rt for 1 h and then filtered by suction to give the title compound as a gray solid (56 mg, 38.73%). MS (ESI, pos.ion) m/z: 445.3 [M+H]$^+$; $^1$H NMR (600 MHz, DMSO-d$_6$) δ 8.71 (s, 1H), 8.50 (s, 1H), 8.36 (s, 1H), 8.02-7.75 (m, 2H), 7.70 (s, 1H), 7.65 (s, 1H), 4.63 (d, J=16.9 Hz, 1H), 4.56 (d, J=16.8 Hz, 1H), 4.04 (s, 3H), 0.95 (s, 9H).

Example 13: 6-(tert-butyl)-9-(1-isopropyl-1H-pyrazol-4-yl)-10-methoxy-2-oxo-6,7-dihydro-2H-pyrido [2, 1-a]phthalazine-3-carboxylic acid

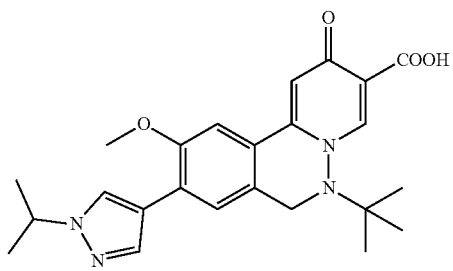 [SMILES: COc1cc2c(cc1-c1cnn(C(C)C)c1)CN(C(C)(C)C)n1cc(C(=O)O)c(=O)cc1-2]

6-(tert-butyl)-10-Methoxy-2-oxo-9-(((trifluoromethyl) sulfonyl)oxy)-6,7-dihydro-2H-pyrid o[2,1-a]phthalazine-3-carboxylic acid and 1-isopropyl-4-(4,4,5,5-tetramethyl-1,3,2-dioxaborolane-2-yl)-1H-pyrazole were taken as raw materials to give the title compound as a brownish yellow solid according to synthetic method in step 9 of example 12.

MS (ESI, pos.ion) m/z: 437.1[M+H]; $^1$H NMR (400 MHz, CDCl$_3$) δ 15.77 (s, 1H), 8.63 (s, 1H), 8.00 (s, 1H), 7.96 (s, 1H), 7.42 (s, 1H), 7.23 (s, 1H), 7.10 (s, 1H), 4.61-4.52 (m, 1H), 4.49 (d, J=6.2 Hz, 2H), 4.01 (s, 3H), 1.57 (d, J=6.7 Hz, 6H), 1.02 (s, 9H).

Example 14: 6-cyclopropyl-9-(1-isopropyl-1H-pyrazol-4-yl)-10-methoxy-2-oxo-6,7-dihydro-2H-pyrido [2,1-a]phthalazine-3-carboxylic acid

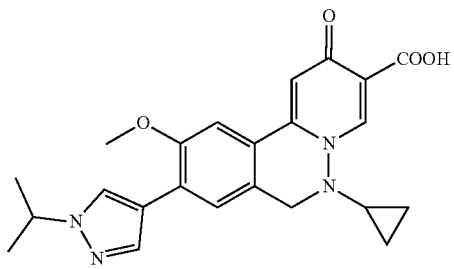 [SMILES: COc1cc2c(cc1-c1cnn(C(C)C)c1)CN(C1CC1)n1cc(C(=O)O)c(=O)cc1-2]

5-(benzyloxy)-2-bromo-4-methoxybenzaldehyde and cyclopropylamine were taken as raw material to give 6-cyclopropyl-10-methoxy-2-oxo-9-(((trifluoromethyl)sulfonyl) oxy)-6,7-dihydro-2H-pyrido[2,1-a]phthalazine-3-carboxylic acid according to synthetic method in step 2-8 of example 12. Then 6-cyclopropyl-10-methoxy-2-oxo-9-(((trifluoromethyl)sulfonyl)oxy)-6,7-dihydro-2H-pyrido[2, 1-a]phthalazine-3-carboxylic acid and 1-isopropyl-4-(4,4,5, 5-tetramethyl-1,3,2-dioxaborolane-2-yl)-1H-pyrazole were taken as raw material to give the title compound as a brownish white solid according to synthetic method in step 9 of example 12.

MS (ESI, pos.ion) m/z: 421.1 [M+H]⁺; ¹H NMR (400 MHz, CDCl₃) δ 15.81 (s, 1H), 8.55 (s, 1H), 8.01 (s, 1H), 7.97 (s, 1H), 7.50 (s, 1H), 7.32 (s, 1H), 7.15 (s, 1H), 4.56 (dt, J=13.4, 6.7 Hz, 1H), 4.40 (s, 2H), 4.03 (s, 3H), 2.50-2.42 (m, 1H), 1.58 (s, 31H), 1.56 (s, 31H), 0.88 (s, 2H), 0.60 (d, J=5.8 Hz, 2H).

Example 15: 6-cyclobutyl-9-(1-isopropyl-1H-pyrazol-4-yl)-10-methoxy-2-oxo-6,7-dihydro-2H-pyrido[2,1-a]phthalazine-3-carboxylic acid

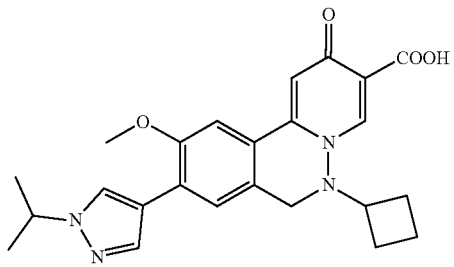 [SMILES: COc1cc2c(cc1-c1cnn(C(C)C)c1)CN(C1CCC1)n1cc(C(=O)O)c(=O)cc1-2]

5-(benzyloxy)-2-bromo-4-methoxybenzaldehyde and cyclobutylamine were taken as raw material to give 6-cyclobutyl-10-methoxy-2-oxo-9-(((trifluoromethyl)sulfonyl)oxy)-6,7-dihydro-2H-pyrido[2,1-a]phthalazine-3-carboxylic acid according to synthetic method in step 2-8 of example 12. Then 6-cyclobutyl-10-methoxy-2-oxo-9-(((trifluoromethyl)sulfonyl)oxy)-6,7-dihydro-2H-pyrido[2,1-a]phthalazine-3-carboxylic acid and 1-isopropyl-4-(4,4,5,5-tetramethyl-1,3,2-dioxaborolan-2-yl)-1H-pyrazole were taken as raw material to give the target product as a brownish white solid according to synthetic method in step 9 of example 12. MS (ESI, pos.ion) m/z: 435.0 [M+H]⁺; ¹H NMR (400 MHz, CDCl₃) δ 15.80 (s, 1H), 8.65 (s, 1H), 8.00 (s, 1H), 7.94 (s, 1H), 7.40 (s, 1H), 7.26 (s, 1H), 7.14 (s, 1H), 4.55 (d, J=5.8 Hz, 1H), 4.27 (s, 2H), 4.02 (s, 3H), 3.45-3.35 (m, 1H), 1.97 (dd, J=18.8, 9.4 Hz, 2H), 1.83-1.69 (m, 4H), 1.56 (d, J=6.2 Hz, 6H).

Example 16: 9-(1-cyclopropyl-1H-pyrazole-4-yl)-6-isopropyl-10-methoxy-2-oxo-6,7-dihydro-2H-pyrido[2,1-a]phthalazine-3-carboxylic acid

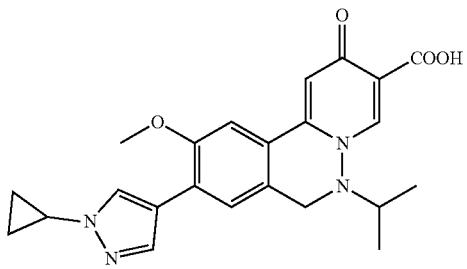 [SMILES: COc1cc2c(cc1-c1cnn(C3CC3)c1)CN(C(C)C)n1cc(C(=O)O)c(=O)cc1-2]

Methyl 6-isopropyl-10-methoxy-2-oxo-9-(((trifluoromethyl)sulfonyl)oxy)-6,7-dihydro-2H-pyrido[2,1-a]phthalazine-3-formate and 1-cyclopropyl-4-(4,4,5,5-tetramethyl-1,3,2-dioxaborolane-2-yl)pyrazole were taken as raw material to give the target product as a grayish white solid according to synthetic method in step 13 of example 1.

MS (ESI, pos.ion) m/z: 421.0 [M+H]⁺; ¹H NMR (400 MHz, DMSO-d₆) δ 8.48 (s, 1H), 8.29 (s, 1H), 7.98 (s, 1H), 7.78 (s, 1H), 7.69 (s, 1H), 7.63 (s, 1H), 4.50 (s, 2H), 4.03 (s, 3H), 3.79 (dq, J=11.1, 3.8 Hz, 1H), 2.91 (dt, J=12.3, 6.1 Hz, 1H), 1.12-1.05 (m, 2H), 1.04-0.98 (m, 2H), 0.98-0.90 (m, 6H).

Example 17: 9-(1-cyclobutyl-1H-pyrazole-4-yl)-6-isopropyl-10-methoxy-2-oxo-6,7-dihydro-2H-pyrido[2,1-a]phthalazine-3-carboxylic acid

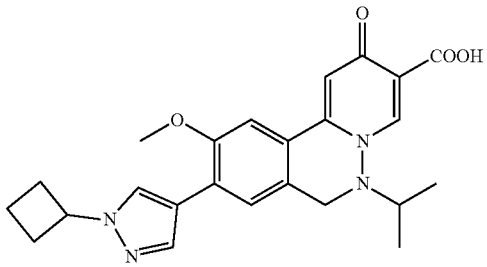 [SMILES: COc1cc2c(cc1-c1cnn(C3CCC3)c1)CN(C(C)C)n1cc(C(=O)O)c(=O)cc1-2]

Methyl 6-isopropyl-10-methoxy-2-oxo-9-(((trifluoromethyl)sulfonyl)oxy)-6,7-dihydro-2H-pyrido[2,1-a]phthalazine-3-formate and 1-cyclobutyl-4-(4,4,5,5-tetramethyl-1,3,2-dioxaborolane-2-yl)pyrazole were taken as raw material to give the target product as a grayish white solid according to synthetic method in step 13 of example 1. MS (ESI, pos.ion) m/z: 435.1[M+H]⁺; ¹H NMR (400 MHz, DMSO-d₆) δ 8.48 (s, 1H), 8.31 (s, 1H), 8.04 (s, 1H), 7.79 (s, 1H), 7.68 (s, 1H), 7.61 (s, 1H), 4.98-4.76 (m, 1H), 4.51 (s, 2H), 4.02 (s, 31H), 2.90 (dt, J=12.1, 6.0 Hz, 1H), 2.47-2.32 (m, 4H), 1.94-1.61 (m, 2H), 0.94 (d, J=3.2 Hz, 6H).

Example 18: 9-(1-cyclopentyl-1H-pyrazole-4-yl)-6-isopropyl-10-methoxy-2-oxo-6,7-dihydro-2H-pyrido[2,1-a]phthalazine-3-carboxylic acid

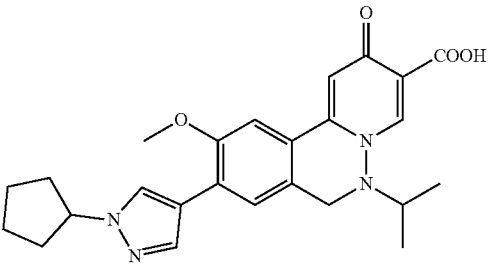 [SMILES: COc1cc2c(cc1-c1cnn(C3CCCC3)c1)CN(C(C)C)n1cc(C(=O)O)c(=O)cc1-2]

Methyl 6-isopropyl-10-methoxy-2-oxo-9-(((trifluoromethyl)sulfonyl)oxy)-6,7-dihydro-2H-pyrido[2,1-a]phthalazine-3-formate and 1-cyclopentyl-4-(4,4,5,5-tetramethyl-1,3,2-dioxaborolan-2-yl)pyrazole were taken as raw material to give the target product as a grayish white solid according to synthetic method in step 13 of example 1. MS (ESI, pos.ion) m/z: 449.1[M+H]⁺; ¹H NMR (400 MHz, CDCl₃) δ 15.76 (s, 1H), 8.62 (s, 1H), 8.00 (s, 1H), 7.94 (s, 1H), 7.43 (s, 1H), 7.27 (s, 1H), 7.10 (s, 1H), 4.78-4.64 (m, 1H), 4.40 (s, 2H), 4.02 (s, 3H), 3.01 (dt, J=12.4, 6.2 Hz, 11H), 2.21 (dd, J=12.9, 5.7 Hz, 2H), 2.07 (dd, J=12.7, 6.8 Hz, 2H), 1.98-1.86 (m, 2H), 1.80-1.70 (m, 2H), 1.02 (d, J=5.9 Hz, 6H).

Example 19: 6-isopropyl-10-methoxy-2-oxo-9-(1-(tetrahydro-2H-pyran-4-yl)-1H-pyrazole-4-yl)-6,7-dihydro-2H-pyrido[2,1-a]phthalazine-3-carboxylic acid

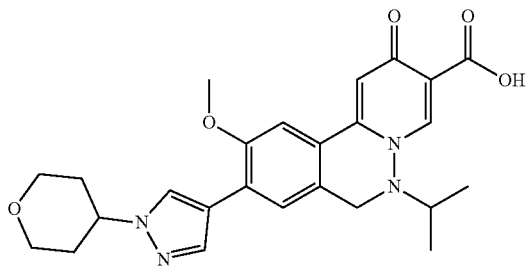 [SMILES: COc1cc2c(cc1-c1cnn(C3CCOCC3)c1)CN(C(C)C)n1cc(C(=O)O)c(=O)cc1-2]

Methyl 6-isopropyl-10-methoxy-2-oxo-9-(((trifluoromethyl)sulfonyl)oxy)-6,7-dihydro-2H-pyrido[2,1-a]phthalazine-3-formate and 1-tetrahydropyran-4-yl-4-(4,4,5,5-tetramethyl-1,3,2-dioxaborolane-2-yl)pyrazole were taken as raw material to give the target product as a grayish white solid according to synthetic method in step 13 of example 1. MS (ESI, pos.ion) m/z: 465.1[M+H]$^+$; $^1$H NMR (400 MHz, deuterated pyridine) δ 8.85 (s, 1H), 8.55 (s, 1H), 8.49 (s, 1H), 7.87 (s, 1H), 7.62 (s, 1H), 7.51 (s, 1H), 4.57-4.45 (m, 3H), 4.11-4.03 (m, 5H), 3.46 (td, J=12.1, 1.6 Hz, 2H), 2.92 (dt, J=12.4, 6.2 Hz, 1H), 2.28 (qd, J=12.3, 4.4 Hz, 2H), 2.06 (dd, J=12.5, 2.1 Hz, 2H), 0.84 (d, J=5.7 Hz, 6H).

Example 20: 6-isopropyl-10-methoxy-9-(1-(oxetan-3-yl)1H-pyrazole-4-yl)-2-oxo-6,7-dihydro-2H-pyrido[2,1-a]phthalazine-3-carboxylic acid

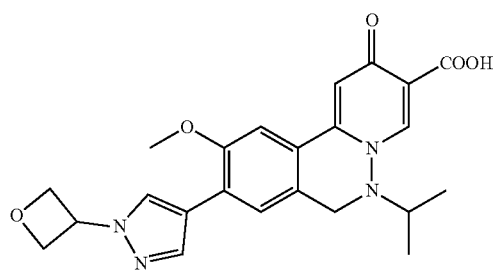 [SMILES: COc1cc2c(cc1-c1cnn(C3COC3)c1)CN(C(C)C)n1cc(C(=O)O)c(=O)cc1-2]

Methyl 6-isopropyl-10-methoxy-2-oxo-9-(((trifluoromethyl)sulfonyl)oxy)-6,7-dihydro-2H-pyrido[2,1-a]phthalazine-3-carboxylic acid and 1-(oxetan-3-yl)-4-yl-4-(4,4,5,5-tetramethyl-1,3,2-dioxaborolane-2-yl)pyrazole were taken as raw material to give the target product as a grayish white solid according to synthetic method in step 13 of example 1. MS (ESI, pos.ion) m/z: 437.1[M+H]$^+$; $^1$H NMR (400 MHz, DMSO-d$_6$) δ 8.48 (s, 1H), 8.38 (s, 1H), 8.15 (s, 1H), 7.80 (s, 1H), 7.68 (s, 1H), 7.60 (s, 11H), 5.65 (dd, J=15.8, 9.0 Hz, 1H), 4.94 (d, J=6.4 Hz, 4H), 4.50 (s, 2H), 4.02 (s, 3H), 2.92 (dt, J=12.4, 6.1 Hz, 1H), 0.95 (s, 6H).

Example 21: 9-(1-(1-(tert-butoxycarbonyl)piperidin-4-yl)-1H-pyrazole-4-yl)-6-isopropyl-10-methoxy-2-oxo-6,7-dihydro-2H-pyrido[2,1-a]phthalazine-3-carboxylic acid

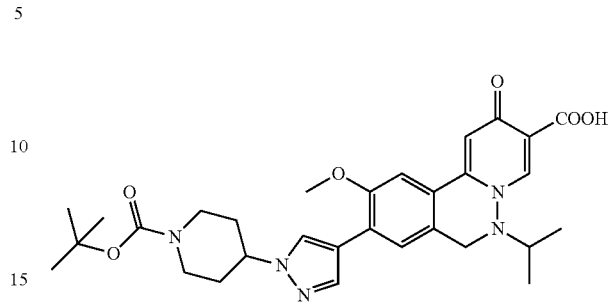

Methyl 6-isopropyl-10-methoxy-2-oxo-9-(((trifluoromethyl)sulfonyl)oxy)-6,7-dihydro-2H-pyrido[2,1-a]phthalazine-3-formate and tert-butyl 4[4-(4,4,5,5-tetramethyl-1,3,2-dioxaborolan-2-yl)pyrazol-1-yl]piperidine-1-formate were taken as raw material to give the target product as a grayish white solid according to synthetic method in step 13 of example 1. MS (ESI, pos.ion) m/z: 564.1 [M+H]$^+$; $^1$H NMR (400 MHz, DMSO-d$_6$) δ 8.47 (s, 1H), 8.29 (s, 1H), 8.01 (s, 1H), 7.76 (s, 1H), 7.66 (s, 1H), 7.59 (s, 1H), 4.49 (s, 2H), 4.40 (dd, J=15.1, 7.9 Hz, 1H), 4.07 (d, J=11.4 Hz, 2H), 4.02 (s, 3H), 2.92 (dt, J=12.2, 6.1 Hz, 3H), 2.02 (d, J=11.2 Hz, 2H), 1.83 (qd, J=12.2, 4.1 Hz, 2H), 1.42 (s, 9H), 0.95 (d, J=3.6 Hz, 6H).

Example 22: 9-(1-(1-(cyclopropanesulfonyl) piperidin-4-yl)-1H-pyrazole-4-yl)-6-isopropyl-10-methoxy-2-oxo-6,7-dihydro-2H-pyrido[2,1-a]phthalazine-3-carboxylic acid

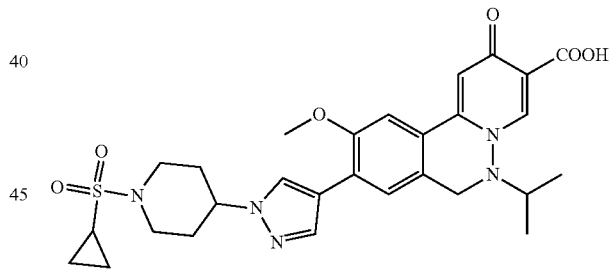

Step 1: 4-(4-(4,4,5,5-tetramethyl-1,3,2-dioxaborolane-2-yl)-1H-pyrazol-1-yl)piperidine

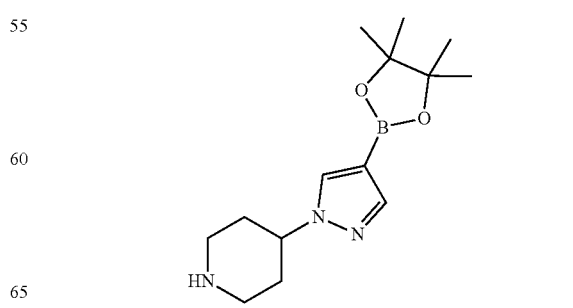

tert Butyl 4[4-(4,4,5,5-tetramethyl-1,3,2-dioxaborolan-2-yl)-pyrazol-1-yl]piperidine-1-formate (1 g, 2.650 mmol) was dissolved in dichloromethane (5 mL), and trifluoroacetate (5 mL) was added, the reaction mixture was stirred for 2 h. Post processing: the reaction mixture was concentrated and the residue was diluted with toluene (10 mL), continuously distilled under reduced pressure to remove residual TFA. The residue was title compound as colourless oil (1.4 g 5.1 mmol). MS (ESI, pos.ion) m/z: 278.2 [M+H]+.

Step 2: 1-(cyclopropylsulfonyl)-4-(4-(4,4,5,5-tetramethyl-1,3,2-dioxaborolane-2-yl)-1H-pyrazole-1-yl)pipe ridine

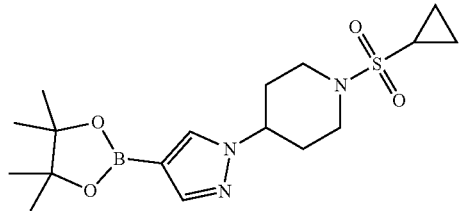 [SMILES: CC1(C)OB(c2cnn(C3CCN(S(=O)(=O)C4CC4)CC3)c2)OC1(C)C]

4-(4-(4,4,5,5-Tetramethyl-1,3,2-dioxaborolane-2-yl)-1H-pyrazole-1-yl)piperidine (700 mg, 2.5 mmol) was dissolved in DCM (12 mL) and methanol (3 mL) at −10° C., and triethylamine (3.54 mL, 25.3 mmol) was added, then cyclopropylsulfonyl chloride (0.643 mL, 6.31 mmol) was added slowly. The resulting solution was stirred at room temperature for 3 h. Post processing: the reaction was quenched with saturated ammonium chloride (20 mL) and was extracted with DCM (10 mL×2). The organic phases were combined, the combined organic phases were washed with saturated saline (20 mL), dried over anhydrous sodium sulfate, filtered and concentrated to give the title compound as a light yellow solid (0.89 g, 2.3 mmol, 92%). MS (ESI, pos.ion) m/z: 382.1 [M+H]+.

Step 3: 9-(1-(1-cyclopropanesulfonyl)piperidin-4-yl)-1H-pyrazole-4-yl)-6-isopropyl-10-methoxy-2-oxo-6,7-dihydro-2H-pyrido[2,1-a]phthalazine-3-carboxylic acid

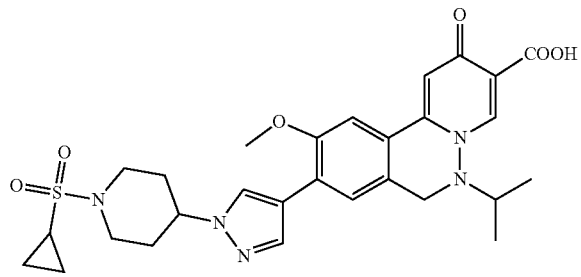 [SMILES: COc1cc2c(cc1-c1cnn(C3CCN(S(=O)(=O)C4CC4)CC3)c1)CN(C(C)C)n1cc(C(=O)O)c(=O)cc1-2]

Ethyl 6-isopropyl-10-methoxy-2-oxo-9-(((trifluoromethyl)sulfonyl)oxy)-6,7-dihydro-2H-pyrido[2,1-a]phthalazine-3-formte and 1-(cyclopropylsulfonyl)-4-(4-(4,4,5,5-tetramethyl-1,3,2-dioxaborolan-2-yl)-1H-pyrazole-1-yl)piperi dine were taken as raw material according to the synthetic method in step 13 of example 1 to give the target product as a grayish white solid. MS (ESI, pos.ion) m/z: 568.6[M+H]+; 1H NMR (400 MHz, CD3OD) δ 8.41 (s, 1H), 7.91 (s, 1H), 7.78 (s, 1H), 7.32 (s, 1H), 7.19 (s, 1H), 6.97 (s, 1H), 3.84 (s, 3H), 3.70 (d, J=13.4 Hz, 2H), 3.10 (s, 1H), 2.91-2.77 (m, 4H), 2.18 (dt, J=17.7, 6.4 Hz, 2H), 2.03 (t, J=14.8 Hz, 3H), 1.96-1.89 (m, 2H), 0.94 (dd, J=8.7, 5.8 Hz, 4H), 0.81 (d, J=5.7 Hz, 6H).

Example 23: 9-(1-(1,1-dioxotetrahydro-2H-thiapyran-4-yl)-1H-pyrazole-4-yl)-6-isopropyl-10-methoxy-2-oxo-6,7-dihydro-2H-pyrido[2,1-a]phthalazine-3-carboxylic acid

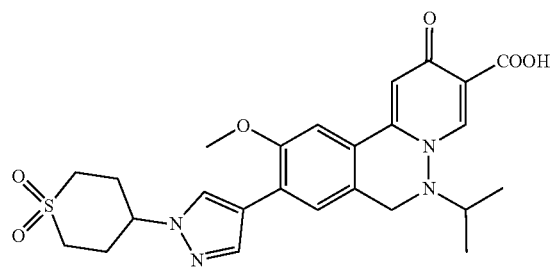 [SMILES: COc1cc2c(cc1-c1cnn(C3CCS(=O)(=O)CC3)c1)CN(C(C)C)n1cc(C(=O)O)c(=O)cc1-2]

Methyl 6-isopropyl-10-methoxy-2-oxo-9-(((trifluoromethyl)sulfonyl)oxy)-6,7-dihydro-2H-pyrido[2,1-a]phthalazine-3-formate and 4-[4-(4,4,5,5-tetramethyl-1,3,2-dioxaborolan-2-yl)pyrazol-1-yl]thiopyran-1,1-dioxide were taken as raw material according to the synthetic method in step 13 of example 1 to give the target product as a grayish white solid. MS (ESI, pos.ion) m/z: 513.2 [M+H]+; 1H NMR (400 MHz, CDCl3) δ 8.56 (s, 1H), 8.03 (s, 1H), 7.91 (s, 1H), 7.40 (s, 11H), 7.29 (s, 1H), 7.09 (s, 1H), 4.36 (s, 2H), 3.98 (s, 3H), 3.16 (s, 4H), 2.94 (d, J=5.8 Hz, 1H), 2.57 (d, J=34.5 Hz, 4H), 1.17 (s, 1H), 0.95 (s, 6H).

Example 24: 6-isopropyl-10-methoxy-2-oxo-9-(1-(cyclopropanesulfonyl)-1H-pyrido-4-yl)-6,7-dihydropyrido[2,1-a]phthalazine-3-carboxylic acid

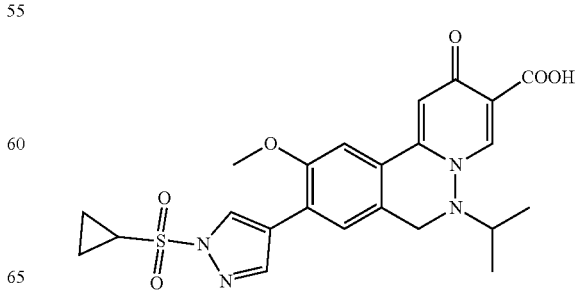

81

Step 1: 1-(cyclopropylsulfonyl)-4-(4,4,5,5-tetramethyl-1,3,2-dioxaborolan-2-yl)-1H-pyrazole

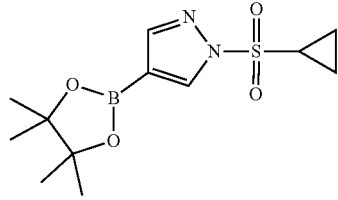 [SMILES: CC1(C)OB(c2cnn(S(=O)(=O)C3CC3)c2)OC1(C)C]

4-(4,4,5,5-Tetramethyl-1,3,2-dioxaborolan-2-yl)-1H-pyrazole (3.0 g, 15 mmol), DMF (30 mL), NaH (0.62 g, 23 mmol) and cyclopropanesulfonyl chloride (2.4 g, 17 mmol) were added to the single-necked bottle. The mixture was stirred at room temperature for 24 h, then diluted with EA (50 mL) and water (50 mL). The organic phase was washed with saturated sodium chloride solution, dried over anhydrous sodium sulfate, and concentrated under reduced pressure. The residue was purified by silica gel column chromatography (PE/EA(V/V)=1/1) to give the title compound as a white solid (1.0 g 3.4 mmol, 22%). MS (ESI, pos.ion) m/z: 299.5 [M+H]$^+$.

Step 2: ethyl 9-(1-(cyclopropylsulfonyl)-1H-pyrazol-4-yl)-6-isopropyl-10-methoxy-2-oxo-6,7-dihydro-2H-pyrido[2,1-a]phthalazine-3-formate

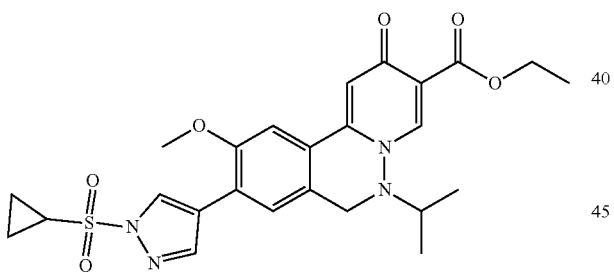

Ethyl 6-isopropyl-10-methoxy-2-oxo-9-(((trifluoromethyl)sulfonyl)oxy)-6,7-dihydro-2H-pyrido[2,1-a]phthalazine-3-formate (150 mg, 0.30 mmol), 1-cyclopropylsulfonyl-4-(4,4,5,5-tetramethyl-1,3,2-dioxaborolan-2-yl)-1H-pyrazole (0.187 g, 0.627 mmol), sodium bicarbonate (0.083 g, 0.94 mmol), dppfPdCl$_2$(0.040 g, 0.047 mmol), DME (5 mL, 95 mass %) and water (1 mL) were added to two-necked flask. The mixture was degassed and refilled with nitrogen for three times and then stirred at 65° C. for 5 h. The reaction solution was concentrated in vacuo, and the residue was purified by silica gel column chromatography (DCM/MeOH (V/V)=10/1) to give the title compound as brown oil (170 mg, 0.33 mmol, 99%).

MS (ESI, pos.ion) m/z: 513.2 [M+H]$^+$.

82

Step 3: 9-(1-(cyclopropylsulfonyl)-1H-pyrazole-4-yl)-6-isopropyl-10-methoxy-2-oxo-6,7-dihydro-2H-pyrido[2,1-a]phthalazine-3-carboxylic acid

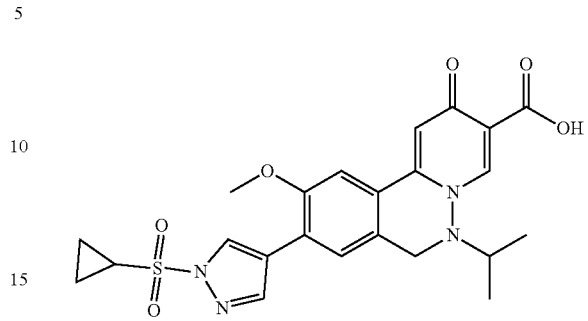

Ethyl 9-(1-(cyclopropylsulfonyl)-1H-pyrazole-4-yl)-6-isopropyl-10-methoxy-2-oxo-6,7-dihydro-2H-pyrido[2,1-a]phthalazine-3-formate (0.14 g, 0.27 mmol) was dissolved in DME (10 mL), DMF (1 mL) and water (0.5 mL, 30 mmol). 2,3,5,6-Tetrachloro-4-benzoquinone (0.20 g, 0.81 mmol) was added, and the reaction solution was stirred at refulx at 100° C. for 48 h. Post processing: The reaction mixture was concentrated. The residue was purified by slica column chromatography (DCM/MeOH(V/V)=15/1) to give the title compound as a grayish white solid (0.08 g, 0.2 mmol, 60%). MS (ESI, pos.ion) m/z: 485.4 [M+H]$^+$; $^1$H NMR (400 MHz, DMSO-d$_6$) δ 16.31 (s, 1H, 8.69 (s, 1H), 8.51 (d, J=5.2 Hz, 2H), 7.96 (s, 1H), 7.78 (s, 1H), 7.69 (s, 1H), 4.53 (s, 2H), 4.07 (s, 3H), 2.89 (dd, J=12.4, 6.2 Hz, 1H), 1.31 (d, J=3.6 Hz, 2H), 1.23 (d, J=4.1 Hz, 3H), 0.96 (s, 6H).

Example 25: 9-(1-(1-(cyclopropylmethoxy)-2-methylpropane-2-yl)-1H-pyrazole-4-yl)-6-isopropyl-10-methoxy-2-oxo-6,7-dihydro-2H-pyrido[2,1-a]phthalazine-3-carboxylic acid

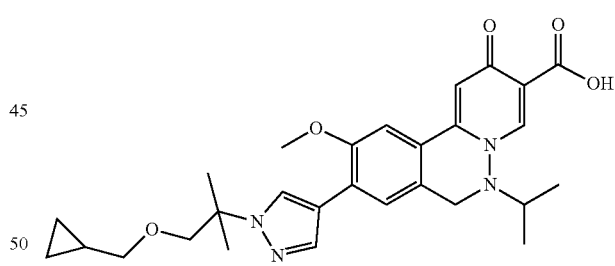

Step 1: Ethyl 2-(4-bromo-1H-pyrazol-1-yl)-2-methylpropanoate

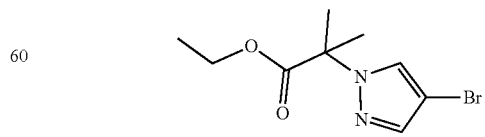

To a dry reaction bottle were added 4-bromopyrazole (5 g 34.02 mmol), barium carbonate (16.63 g 51.04 mmol), DMF (100 mL) and ethyl 2-bromo-2-methylpropionate (6 mL, 40.88 mmol). The reaction solution was warmed to 90° C. and stirred for 24 h. Post processing: Water (100 mL) was added to dissolve the solid. The solution was extracted with ethyl acetate (100 mL×2). The organic phases were combined and then washed with saturated sodium chloride solution three times and concentrated in vacuo. The residue was purified by silica gel column chromatography (PE/EA (V/V)=10/1) to give the product as colorless oil (7.5 g 27.41 mmol, 80%). MS (ESI, pos.ion) m/z: 261.0[M+H]⁺

Step 2: 2-(4-bromo-1H-pyrazol-1-yl)-2-methyl-1-propanol

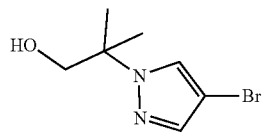

Ethyl 2-(4-bromo-1H-pyrazol-1-yl)-2-methylpropanoate (7.15 g, 27.4 mmol) was dissolved in tetrahydrofuran (70 mL), sodium borohydride (6.47 g, 164 mmol) was added under ice bath, and the mixture was warmed to 60° C. and stirred for 12 h. Post processing: the mixture ws concentrated in vacuo. The residue was added with water (80 mL) and ethyl acetate (80 mL). After separation, the aqueous phase was extracted with ethyl acetate (60 mL×2), and the organic phases were combined and washed with saturated sodium chloride solution (80 mL), then concentrated in vacuo. The residue was purified by silica gel column chromatography (PE/EA(V/V)=5/1) to give the title compound as a white solid (4.65 g 21.2 mmol, 77.5%). MS (ESI, pos.ion) m/z: 219.1/221.1 [M+H]⁺.

Step 3: 4-bromo-1-(1-(cyclopropylmethoxy)-2-methylpropan-2-yl)-1H-pyrazole

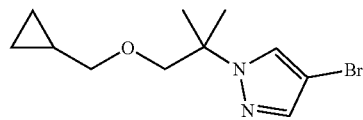

To a dry reaction bottle were added sodium hydride (730 mg, 18.25 mmol, 60% mass) and N,N-dimethylformamide (10 mL). The reaction system was cooled to 0° C., and 2-(4-bromo-1H-pyrazol-1-yl)-2-methyl-1-propanol (1 g, 4.56 mmol) was added. Then the reaction solution was warmed to room temperature and stirred for 20 min, bromomethylcyclopropane (0.9 mL, 9 mmol) was added. The resulting mixture was continuously stirred at room temperature for 18 h. Post processing: The reaction was quenched with water (10 mL), and diluted with ethyl acetate (20 mL). The reaction mixture was separated. The upper organic phase was collected. The aqueous phase was extracted with ethyl acetate (20 mL×3). The organic phases were combined. The combined organic phase were washed with saturated sodium chloride solution and concentrated in vacuo. The residue was purified by silica gel column chromatography (PE/EA(V/V)=15/1) to give the title compound as colorless oil (1.085 g, 3.97 mmol, 87%). MS (ESI, pos.ion) m/z: 273.2, 275.2[M+H]⁺

Step 4: 1-(1-(cyclopropylmethoxy)-2-methylpropan-2-yl)-4-(4,4,5,5-tetramethyl-1,3,2-dioxaborolan-2-yl)-1H-pyrazole

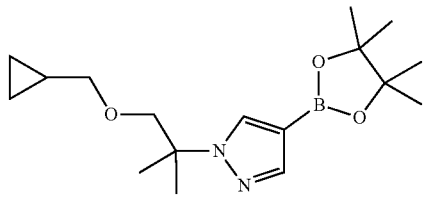 [SMILES: CC(C)(COCC1CC1)n1cc(B2OC(C)(C)C(C)(C)O2)cn1]

To a reaction flask were added 4-bromo-1-(1-(cyclopropylmethoxy)-2-methylpropan-2-yl)-1H-pyrazole (520 mg, 1.90 mmol), bis(pinacolato)diboron (725 mg, 2.86 mmol), potassium acetate (467 mg, 4.76 mmol), 1,1'-bis(diphenylphosphino)ferrocene palladium(II) chloride complex (155 mg, 0.19 mmol) and 1,4-dioxane (10 mL). The reaction mixture was degassed and refilled with nitrogen for three times, then warmed to 80° C. and stirred for 6 h. Post processing: The reaction mixture was concentrated in vacuo. The residue was purified by silica gel column chromatography (PE/EA(V/V)=15/1) to give the title compound as colorless oil (170 mg, 0.18 mmol, 24%). MS (ESI, pos.ion) m/z: 321.2[M+H]⁺

Step 5: 9-(1-(1-(cyclopropylmethoxy)-2-methylpropane-2-yl)-1H-pyrazole-4-yl)-6-isopropyl-10-methoxy-2-oxo-6,7-dihydro-2H-pyrido[2,1-a]phthalazine-3-carboxylic acid

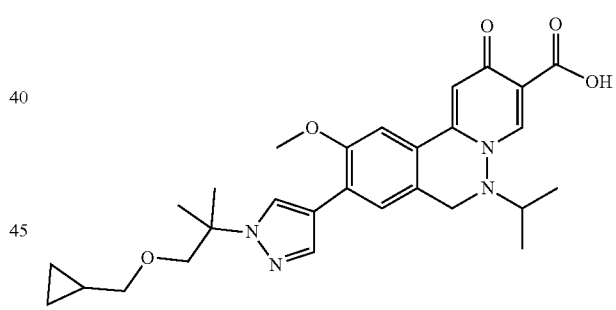

Methyl 6-isopropyl-10-methoxy-2-oxo-9-(((trifluoromethyl)sulfonyl)oxy)-6,7-dihydro-2H-pyrido[2,1-a]pyridazine-3-formate and 1-(1-(cyclopropylmethoxy)-2-methylpropan-2-yl)-4-(4,4,5,5-tetramethyl-1,3,2-dioxaborolan-2-yl)-1H-pyrazole were taken as raw materials according to the synthetic method in step 13 of example 1 to give the title compound as a grayish white solid. MS (ESI, pos.ion) m/z: 507.2[M+H]⁺; ¹H NMR (400 MHz, DMSO-d₆) δ 8.48 (s, 1H), 8.28 (s, 1H), 8.03 (s, 1H), 7.81 (s, 1H), 7.70 (s, 1H), 7.63 (s, 1H), 4.52 (s, 2H), 4.03 (s, 3H), 3.65 (s, 2H), 3.16 (d, J=6.7 Hz, 2H), 2.99-2.83 (m, 1H), 1.55 (s, 6H), 1.23 (s, 1H), 0.95 (d, J=5.6 Hz, 6H), 0.49-0.35 (m, 2H), 0.22-0.06 (m, 2H).

Biological Activity Test

HBV Cell Line

The chromosome of HepG2.2.15 cells integrates a complete HBV genome and stably expresses viral RNA and protein. HepG2.2.15 cells can secrete mature hepatitis B virus particles and HBsAg into culture medium. Virus particles DNA and HBsAg secreted by HepG 2.2.15 cells can be quantified by q-PCR and ELISA, and the effects of compounds on viral replication and HBsAg secretion can be detected.

Test 1: Inhibition Experiment of the Compound of the Invention on HBV Virus Replication Test Method HepG 2.2.15 cells were inoculated with 8,000 per cell to 96-well cell culture plates in duplicate, and were cultured for 3 days until the cells grew to full-hole. Cells were treated with 4-fold serial dilutions of compounds for 10 days, and were given alternately every other day. The final concentration of DMSO in all pores was 0.5% and DMSO was used as a drug-free control. The supernatant was collected for quantitative detection of HBV DNA on day 11.

Viral genomic DNA was detected by qPCR method, and HBV primers were as follows:
HBV-For-202, CAGGCGGGGTTTTTCTTGTTGA (SEQ ID NO:1);
HBV-Rev-315, GTGATTGGAGGTTGGGGACTGC (SEQ ID NO:2).

The SYBR Premix Ex Taq II-Takara DRR081S kit was used, and 1 µL of cell culture supernatant was used as a template. A standard curve was made using a plasmid containing the HBV genome, and the viral copy number was calculated using the standard curve. Concentration-virus copy number was processed using Graphpad Prism 5 software, and $IC_{50}$ of Compounds Inhibiting Virus Replication was calculated by Four-parameter Nonlinear Regression Model.

Conclusion: The inhibiting experiment of the compound of the invention against HBV virus replication shows that the compound of the invention has good inhibiting activity against HBV DNA replication, wherein the $IC_{50}$ of inhibitory activity against HBV DNA replication of the compound provided herein is less than 0.1 µM, and the $IC_{50}$ of inhibitory activity against HBV DNA replication of the most compound is less than 0.05 µM.

The inhibitory activity of some compounds in this application against HBV DNA replication is shown in Table 2.

TABLE 2 inhibitory activity of some compounds against HBV DNA replication

| Example | DNA $IC_{50}$ (nM) |
| --- | --- |
| Example 1 | 2.68 |
| Example 2 | 2.06 |
| Example 3 | 1.71 |
| Example 4 | 3.81 |
| Example 5 | 7.3 |
| Example 7 | 1.76 |
| Example 8 | 6.26 |
| Example 13 | 0.7 |
| Example 14 | <0.24 |
| Example 15 | 2.10 |
| Example 16 | 2.74 |
| Example 17 | 2.82 |
| Example 18 | 2.28 |
| Example 19 | 3.98 |

Test Method

HepG 2.2.15 cells were inoculated with 8,000 per cell to 96-well cell culture plates in duplicate, and were cultured for 3 days until the cells grew to full-hole. Cells were treated with 4-fold serial dilutions of compounds for 10 days, and were given alternately every other day. The final concentration of DMSO in all pores was 0.5% and DMSO was used as a drug-free control. The supernatant was collected for quantitative detection of HBsAg on day 11.

The level of HBsAg secreted by the compound after treatment is detected by ELISA method, and the method uses a hepatitis B surface antigen diagnostic kit (Shanghai Kehua Biotech Co., Ltd. S10910113). 25 µL of the supernatant to be assayed (PBS was diluted to 75 µL) was added to per well of the ELISA plate, positive control and negative control kit were set. ELISA plate was blocked with a cover paper, and incubated at 37° C. for 60 minutes. The ELISAplate was taken out, the seal was teared off, and 50 µL of enzyme conjugate was added to each well. The ELISA plate was oscillated on the shaker for 10 seconds, blocked with a cover paper and incubated at 37° C. for 30 minutes. The ELISA plate was taken out, the seal was teared off, and the ELISA plate was washed 5 times: each time the liquid in the hole was discarded, the washing liquid was filled into the holes, left to stand for 60 seconds, dried, and the liquid residue was patted on the absorbent paper. Immediately after the end of washing, a freshly prepared mixture of Developer A and Developer B was added to all wells: 100 µL per well. The ELISA plate was oscillated on the shaker for 10 seconds, blocked with a cover paper and incubated at 37° C. for 30 minutes. 50 µL of stop solution was added to all wells. Absorbance was read on the Envision plate reader at 450 nm. Concentration-HBsAg OD450 was processed using Graphpad Prism 5 software, and $IC_{50}$ of Compounds Inhibiting Virus Replication was calculated by Four-parameter Nonlinear Regression Model.

Conclusion: The inhibiting experiment of the compound of the invention against HBsAg secretion shows that the compound of the invention has good inhibiting activity against HBsAg secretion, wherein the $IC_{50}$ of inhibitory activity against HBsAg secretion of the compound provided herein is less than 0.1 µM, and the $IC_{50}$ of inhibitory activity against HBsAg secretion of the most compound is less than 0.05 µM.

The inhibitory activity of some compounds in this application against HBsAg secretion is shown in Table 3.

TABLE 3 inhibitory activity of some compounds against HBsAg secretion

| Example | Hbs Ag $IC_{50}$ (nM) |
| --- | --- |
| Example 1 | 4.27 |
| Example 2 | 1.72 |
| Example 3 | 3.26 |
| Example 4 | 9.60 |
| Example 5 | 14.35 |
| Example 7 | 6.73 |
| Example 8 | 6.03 |
| Example 13 | 0.97 |
| Example 14 | <0.24 |
| Example 15 | 1.83 |
| Example 16 | 6.11 |
| Example 17 | 4.07 |
| Example 18 | 3.73 |
| Example 19 | 7.82 |

Test 3: Pharmacokinetic Experiments of the Compounds of the Invention in Beagle Dogs, Mice and Rats (1) Pharmacokinetic Experiments in Beagle Dogs Pharmacokinetic experiments of the compounds of the invention in beagle dogs (Body weight 10-12 kg, male, age 10-12 months, 3 per oral group, 3 per intravenous injection group) Test method:

Beagle was administered orally with 2.5 mg/kg or 5 mg/kg of the compound tested or intravenously injected with 1 mg/kg or 2 mg/kg of the compound tested.

After administration, venous blood was collected at time points (0.083, 0.25, 0.5, 1, 2, 4, 6, 8 and 24 hours) and collected in an anticoagulation tube with EDTA-K$_2$. After liquid-liquid extraction, plasma samples were quantitatively analyzed by multiple reaction ion monitoring (MRM) on a triple quadrupole tandem mass spectrometer. Pharmacokinetic parameters were calculated using a noncompartmental method by WinNonLin 6.3 software.

The pharmacokinetic properties of some compounds disclosed herein were shown in Table 4.

TABLE 4

The pharmacokinetic properties of some compounds

| Test compound | Drug delivery route | dose (mg/kg) | Cmax(ng/mL) | AUC$_{(0-t)}$ (h·ng/mL) | AUC$_{INF}$ (h·ng/mL) | CL(mL/min/kg) | F(%) |
|---|---|---|---|---|---|---|---|
| Example 5 | IV | 1 | 2170 | 16900 | 17400 | 0.955 | N/A |
|  | PO | 5 | 8710 | 63300 | 66700 | N/A | 76.7 |

Conclusion: The compounds disclosed herein exhibited optimized pharmacokinetic properties with good absorption and desirable oral bioavailability (F) when the compounds were administered orally or intravenously.

(2) Pharmacokinetic Experiments in ICR Mice

Pharmacokinetic experiments of the compounds of the invention in beagle dogs (Body weight 20-25 g, male, age 45-60 days, 3 per oral group, 3 per intravenous injection group)

Test Method

ICR mice was administered orally with 10 mg/kg of the tested compound or intravenously injected with 2 mg/kg or 10 mg/kg of the tested compound. After administration, venous blood was collected at time points (0.083, 0.25, 0.5, 1, 2, 4, 6, 8 and 24 hours) and collected in an anticoagulation tube with EDTA-K$_2$. After liquid-liquid extraction, plasma samples were quantitatively analyzed by multiple reaction ion monitoring (MRM) on a triple quadrupole tandem mass spectrometer. Pharmacokinetic parameters were calculated using a noncompartmental method by WinNonLin 6.1 software.

Conclusion: pharmacokinetic data show that the compound has good pharmacokinetic properties in ICR mice, and has good application prospects in anti-HBV (3) Pharmacokinetic Experiments in SD Rat Pharmacokinetic experiments of the compounds of the invention in SD rats (Body weight 200-250 g, male, age 2-3 months, 3 per oral group, 3 per intravenous injection group)

Test Method

SD rats were administered orally with 2.5 mg/kg or 5 mg/kg of the tested compound or intravenously injected with 1 mg/kg of the tested compound. After administration, venous blood was collected at time points (0.083, 0.25, 0.5, 1, 2, 5, 7 and 24 hours) and collected in an anticoagulation tube with EDTA-K$_2$. After liquid-liquid extraction, plasma samples were quantitatively analyzed by multiple reaction ion monitoring (MRM) on a triple quadrupole tandem mass spectrometer. Pharmacokinetic parameters were calculated using a noncompartmental method by WinNonLin 6.3 software.

Conclusion: Pharmacokinetic data show that the compound has good pharmacokinetic properties in SD rats, and has good application prospects in anti-HBV

Test 4: Stability Test of Compounds of the Invention in Liver Microsomes of Different Species Test Method 30 μL of a mixed solution of blank solution and liver microsomes were added to a 96-well plate, 15 μL of buffer containing the test compound was added to each well, and two samples in parallel were made. After incubation for 10 minutes at 37° C., 15 μL NADPH solution (8 mM) was added at time points of 0 min, 15 min, 20 min and 60 min, the final concentration of the compounds to be measured was 1 μM, the concentration of liver microsomes was 0.1 mg/mL, and the final concentration of NADPH was 2 mM. After incubation for 0, 15, 30 and 60 minutes, 150 Lμ acetonitrile (including internal standard) was added into the mixed system. The sample diluted with acetonitrile was centrifuged at 4000 rpm for 5 min. 150 μL supernatant was taken for LC-MS/MS for analysis.

Conclusion: the experimental data of liver microsome stability show that the compounds of the invention have good stability in liver microsomes of different genera.

The invention claimed is:

1. A compound having Formula (I) or a stereoisomer, a tautomer, an N-oxide, a solvate, or a pharmaceutically acceptable salt thereof, wherein:

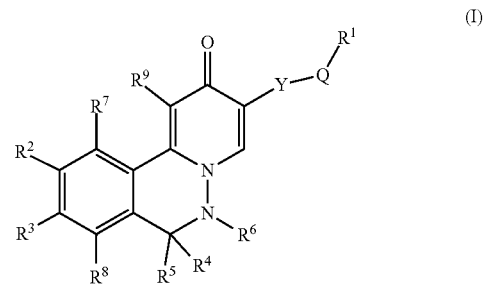

Y is a single bond, —CH$_2$— or —C(=O)—;
Q is a single bond, —O— or —N(R$^{10}$)—;
R$^1$ is hydrogen, deuterium, fluorine, chlorine, bromine, iodine, OH, —COOH, heterocyclyl consisting of 5-6 ring atoms, heteroaryl consisting of 5-6 ring atoms, C$_{1-6}$ alkyl, C$_{2-6}$ alkenyl, C$_{2-6}$ alkynyl, C$_{3-7}$ cycloalkyl or R$^a$R$^b$N—, wherein each of the heterocyclyl consisting of 5-6 ring atoms, heteroaryl consisting of 5-6 ring atoms, C$_{1-6}$ alkyl, C$_{2-6}$ alkenyl, C$_{2-6}$ alkynyl and C$_{3-7}$ cycloalkyl is independently unsubstituted or substituted by 1, 2, 3 or 4 R$^v$;
R$^{10}$ is hydrogen, deuterium, C$_{1-6}$ alkyl or C$_{1-6}$ haloalkyl, or R$^{10}$, R$^1$ together with the nitrogen atom to which they are attached form a heterocyclyl consisting of 3 to 6 ring atoms, wherein each of the C$_{1-6}$ alkyl, C$_{1-6}$ haloalkyl and heterocyclyl consisting of 3-6 ring atoms is independently unsubstituted or substituted by 1, 2, 3 or 4 substituents selected from —COOH, =O, tetrazolyl or $C_{1-6}$ alkyl-OC(=O)—;

$R^2$ is hydrogen, deuterium, halogen, cyano, $C_{1-6}$ alkyl or $C_{1-6}$ alkoxy, wherein each of the $C_{1-6}$ alkyl and $C_{1-6}$ alkoxy is independently unsubstitued or substituted by 1, 2, 3, or 4 $R^w$;

$R^3$ is halogen, $C_{1-6}$ alkyl, $C_{2-6}$ alkenyl, $C_{2-6}$ alkynyl, $C_{3-7}$ cycloalkyl, heterocyclyl consisting of 3-12 ring atoms, $C_{6-10}$ aryl and heteroaryl consisting of 5-10 atoms; wherein each of the $C_{1-6}$ alkyl, $C_{2-6}$ alkenyl, $C_{2-6}$ alkynyl, $C_{3-7}$ cycloalkyl, heterocyclyl consisting of 3-12 ring atoms, $C_{6-10}$ aryl and heteroaryl consisting of 5-10 ring atoms is independently unsubstituted or substituted by 1, 2, 3, or 4 $R^x$;

each of $R^4$ and $R^5$ is hydrogen, deuterium, $C_{1-6}$ alkyl, $C_{1-6}$ alkylamino, $C_{1-6}$ alkoxy, $C_{2-6}$ alkynyl, $C_{2-6}$ alkenyl, $C_{3-7}$ cycloalkyl and heterocyclyl consisting of 3-12 ring atoms; wherein each of the $C_{1-6}$ alkyl, $C_{1-6}$ alkylamino, $C_{1-6}$ alkoxy, $C_{2-6}$ alkynyl, $C_{2-6}$ alkenyl, $C_{3-7}$ cycloalkyl and heterocyclyl consisting of 3-12 ring atoms is independently unsubstituted or substituted by 1, 2, 3, or 4 $R^y$;

or $R^4$, $R^5$ together with the carbon atom to which they are attached form $C_{3-7}$ cycloalkyl or heterocyclyl consisting of 3 to 10 ring atoms;

$R^6$ is hydrogen, deuterium, $C_{1-6}$ alkyl, $C_{2-6}$ alkenyl, $C_{3-7}$ cycloalkyl, heterocyclyl consisting of 3-12 ring atoms, $C_{6-10}$ aryl and heteroaryl consisting of 5-10 ring atoms; wherein each of the $C_{1-6}$ alkyl, $C_{2-6}$ alkenyl, $C_{3-7}$ cycloalkyl, heterocyclyl consisting of 3-12 ring atoms, $C_{6-10}$ aryl and heteroaryl consisting of 5-10 atoms is independently unsubstituted or substituted by 1, 2, 3, or 4 $R^z$;

each $R^7$, $R^8$, $R^9$ is independently hydrogen, deuterium, F, Cl, Br, OH, cyano, $C_{1-6}$ alkyl, $C_{1-6}$ alkoxy, $C_{3-7}$ cycloalkyl, heterocyclyl consisting of 3-6 ring atoms, $C_{6-10}$ aryl and heteroaryl consisting of 5-10 ring atoms; wherein each of the $C_{1-6}$ alkyl, $C_{1-6}$ alkoxy, $C_{3-7}$ cycloalkyl, heterocyclyl consisting of 3-6 ring atoms, $C_{6-10}$ aryl and heteroaryl consisting of 5-10 ring atoms is independently unsubstituted or substituted by 1, 2, 3, or 4 $R^j$;

each $R^a$ and $R^b$ is independently hydrogen, deuterium, $C_{1-6}$ alkyl, $C_{1-6}$ alkoxy, $C_{2-6}$ alkynyl, $C_{2-6}$ alkenyl, $C_{3-6}$ cycloalkyl, $C_{6-10}$ aryl, heterocyclyl consisting of 3-6 ring atoms, or heteroaryl consisting of 5-10 atoms; wherein each of the $C_{1-6}$ alkyl, $C_{1-6}$ alkoxy, $C_{2-6}$ alkynyl, $C_{2-6}$ alkenyl, $C_{3-6}$ cycloalkyl, $C_{6-10}$ aryl, heterocyclyl consisting of 3-6 ring atoms and heteroaryl consisting of 5-10 atoms is independently unsubstituted or substituted by 1, 2, 3, or 4 substituents selected from F, Cl, Br, CN, OH, amino, $C_{1-6}$ alkyl, $C_{1-6}$ haloalkyl, $C_{1-6}$ alkoxy or $C_{1-6}$ alkylamino;

each $R^v$, $R^w$, $R^y$, $R^z$ and $R^j$ is independently deuterium, F, Cl, Br, CN, =O, OH, —COOH, amino, $C_{1-6}$ alkyl, $C_{1-6}$ alkoxy, $C_{1-6}$ alkylthio, $C_{1-6}$ alkylamino, $C_{2-6}$ alkenyl, $C_{2-6}$ alkynyl, $C_{3-7}$ cycloalkyl, heterocyclyl consisting of 3-6 ring atoms, $C_{6-10}$ aryl and heteroaryl consisting of 5-10 atoms; wherein each of the amino, $C_{1-6}$ alkyl, $C_{1-6}$ alkoxy, $C_{1-6}$ alkylthio, $C_{1-6}$ alkylamino, $C_{2-6}$ alkenyl, $C_{2-6}$ alkynyl, $C_{3-7}$ cycloalkyl, heterocyclyl consisting of 3-6 ring atoms, $C_{6-10}$ aryl and heteroaryl consisting of 5-10 atoms is independently unsubstituted or substituted by 1, 2, 3, or 4 $R^e$;

each $R^x$ is independently deuterium, F, Cl, Br, CN, =O, OH, —COOH, amino, $C_{1-12}$ alkyl, $C_{1-12}$ alkoxy, $C_{1-12}$ alkylthio, $C_{1-12}$ alkylamino, $C_{2-6}$ alkenyl, $C_{2-6}$ alkynyl, $C_{3-7}$ cycloalkyl, heterocyclyl consisting of 3-12 ring atoms, $C_{6-10}$ aryl and heteroaryl consisting of 5-10 atoms or -L-$R^{11}$; wherein each of the amino, $C_{1-12}$ alkyl, $C_{1-12}$ alkoxy, $C_{1-12}$ alkylthio, $C_{1-12}$ alkylamino, $C_{2-6}$ alkenyl, $C_{2-6}$ alkynyl, $C_{3-7}$ cycloalkyl, heterocyclyl consisting of 3-12 ring atoms, $C_{6-10}$ aryl and heteroaryl consisting of 5-10 ring atoms is independently unsubstituted or substituted by 1, 2, 3, or 4 $R^f$;

L is $C_{1-4}$ alkylene, $C_{1-3}$ heteroalkylene, —O—, —(C=O)—, —S(=O)$_q$— or —N($R^{12}$)—; wherein each of the $C_{1-4}$ alkylene and $C_{1-3}$ heteroalkylene is independently unsubstituted or substituted by 1, 2, 3 or 4 $R^g$;

$R^{11}$ is $C_{1-6}$ alkyl, $C_{1-6}$ alkoxy, $C_{3-7}$ cycloalkyl, heterocyclyl consisting of 3-12 ring atoms, $C_{6-10}$ aryl or heteroaryl consisting of 5-10 atoms; wherein each of the $C_{1-6}$ alkyl, $C_{1-6}$ alkoxy, $C_{3-7}$ cycloalkyl, heterocyclyl consisting of 3-12 ring atoms, $C_{6-10}$ aryl and heteroaryl consisting of 5-10 atoms is independently unsubstituted or substituted by 1, 2, 3, or 4 $R^h$;

each $R^e$, $R^f$, $R^g$ and $R^h$ is independently F, Cl, Br, CN, OH, =O, —COOH, —C(=O)O $C_{1-6}$ alkyl, —S(=O)$_2$— $C_{1-6}$ alkyl, —S(=O)$_2$—$C_{3-7}$ cycloalkyl, amino, $C_{1-6}$ alkyl, $C_{1-6}$ haloalkyl, $C_{1-6}$ alkoxy, $C_{1-6}$ alkylthio, $C_{1-6}$ haloalkoxy, $C_{1-12}$ alkylamino, $C_{2-6}$ alkenyl, $C_{2-6}$ alkynyl, $C_{6-10}$ aryl, $C_{3-7}$ cycloalkyl, heteroaryl consisting of 5-6 ring atoms, heterocyclyl consisting of 3-6 ring atoms, $C_{1-6}$ alkoxy $C_{1-4}$ alkylene or $C_{1-4}$ alkylamino $C_{1-4}$ alkylene;

$R^{12}$ is hydrogen, deuterium, $C_{1-6}$ alkyl or $C_{1-6}$ haloalkyl;

q is 0, 1, or 2;

wherein each heterocyclyl is a saturated or partially saturated non-aromatic monocyclic, bicyclic or tricyclic ring system containing from 3 to 12 ring atoms, wherein at least one ring member is selected from nitrogen, sulfur and oxygen; and wherein each heteroaryl is a monocyclic or bicyclic ring, and independently comprises 1 to 4 heteroatoms independently selected from nitrogen, sulfur and oxygen.

2. The compound of claim 1, wherein the R is hydrogen, deuterium, fluorine, chlorine, bromine, iodine, OH, —COOH, heterocyclyl consisting of 5 ring atoms, heterocyclyl consisting of 6 ring atoms, heteroaryl consisting 5 ring atoms, heteroaryl consisting of 6 ring atoms, $C_{1-4}$ alkyl, $C_{2-4}$ alkenyl, $C_{2-4}$ alkynyl, $C_{3-6}$ cycloalkyl or $R^aR^bN$—, wherein each of the heterocyclyl consisting of 5 ring atoms, heterocyclyl consisting of 6 ring atoms, heteroaryl consisting 5 ring atoms, heteroaryl consisting of 6 ring atoms, $C_{1-4}$ alkyl, $C_{2-4}$ alkenyl, $C_{2-4}$ alkynyl and $C_{3-6}$ cycloalkyl is independently unsubstituted or substituted by 1, 2, 3 or 4 $R^v$;

$R^{10}$ is hydrogen, deuterium, $C_{1-4}$ alkyl or $C_{1-4}$ haloalkyl, or $R^{10}$, $R^1$ together with the nitrogen atom to which they are attached form a heterocyclyl consisting of 5 or 6 ring atoms, wherein each of the $C_{1-4}$ alkyl, $C_{1-4}$ haloalkyl and heterocyclyl consisting of 5 or 6 ring atoms is independently unsubstituted or substituted by 1, 2, 3 or 4 substituents selected from —COOH, =O, tetrazolyl or $C_{1-4}$ alkyl-OC(=O)—;

$R^2$ is hydrogen, hydrazine, halogen, cyano, methyl, ethyl, n-propyl, isopropyl, n-butyl, isobutyl, n-pentyl, n-hexyl, methoxy, ethoxy, 1-propoxy, 2-propoxy, 1-butoxy, 2-methyl-1-propoxy, 2-butoxy, 2-methyl-2-propoxy or 1-pentyloxy; wherein each of the methyl, ethyl, n-propyl, isopropyl, n-butyl, isobutyl, n-pentyl, n-hexyl, methoxy, ethoxy, 1-propoxy, 2-propoxy, 1-butoxy, 2-methyl-1-propoxy, 2-butoxy, 2-methyl-2- propoxy or 1-pentyloxy is independently unsubstituted or substituted by 1, 2, 3 or 4 $R^w$.

3. The compound of claim 1, wherein $R^1$ is hydrogen, deuterium, F, Cl, Br, I, OH, —COOH, thiazolyl, tetrazolyl, methyl, ethyl, n-propyl, isopropyl, vinyl, propenyl, allyl, ethynyl, propynyl, cyclopropyl, cyclobutyl, cyclopentyl, cyclohexyl or $R^aR^bN$—, wherein each of the thiazolyl, tetrazolyl, methyl, ethyl, n-propyl, isopropyl, vinyl, propenyl, allyl, ethynyl, propynyl, cyclopropyl, cyclobutyl, cyclopentyl, cyclohexyl is independently unsubstituted or substituted by 1, 2, 3 or 4 $R^v$;

$R^{10}$ is hydrogen, deuterium, methyl, ethyl, n-propyl, isopropyl or $C_{1-3}$ haloalkyl, or pyrrolidinyl, piperazinyl, piperidinyl or morpholinyl formed by $R^{10}$, $R^1$ together with the nitrogen atom to which they are attached, wherein each of the methyl, ethyl, n-propyl, isopropyl or $C_{1-3}$ haloalkyl, or pyrrolidinyl, piperazinyl, piperidinyl and morpholinyl is independently unsubstituted or substituted by 1, 2, 3 or 4 substituents selected from —COOH, =O, tetrazolyl or $C_{1-3}$ alkyl-OC(=O)—.

4. The compound of claim 1, wherein $R^3$ is halogen, $C_{1-4}$ alkyl, $C_{2-4}$ alkenyl, $C_{2-4}$ alkynyl, $C_{3-6}$ cycloalkyl, heterocyclyl consisting of 3-6 ring atoms, phenyl, naphthyl, heteroaryl consisting of 5 or 6 ring atoms; wherein each of the $C_{1-4}$ alkyl, $C_{2-4}$ alkenyl, $C_{2-4}$ alkynyl, $C_{3-6}$ cycloalkyl, heterocyclyl consisting of 3-6 ring atoms, phenyl, naphthyl, heteroaryl consisting of 5 or 6 ring atoms is independently unsubstituted or substituted by 1, 2, 3, or 4 $R^x$.

5. The compound of claim 1, wherein $R^3$ is halogen, methyl, ethyl, n-propyl, isopropyl, n-butyl, isobutyl, vinyl, propenyl, allyl, ethynyl, propynyl, propargyl, cyclopropyl, cyclobutyl, cyclopentyl, cyclohexyl, azetidinyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazine, pyridazinyl and pyrimidinyl, wherein each of the methyl, ethyl, n-propyl, isopropyl, n-butyl, isobutyl, vinyl, propenyl, allyl, ethynyl, propynyl, propargyl, cyclopropyl, cyclobutyl, cyclopentyl, cyclohexyl, azetidinyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazine or pyridazinyl.

6. The compound of claim 1, wherein each $R^4$ and $R^5$ is independently hydrogen, deuterium, $C_{1-4}$ alkyl, $C_{1-4}$ alkylamino, $C_{1-4}$ alkoxy, $C_{2-4}$ alkynyl, $C_{2-4}$ alkenyl, $C_{3-6}$ cycloalkyl or heterocyclyl consisting of 3-6 ring atoms; wherein each of the $C_{1-4}$ alkyl, $C_{1-4}$ alkylamino, $C_{1-4}$ alkoxy, $C_{2-4}$ alkynyl, $C_{2-4}$ alkenyl, $C_{3-6}$ cycloalkyl and heterocyclyl consisting of 3-6 ring atoms is independently unsubstituted or substituted by 1, 2, 3, or 4 $R^y$;

or $R^4$, $R^5$ together with the carbon atom to which they are attached form cyclopropyl, cyclobutyl, cyclopentyl, cyclohexyl or heterocyclyl consisting of 3-6 ring atoms;

$R^6$ is hydrogen, deuterium, $C_{1-4}$ alkyl, $C_{2-4}$ alkenyl, $C_{3-6}$ cycloalkyl, heterocyclyl consisting of 3-6 ring atoms, phenyl, naphthyl or heteroaryl consisting of 5 or 6 ring atoms; wherein each of the $C_{1-4}$ alkyl, $C_{2-4}$ alkenyl, $C_{3-6}$ cycloalkyl, heterocyclyl consisting of 3-6 ring atoms, phenyl, naphthyl and heteroaryl consisting of 5 or 6 ring atoms is independently unsubstituted or substituted by 1, 2,3 or 4 $R^z$;

each $R^7$, $R^8$, and $R^9$ is independently hydrogen, deuterium, F, Cl, Br, OH, cyano, $C_{1-4}$ alkyl, $C_{1-4}$ alkoxy, $C_{3-6}$ cycloalkyl, heteroclyl consisting of 3-6 ring atoms, phenyl, naphthyl or heteroaryl consisting of 5 or 6 ring atoms; wherein each of the $C_{1-4}$ alkyl, $C_{1-4}$ alkoxy, $C_{3-6}$ cycloalkyl, heteroclyl consisting of 3-6 ring atoms, phenyl, naphthyl and heteroaryl consisting of 5 or 6 ring atoms is independently unsubstituted or substituted by 1, 2,3 or 4 $R^j$;

each $R^a$ and $R^b$ is independently hydrogen, deuterium, $C_{1-4}$ alkyl, $C_{1-4}$ alkoxy, $C_{2-4}$ alkenyl, $C_{2-4}$ alkynyl, $C_{3-6}$ cycloalkyl, phenyl, naphthyl, heteroclyl consisting of 3-6 ring atoms or heteroaryl consisting of 5 or 6 ring atoms; wherein each of the $C_{1-4}$ alkyl, $C_{1-4}$ alkoxy, $C_{2-4}$ alkenyl, $C_{2-4}$ alkynyl, $C_{3-6}$ cycloalkyl, phenyl, naphthyl, heteroclyl consisting of 3-6 ring atoms and heteroaryl consisting of 5 or 6 ring atoms is independently unsubstituted or substituted by 1, 2,3 or 4 substituents selected from F, Cl, Br, CN, OH, amino, $C_{1-4}$ alkyl, $C_{1-4}$ haloalkyl, $C_{1-4}$ alkoxy or $C_{1-4}$ alkylamino.

7. The compound of claim 1, wherein each $R^4$ and $R^5$ is independently hydrogen, deuterium, methyl, ethyl, n-propyl, isopropyl, n-butyl, isobutyl, N-methylamino, N-ethylamino, N,N-dimethylamino, N,N-diethylamino, N-propylamino, methoxy, ethoxy, 1-propoxy, 2-propoxy, 1-butoxy, 2-methyl-1-propoxy, 2-butoxy, 2-methyl-2-propoxy, vinyl, propenyl, allyl, ethynyl, propynyl, propargyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl or piperazinyl; wherein each of the methyl, ethyl, n-propyl, isopropyl, n-butyl, isobutyl, N-methylamino, N-ethylamino, N,N-dimethylamino, N,N-diethylamino, N-propylamino, methoxy, ethoxy, 1-propoxy, 2-propoxy, 1-butoxy, 2-methyl-1-propoxy, 2-butoxy, 2-methyl-2-propoxy, vinyl, propenyl, allyl, ethynyl, propynyl, propargyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, piperidinyl, morpholinyl, thiomorpholinyl and piperazinyl is independently unsubstituted or substituted by 1, 2,3 or 4 $R^y$;

or $R^4$, $R^5$ together with the carbon atom to which they are attached form a cyclopropyl, cyclobutyl, cyclopentyl, cyclohexyl, azetidinyl, oxetanyl, oxacyclopropyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl or piperazinyl;

$R^6$ is hydrogen, deuterium, methyl, ethyl, n-propyl, isopropyl, n-butyl, isobutyl, tert-butyl, vinyl, propenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of the methyl, ethyl, n-propyl, isopropyl, n-butyl, isobutyl, tert-butyl, vinyl, propenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3 or 4 $R^z$;

each $R^7$, $R^8$ and $R^9$ is independently hydrogen, deuterium, F, Cl, Br, OH, cyano, methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of the methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3 or 4 $R^j$;

each $R^a$ and $R^b$ is independently hydrogen, deuterium, methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, vinyl, propenyl, ethynyl, propynyl, propargyl, cyclopropyl, cyclobutyl, cyclopentyl, cyclohexyl, phenyl, naphthyl, pyrrolidinyl pyrazinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of the methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, vinyl, propenyl, ethynyl, propynyl, propargyl, cyclopropyl, cyclobutyl, cyclopentyl, cyclohexyl, phenyl, naphthyl, pyrrolidinyl pyrazinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3 or 4 substituents selected from F, Cl, Br, CN, OH, amino, $C_{1-3}$ alkyl, $C_{1-3}$ haloalkyl, $C_{1-3}$ alkoxy or $C_{1-3}$ alkylamino.

8. The compound of claim 1, each of $R^v$, $R^w$, $R^y$, $R^z$ and $R^j$ is independently deuterium, fluorine, chlorine, bromine, CN, =O, OH, —COOH, amino, $C_{1-4}$ alkyl, $C_{1-4}$ alkoxy, $C_{1-4}$ alkylthio, $C_{1-4}$ alkylamino, $C_{2-4}$ alkenyl, $C_{2-4}$ alkynyl, $C_{3-6}$ cycloalkyl, heterocyclyl consisting of 3 to 6 ring atoms, phenyl, naphthyl or heteroaryl consisting of 5 or 6 ring atoms, wherein each of the amino, $C_{1-4}$ alkyl, $C_{1-4}$ alkoxy, $C_{1-4}$ alkylthio, $C_{1-4}$ alkylamino, $C_{2-4}$ alkenyl, $C_{2-4}$ alkynyl, $C_{3-6}$ cycloalkyl, heterocyclyl consisting of 3 to 6 ring atoms, phenyl, naphthyl and heteroaryl consisting of 5 or 6 ring atoms is independently unsubstituted or substituted by 1, 2, 3 or 4 $R^e$.

9. The compound of claim 1, each of $R^v$, $R^w$, $R^y$, $R^z$, and $R^j$ is independently deuterium, F, Cl, Br, CN, =O, OH, —COOH, amino, methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, $C_{1-3}$ alkylthio, N-methylamino, N-ethylamino, N,N-dimethylamino, N,N-diethylamino, N-propylamino, vinyl, propenyl, ethynyl, propynyl, propargyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of the amino, methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, $C_{1-3}$ alkylthio, N-methylamino, N-ethylamino, N,N-dimethylamino, N,N-diethylamino, N-propylamino, vinyl, propenyl, ethynyl, propynyl, propargyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3 or 4 $R^e$.

10. The compound of claim 1, each $R^x$ is independently deuterium, F, Cl, Br, CN, =O, OH, —COOH, amino, $C_{1-6}$ alkyl, $C_{1-6}$ alkoxy, $C_{1-6}$ alkylthio, $C_{1-6}$ alkylamino, $C_{2-4}$ alkenyl, $C_{2-4}$ alkynyl, $C_{3-6}$ cycloalkyl, heterocyclyl consisting of 3 to 6 ring atoms, phenyl, naphthyl, heteroaryl consisting of 5 to 6 atoms or -L-$R^{11}$, wherein each of the amino, $C_{1-6}$ alkyl, $C_{1-6}$ alkoxy, $C_{1-6}$ alkylthio, $C_{1-6}$ alkylamino, $C_{2-4}$ alkenyl, $C_{2-4}$ alkynyl, $C_{3-6}$ cycloalkyl, heterocyclyl consisting of 3 to 6 ring atoms, phenyl, naphthyl and heteroaryl consisting of 5 to 6 atoms is independently unsubstituted or substituted by 1, 2, 3 or 4 $R^f$.

11. The compound of claim 1, each $R^x$ is deuterium, F, Cl, Br, CN, =O, OH, —COOH, amino, methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, $C_{1-3}$ alkylthio, N-methylamino, N-ethylamino, N,N-dimethylamino, N,N-diethylamino, N-propylamino, vinyl, propenyl, ethynyl, propynyl, 1-propynyl, cyclopropyl, cyclobutyl, cyclopentyl, cyclohexyl, azacyclobutyl, oxetanyl, oxacyclopropyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of the amino, methyl, ethyl, n-propyl, isopropyl, n-butyl, isobutyl, methoxy, ethoxy, 1-propoxy, 2-propoxy, 1-butoxy, 2-methyl-1-propoxy, 2-butoxy, $C_{1-3}$ alkylthio, N-methylamino, N-ethylamino, N,N-dimethylamino, N,N-diethylamino, N-propylamino, vinyl, propenyl, ethynyl, propynyl, 1-propynyl, cyclopropyl, cyclobutyl, cyclopentyl, cyclohexyl, azacyclobutyl, oxetanyl, oxacyclopropyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3 or 4 $R^f$.

12. The compound of claim 1, $R^{11}$ is $C_{1-4}$ alkyl, $C_{1-4}$ alkoxy, $C_{3-6}$ cycloalkyl, heterocyclyl consisting of 3 to 6 ring atoms, phenyl, naphthyl or heteroaryl consisting of 5 to 6 ring atoms, wherein each of the $C_{1-4}$ alkyl, $C_{1-4}$ alkoxy, $C_{3-6}$ cycloalkyl, heterocyclyl consisting of 3 to 6 ring atoms, phenyl, naphthyl and heteroaryl consisting of 5 to 6 ring atoms is independently unsubstituted or substituted by 1, 2, 3 or 4 $R^h$; or $R^{11}$ is methyl, ethyl, n-propyl, isopropyl, methoxy, ethoxy, 1-propoxy, 2-propoxy, 1-butoxy, 2-methyl-1-propoxy, 2-butoxy, cyclopropyl, cyclobutyl, cyclopentyl, cyclohexyl, azetidinyl, oxetanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of the methyl, ethyl, n-propyl, isopropyl, methoxy, ethoxy, 1-propoxy, 2-propoxy, 1-butoxy, 2-methyl-1-propoxy, 2-butoxy, cyclopropyl, cyclobutyl, cyclopentyl, cyclohexyl, azetidinyl, oxetanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, naphthyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3 or 4 $R^h$.

13. The compound of claim 1, wherein each of the $R^e$, $R^f$, $R^g$, and $R^h$ is independently F, Cl, Br, CN, OH, =O, —COOH, —C(=O)O$C_{1-4}$ alkyl, —S(=O)$_2$-$C_{1-4}$ alkyl, —S(=O)$_2$-cyclopropyl, —S(=O)$_2$-cyclobutyl, —S(=O)$_2$-cyclopentyl, —S(=O)$_2$-cyclohexyl, amino, $C_{1-4}$ alkyl, $C_{1-4}$ haloalkyl, $C_{1-4}$ alkoxy, $C_{1-4}$ alkylthio, $C_{1-4}$ haloalkoxy, $C_{1-6}$ alkylamino, $C_{2-4}$ alkenyl, $C_{2-4}$ alkynyl, phenyl, naphthyl, $C_{3-6}$ cycloalkyl, heteroaryl consisting of 5 or 6 ring atoms, heterocyclyl consisting of 5 or 6 ring atoms, $C_{1-4}$ alkoxy $C_{1-3}$ alkylene or $C_{1-4}$ alkylamino $C_{1-3}$ alkylene;

$R^{12}$ is hydrogen, deuterium, $C_{1-4}$ alkyl or $C_{1-4}$ haloalkyl.

14. The compound of claim 1, wherein each of the $R^e$, $R^f$, $R^g$, and $R^h$ is independently F, Cl, Br, CN, OH, =O, —COOH, —C(=O)O-methyl, —C(=O)O-ethyl, —C(=O)O-n-propyl, —C(=O)O-isopropyl, —C(=O)O-n-butyl, —C(=O)O-isobutyl, —C(=O)O-sec-butyl, —C(=O)O-tert-butyl, —S(=O)$_2$-methyl, —S(=O)$_2$-ethyl, —S(=O)$_2$-n-propyl, —S(=O)$_2$-isopropyl, —S(=O)$_2$-n-butyl, —S(=O)$_2$-isobutyl, —S(=O)$_2$-sec-butyl, —S(=O)$_2$-tert-butyl, —S(=O)$_2$-cyclopropyl, —S(=O)$_2$-cyclobutyl, —S(=O)$_2$-cyclopentyl, —S(=O)$_2$-cyclohexyl, amino, methyl, ethyl, n-propyl, isopropyl, n-butyl, isobutyl, $C_{1-3}$ haloalkyl, methoxy, ethoxy, 1-propoxy, 2-propoxy, 1-butoxy, 2-methyl-1-propoxy, 2-butoxy, $C_{1-3}$ alkylthio, $C_{1-3}$ haloalkoxy, N-methylamino, N-ethylamino, N,N-dimethylamino, N,N-diethylamino, N-propylamino, vinyl, propenyl, ethynyl, propynyl, propargyl, phenyl, naphthyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, $C_{1-3}$ alkoxy $C_{1-2}$ alkylene or $C_{1-3}$ alkylamino $C_{1-2}$ alkylene;

$R^{12}$ is hydrogen, deuterium, $C_{1-3}$ alkyl or $C_{1-3}$ haloalkyl.

15. A compound selected from the group consisting of the following compounds:

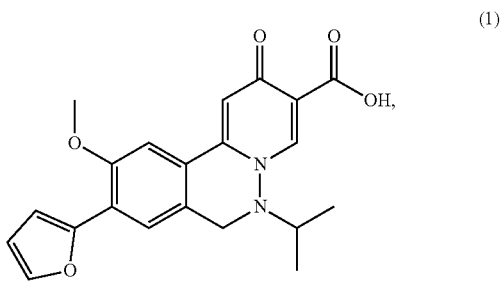

(1)

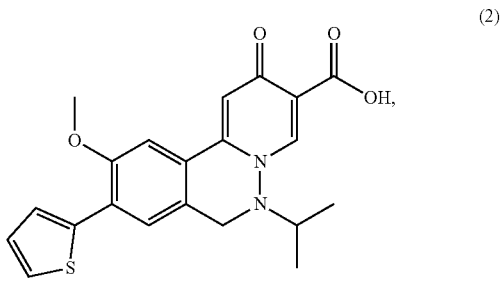

(2)

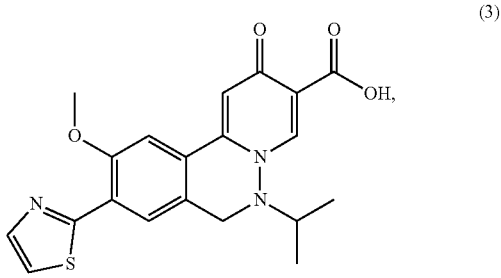

(3)

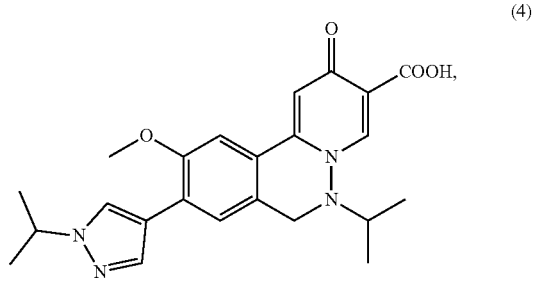

(4)

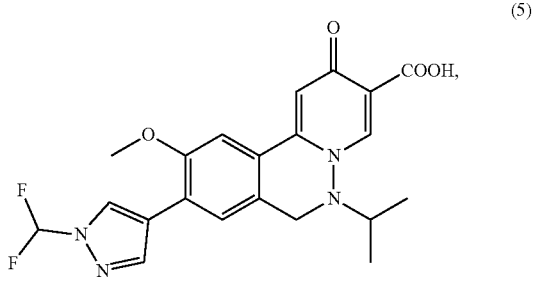

(5)

-continued
(6)
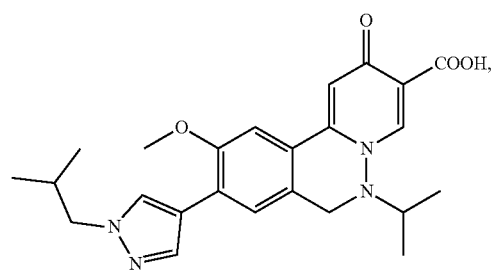
(7)
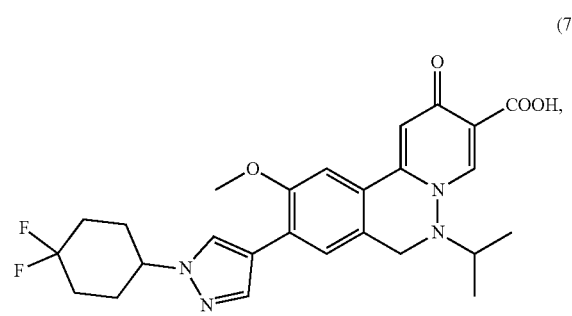
(8)
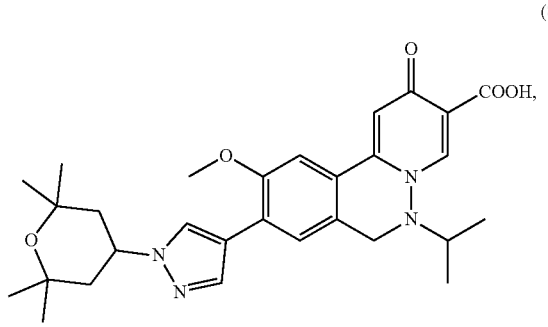
(9)
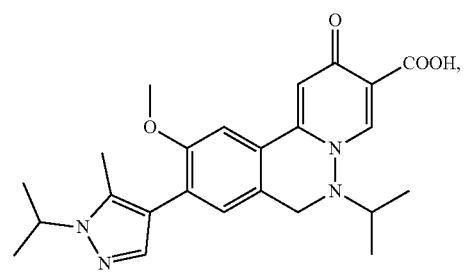
(10)
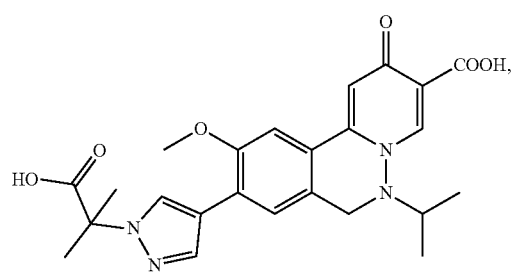
-continued
(11)
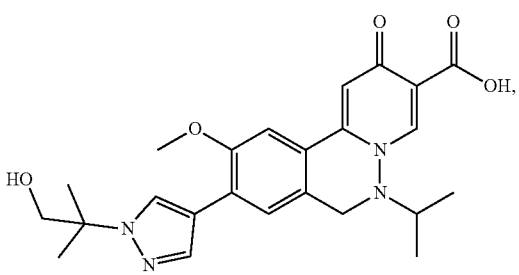
(12)
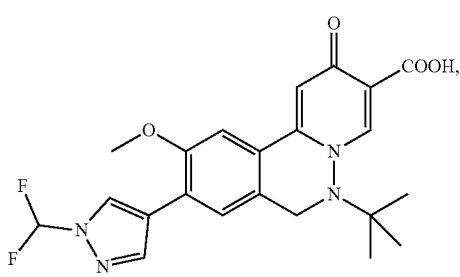
(13)
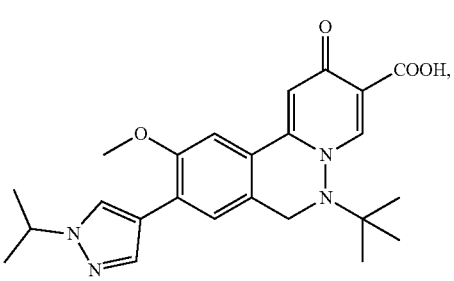
(14)
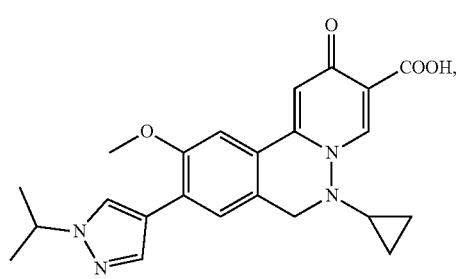
(15)
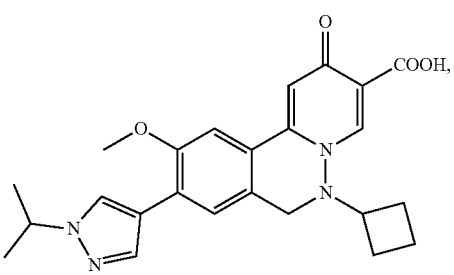

(16) 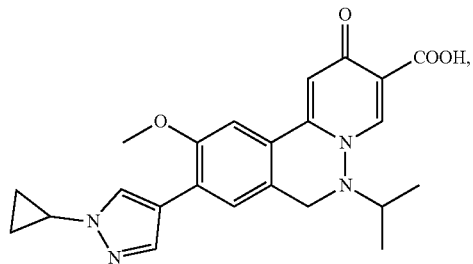
(17) 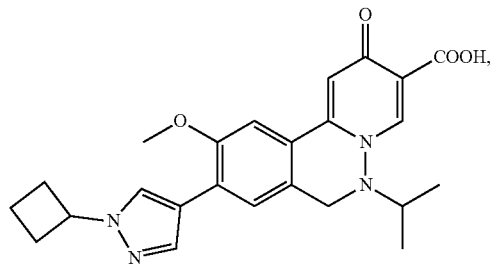
(18) 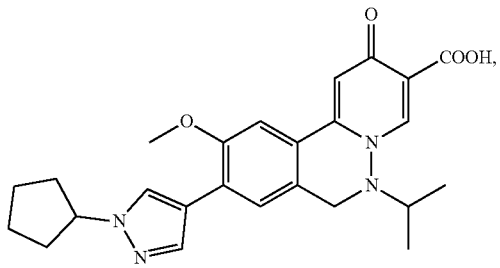
(19) 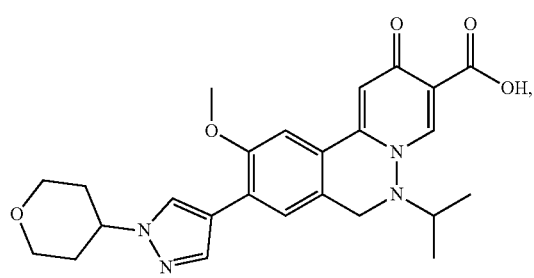
(20) 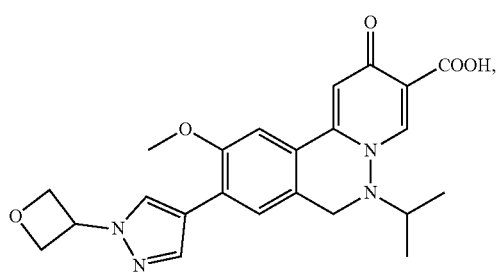
(21) 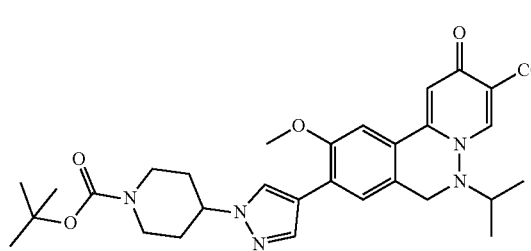
(22) 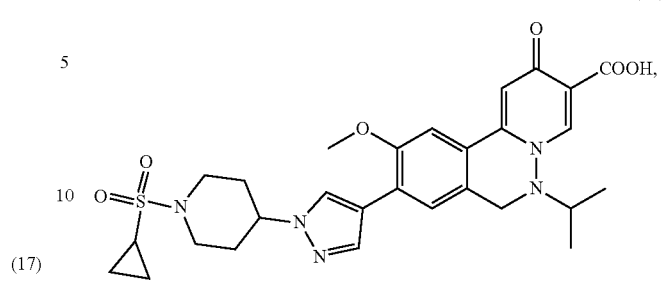
(23) 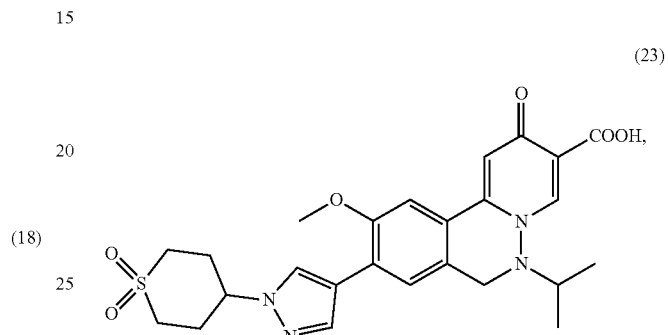
(24) 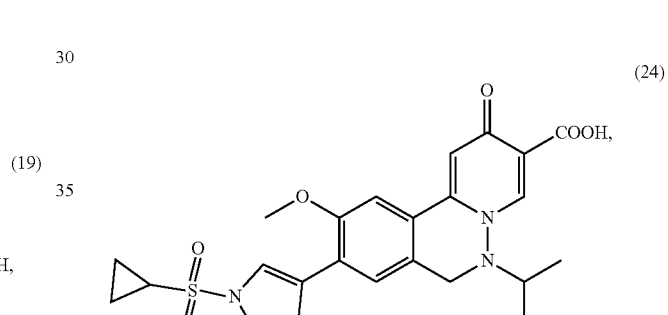
(25) 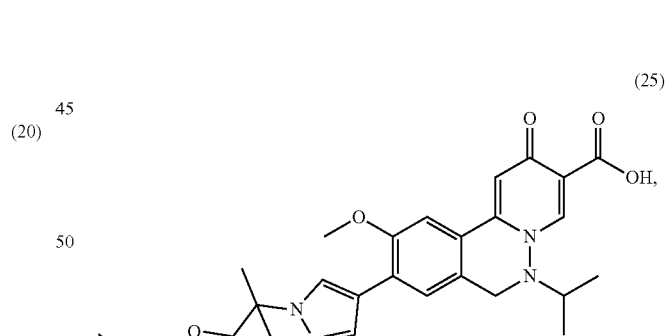
(26) 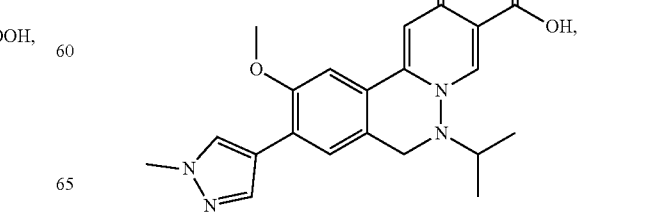

101
-continued
(27)
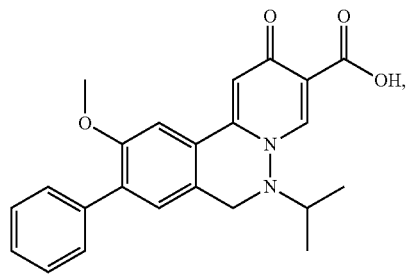
(28)
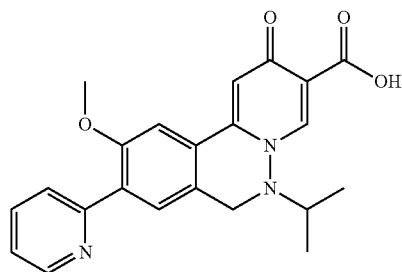
(29)
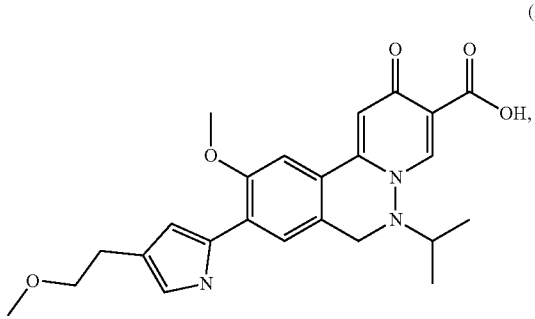
(30)
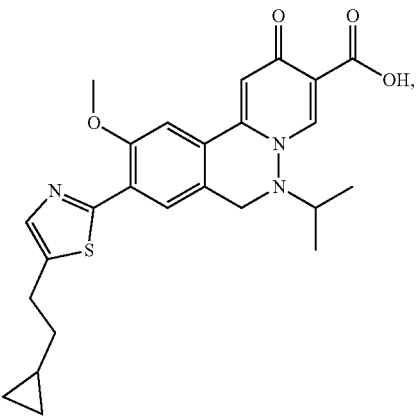
(31)
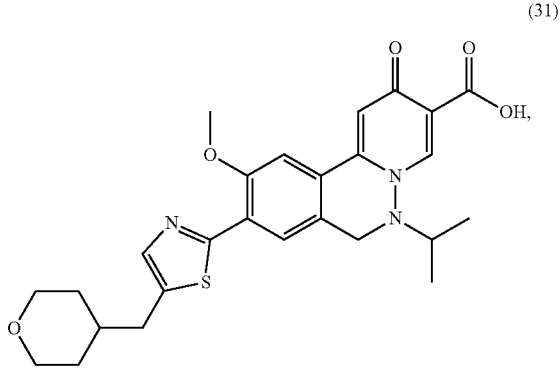
102
-continued
(32)
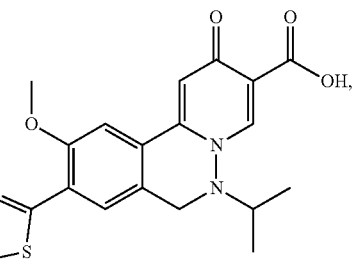
(33)
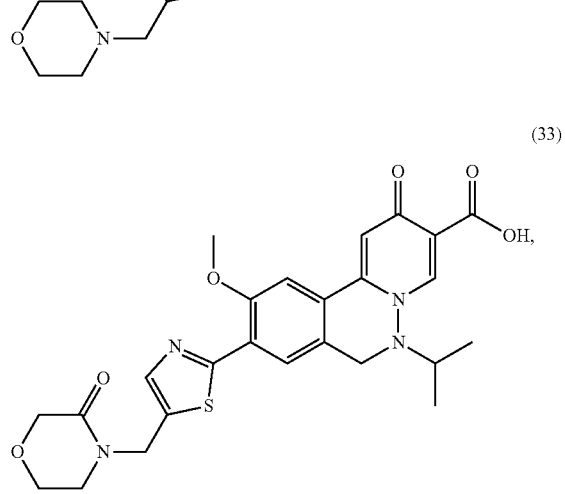
(34)
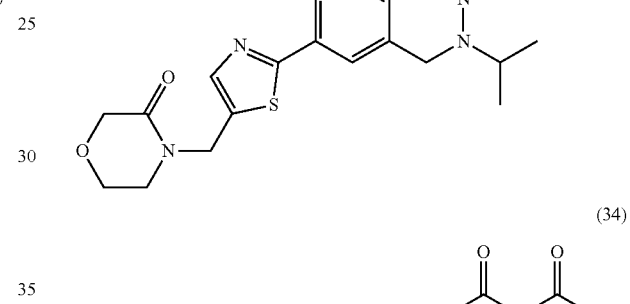
(35)
(36)
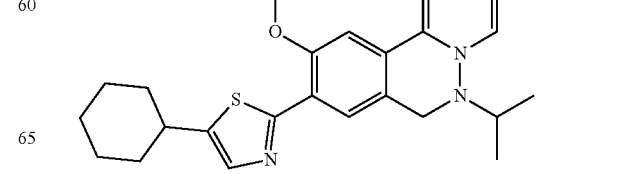

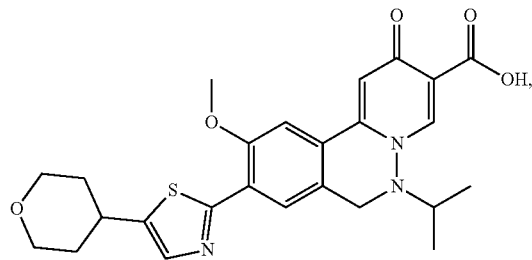
(37)
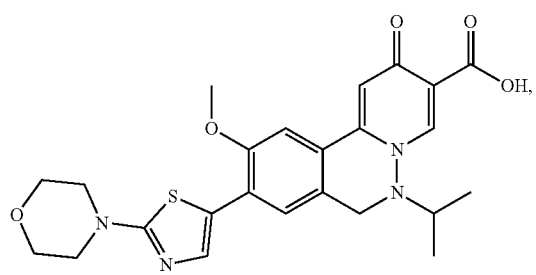
(38)
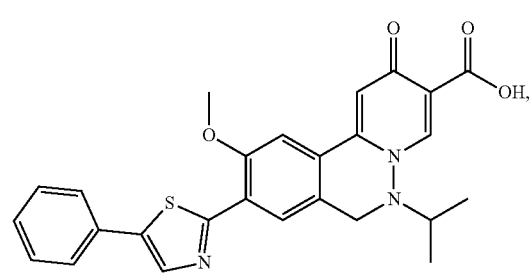
(39)
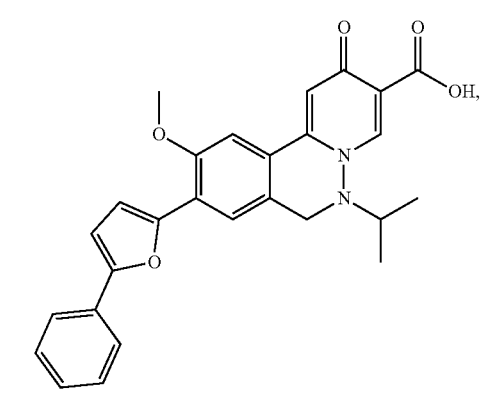
(40)
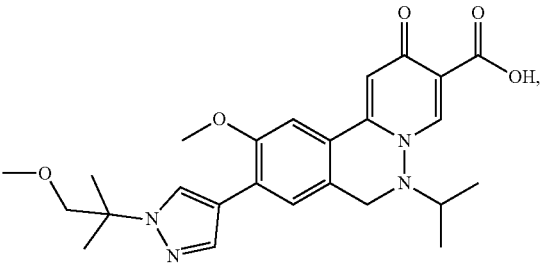
(41)
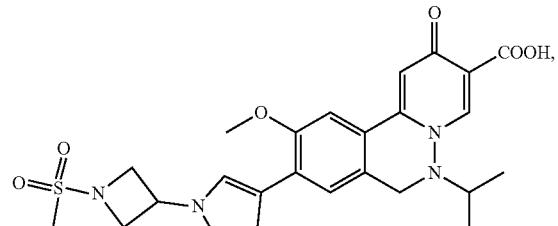
(42)
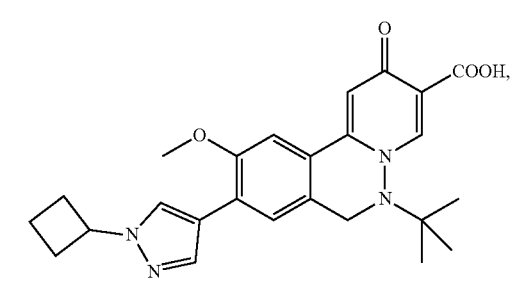
(43)
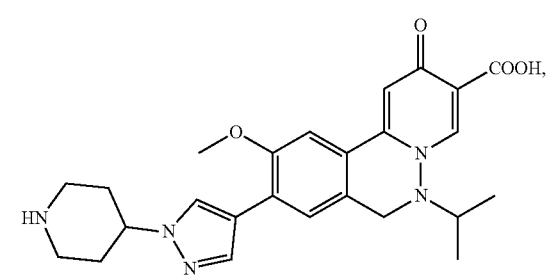
(44)
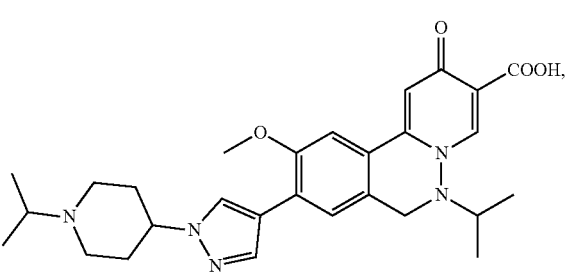
(45)
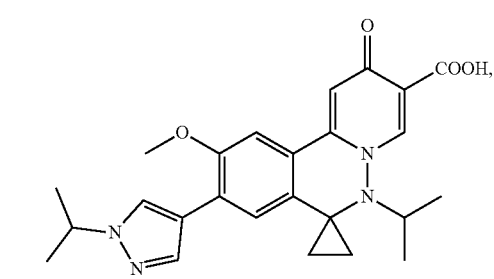
(46)

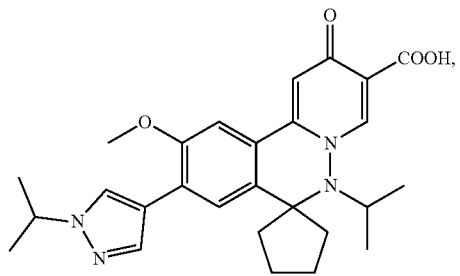
(47)
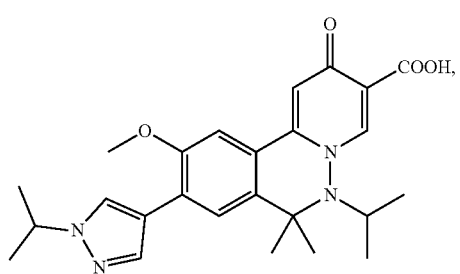
(48)
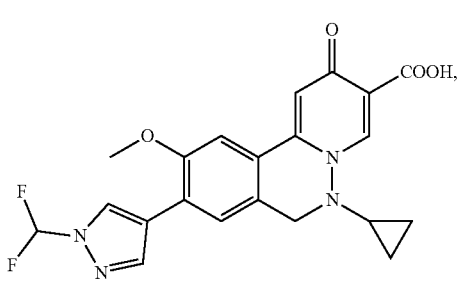
(49)
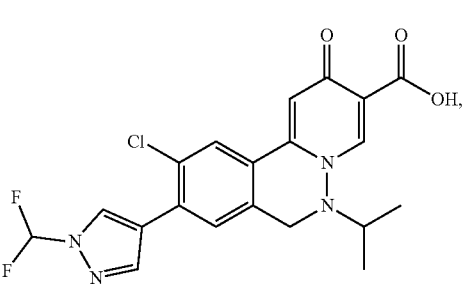
(50)
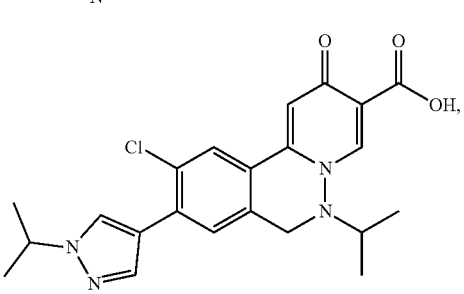
(51)
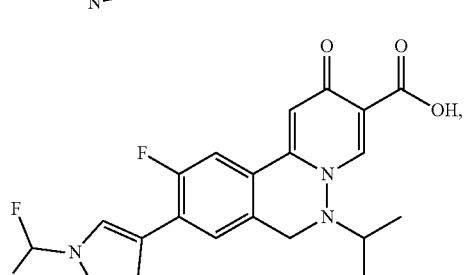
(52)
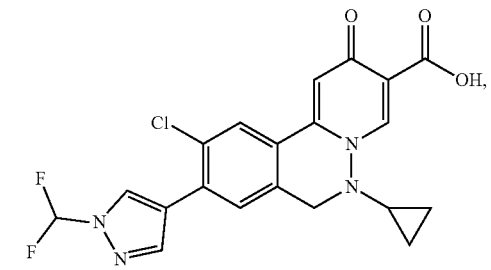
(53)
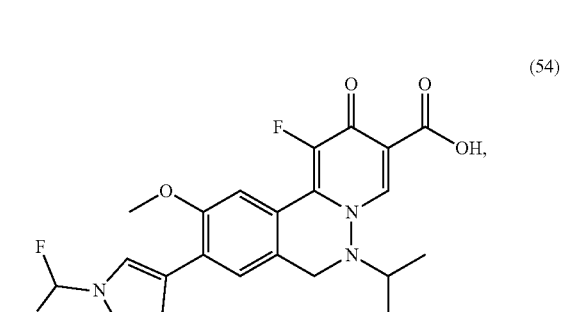
(54)
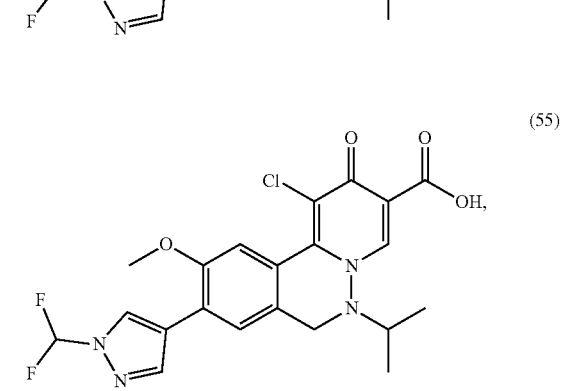
(55)
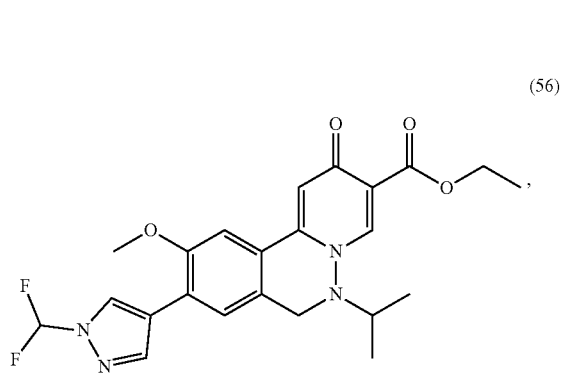
(56)
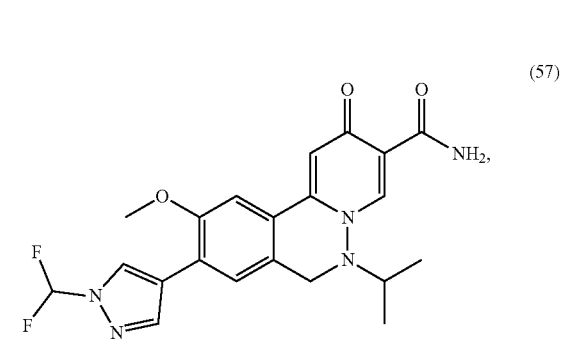
(57)

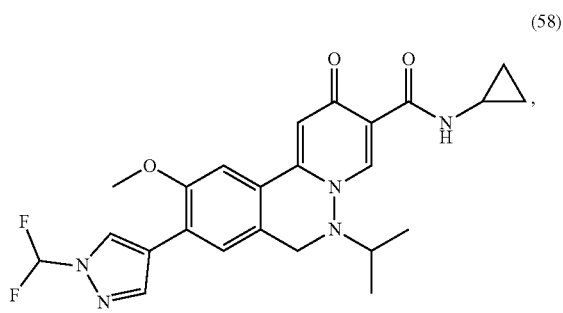

(58)

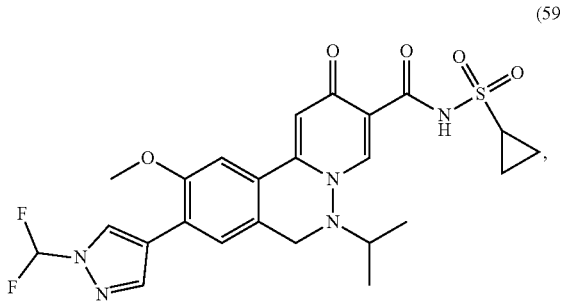

(59)

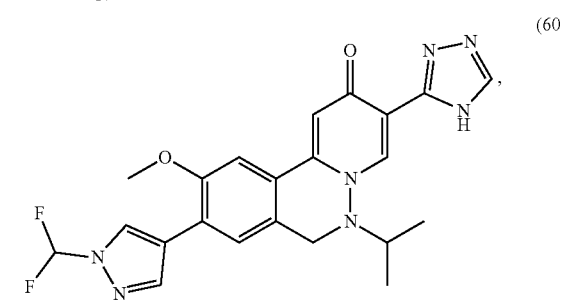

(60)

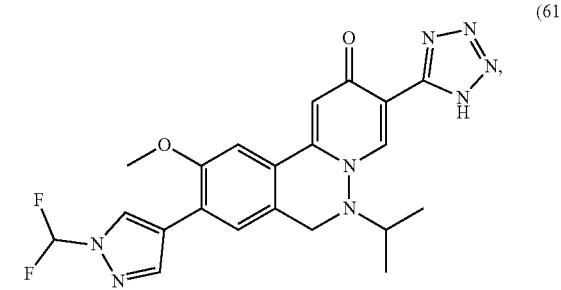

(61)

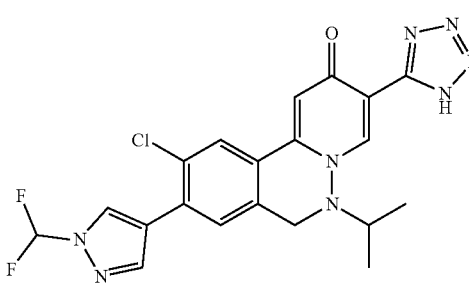

(62)

or stereoisomers, tautomers, N-oxides, solvates, or pharmaceutically acceptable salts thereof.

16. A pharmaceutical composition comprising the compound of claim 1, and further comprising pharmaceutically acceptable excipients or combinations thereof.

17. The pharmaceutical composition of claim 16 further comprising other anti-HBV drugs, wherein other anti-HBV drugs are HBV polymerase inhibitors, immunomodulators or interferons; or
wherein other anti-HBV drugs are Lamivudine, telbivudine, tenofovir Disoprox, entecavir, adefovir Dipivoxil, Alfaferone, Alloferon, Celmoleukin, Clevudine, emtricitabine, famciclovir, interferon, Hepa Tect CP, Interferon, Interferon α-1b, Interferon α, Interferon α-2a, Interferon β-1a, Interferon α-2, Interleukin-2, mivotilate, nitazoxanide, peginterferon α-2a, ribavirin, Roferon-A, Sizofiran, Euforavac, Ampligen, Phosphazid, Heplisav, interferon α-2b, levamisole or Propagermanium.

18. A method of treating or lessening viral diseases, comprising administering a therapeutically effective dose of the compound of claim 1 to a subject, wherein the viral disease is Hepatitis B virus infection or a disease caused by Hepatitis B virus infection.

19. The method of claim 18, wherein the disease caused by Hepatitis B virus infection is cirrhosis or hepatocellular carcinoma.

20. A method of treating or lessening viral diseases, comprising administering a therapeutically effective dose of the pharmaceutical composition of claim 16 to a subject, wherein the viral disease is Hepatitis B virus infection or a disease caused by Hepatitis B virus infection.

21. The method of claim 20, wherein the disease caused by Hepatitis B virus infection is cirrhosis or hepatocellular carcinoma.

* * * * *